(12) United States Patent
Frey et al.

(10) Patent No.: US 6,764,491 B2
(45) Date of Patent: Jul. 20, 2004

(54) DEVICES AND TECHNIQUES FOR A POSTERIOR LATERAL DISC SPACE APPROACH

(75) Inventors: George Frey, Englewood, CO (US);
John L. White, Bartlett, TN (US);
Mingyan Liu, Bourg-la-Reine (FR);
Loic Josse, Palaja (FR)

(73) Assignee: SDGI Holdings, Inc., Wilmington, DE (US)

( * ) Notice: Subject to any disclaimer, the term of this patent is extended or adjusted under 35 U.S.C. 154(b) by 259 days.

(21) Appl. No.: 09/858,197

(22) Filed: May 15, 2001

(65) Prior Publication Data

US 2002/0019637 A1 Feb. 14, 2002

Related U.S. Application Data

(63) Continuation-in-part of application No. 09/694,521, filed on Oct. 23, 2000.
(60) Provisional application No. 60/160,667, filed on Oct. 21, 1999.

(51) Int. Cl.[7] .............................................. A61B 17/56
(52) U.S. Cl. ......................................... 606/85; 606/170
(58) Field of Search .............................. 606/79, 84–86, 606/99, 167, 170; 407/29.1

(56) References Cited

U.S. PATENT DOCUMENTS

| 2,876,777 | A | * | 3/1959 | Kees, Jr. ....................... 606/84 |
| 3,848,601 | A | | 11/1974 | Ma et al. |
| 3,916,907 | A | | 11/1975 | Peterson |
| 4,306,550 | A | | 12/1981 | Forte |
| 4,349,921 | A | | 9/1982 | Kuntz |
| 4,545,374 | A | | 10/1985 | Jacobson |
| 4,573,448 | A | | 3/1986 | Kambin |
| 4,646,738 | A | | 3/1987 | Trott |
| 4,714,469 | A | | 12/1987 | Kenna |
| 4,736,738 | A | | 4/1988 | Lipovsek et al. |
| 4,743,256 | A | | 5/1988 | Brantigan |
| 4,820,305 | A | | 4/1989 | Harms et al. |
| 4,834,757 | A | | 5/1989 | Brantigan |
| 4,877,020 | A | | 10/1989 | Vich |
| 4,878,915 | A | | 11/1989 | Brantigan |
| 4,898,161 | A | | 2/1990 | Grundei |

(List continued on next page.)

FOREIGN PATENT DOCUMENTS

| DE | 27 32 325 A1 | 1/1979 |
| EP | 0 613 662 A2 | 9/1994 |
| FR | 2 736 537 A1 | 1/1997 |
| FR | 2 808 673 A1 | 11/2001 |
| WO | WO 01/28469 A2 | 4/2001 |

OTHER PUBLICATIONS

Horst G. Blume, M.D., Unilateral PLIF, Unilateral Posterior Lumbar Interbody Fusion: Simplified Dowel Technique, pp 75–84, Clinical Ortopaedics and Related Research; 1984.

Sofamor Danek The Spine Specialist, Surgical Technique Using Bone Dowel Instrumentation for Anterior Approach, 1996.

*Primary Examiner*—Kevin Shaver
*Assistant Examiner*—Michael B. Priddy
(74) *Attorney, Agent, or Firm*—Woodard, Emhardt, Moriarty McNett & Henry LLP

(57) ABSTRACT

This invention relates to methods and instruments for performing disc space preparation and implant insertion from a unilateral approach to the spine through a posterior lateral opening to the disc space. The instruments include spreaders, distractors, reamers, scrapers, cutters, chisels, rasps, pushers and implant inserters. A surgical procedure is provided that allows bilateral support of the adjacent vertebrae with at least one interbody fusion device inserted into the disc space via a unilateral approach. Implants for insertion into the disc space are also provided.

62 Claims, 43 Drawing Sheets

U.S. PATENT DOCUMENTS

| | | |
|---|---|---|
| 4,904,261 A | 2/1990 | Dove et al. |
| 4,917,704 A | 4/1990 | Frey et al. |
| 4,955,908 A | 9/1990 | Frey et al. |
| 5,015,247 A | 5/1991 | Michelson |
| 5,019,081 A | 5/1991 | Watanabe |
| 5,026,386 A | 6/1991 | Michelson |
| 5,122,134 A | 6/1992 | Borzone et al. |
| 5,123,926 A | 6/1992 | Pisharodi |
| 5,133,719 A | 7/1992 | Winston |
| 5,135,528 A | 8/1992 | Winston |
| 5,147,402 A | 9/1992 | Bohler et al. |
| 5,163,939 A | 11/1992 | Winston |
| 5,192,327 A | 3/1993 | Brantigan |
| 5,217,463 A | 6/1993 | Mikhail |
| 5,250,061 A | 10/1993 | Michelson |
| 5,344,459 A | 9/1994 | Swartz |
| 5,395,317 A | 3/1995 | Kambin |
| 5,397,364 A | 3/1995 | Kozak et al. |
| 5,403,317 A | 4/1995 | Bonutti |
| 5,431,658 A | 7/1995 | Moskovich |
| 5,439,464 A | 8/1995 | Shapiro |
| 5,514,180 A | 5/1996 | Heggeness et al. |
| 5,586,989 A * | 12/1996 | Bray, Jr. .................... 606/160 |
| 5,599,279 A | 2/1997 | Slotman et al. |
| 5,607,424 A | 3/1997 | Tropiano |
| 5,609,635 A | 3/1997 | Michelson |
| 5,609,636 A | 3/1997 | Kohrs et al. |
| 5,609,637 A | 3/1997 | Biedermann et al. |
| 5,620,458 A | 4/1997 | Green et al. |
| 5,688,284 A | 11/1997 | Chervitz et al. |
| 5,697,889 A | 12/1997 | Slotman et al. |
| 5,702,451 A | 12/1997 | Biedermann et al. |
| 5,730,754 A | 3/1998 | Obenchain |
| 5,741,253 A | 4/1998 | Michelson |
| 5,741,261 A | 4/1998 | Moskovitz et al. |
| 5,755,732 A | 5/1998 | Green et al. |
| 5,766,252 A | 6/1998 | Henry et al. |
| 5,772,661 A | 6/1998 | Michelson |
| 5,776,199 A | 7/1998 | Michelson |
| 5,836,948 A | 11/1998 | Zucherman et al. |
| 5,857,995 A | 1/1999 | Thomas et al. |
| 5,860,973 A | 1/1999 | Michelson |
| 5,860,977 A | 1/1999 | Zucherman et al. |
| 5,861,041 A | 1/1999 | Tienboon |
| 5,888,224 A | 3/1999 | Beckers et al. |
| 5,893,890 A | 4/1999 | Pisharodi |
| 5,925,056 A | 7/1999 | Thomas et al. |
| 5,951,564 A | 9/1999 | Schroder et al. |
| 5,961,522 A | 10/1999 | Mehdizadeh |
| 5,968,062 A | 10/1999 | Thomas et al. |
| 5,972,031 A | 10/1999 | Biedermann et al. |
| 5,984,922 A | 11/1999 | McKay |
| 5,989,290 A | 11/1999 | Biedermann et al. |
| 6,048,345 A * | 4/2000 | Berke et al. .................. 606/85 |
| 6,074,390 A | 6/2000 | Zucherman et al. |
| 6,086,613 A | 7/2000 | Camino et al. |
| 6,102,930 A | 8/2000 | Simmons, Jr. |
| 6,102,949 A | 8/2000 | Biedermann et al. |
| 6,110,175 A | 8/2000 | Scholl |
| 6,113,639 A | 9/2000 | Ray et al. |
| 6,126,664 A | 10/2000 | Troxell et al. |
| 6,143,032 A | 11/2000 | Schafer et al. |
| 6,149,651 A | 11/2000 | Drewry et al. |
| 6,159,215 A | 12/2000 | Urbahns et al. |
| 6,174,311 B1 | 1/2001 | Branch et al. |
| 6,176,882 B1 | 1/2001 | Biedermann et al. |
| 6,224,603 B1 | 5/2001 | Marino |
| 6,241,771 B1 | 6/2001 | Gresser et al. |
| 6,245,108 B1 | 6/2001 | Biscup |
| 6,258,125 B1 | 7/2001 | Paul et al. |
| 6,261,296 B1 | 7/2001 | Aebi et al. |
| 6,290,724 B1 | 9/2001 | Marino |
| 6,319,257 B1 | 11/2001 | Carignan et al. |
| 6,425,920 B1 * | 7/2002 | Hamada .................. 623/17.16 |
| 6,436,101 B1 | 8/2002 | Hamada |
| 2002/0045904 A1 | 4/2002 | Fuss et al. |
| 2002/0055781 A1 | 5/2002 | Sazy |
| 2002/0077700 A1 | 6/2002 | Varga et al. |
| 2002/0165612 A1 | 11/2002 | Gerber et al. |

* cited by examiner

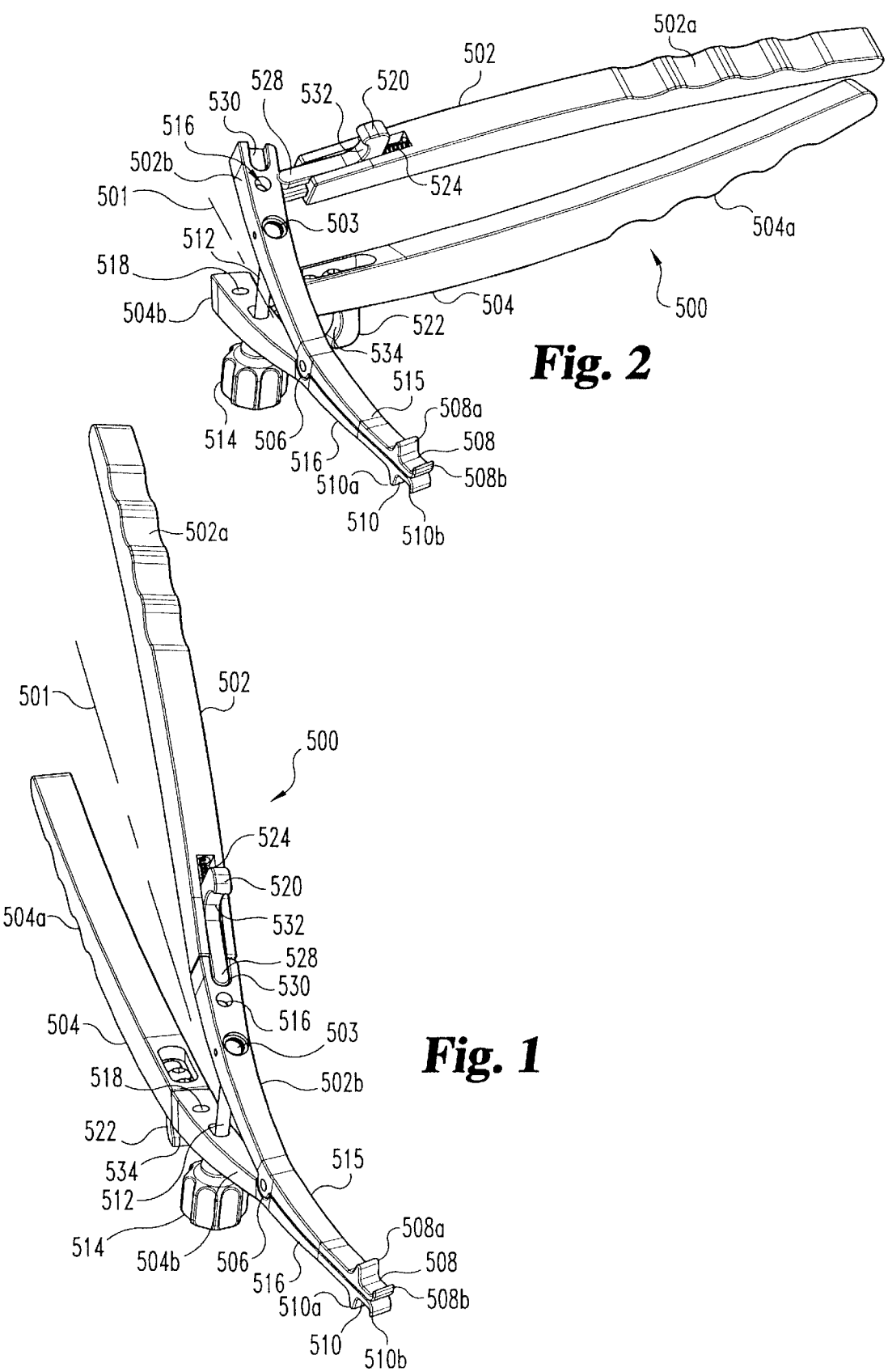

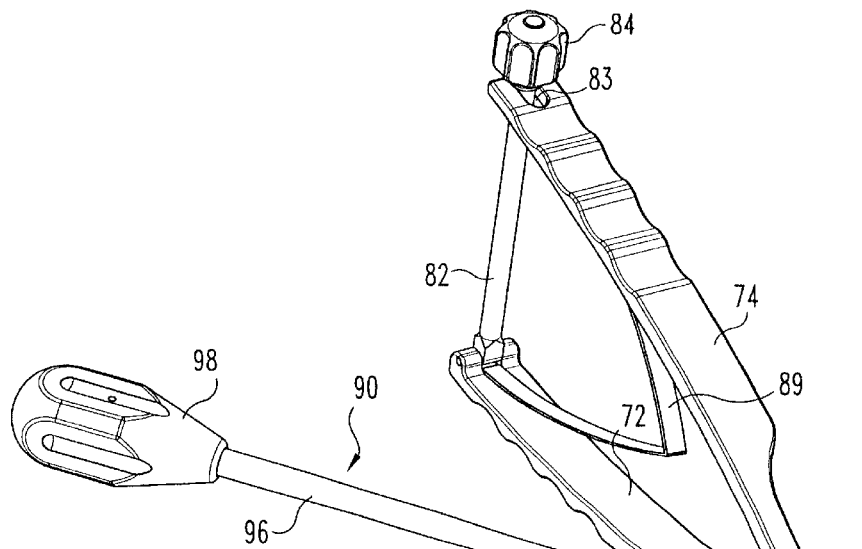
Fig. 5(a)
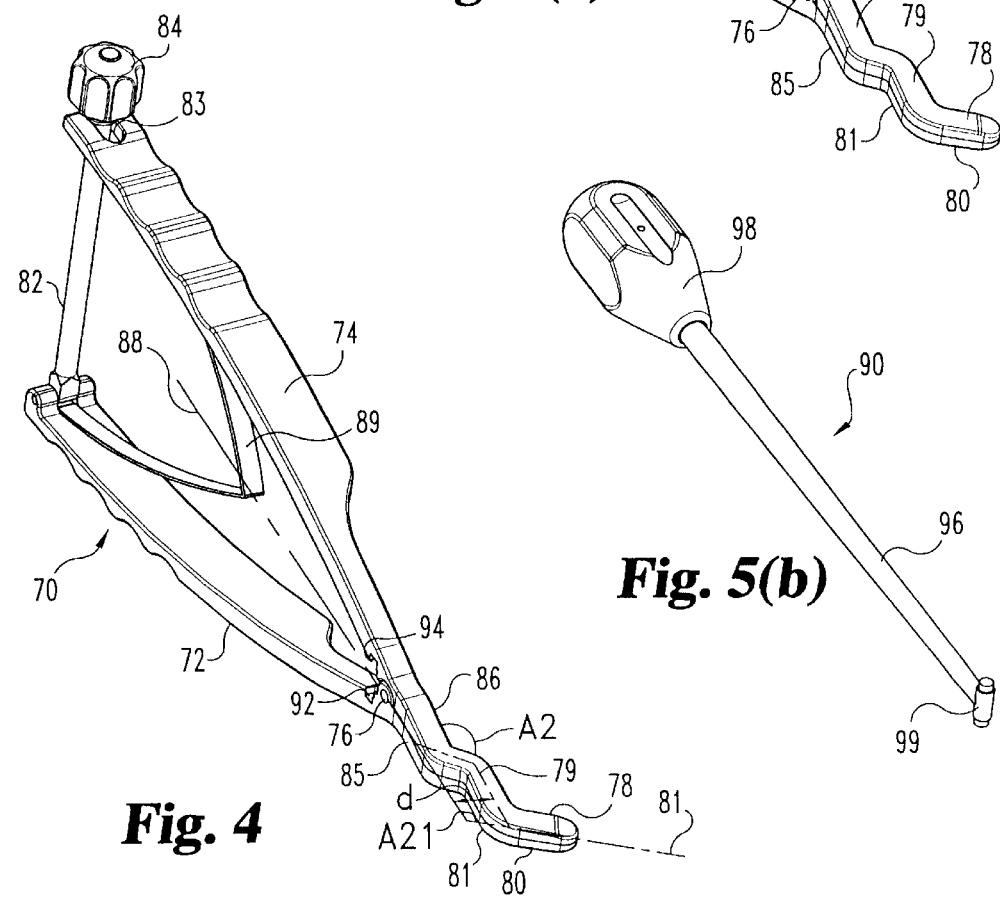
Fig. 4
Fig. 5(b)

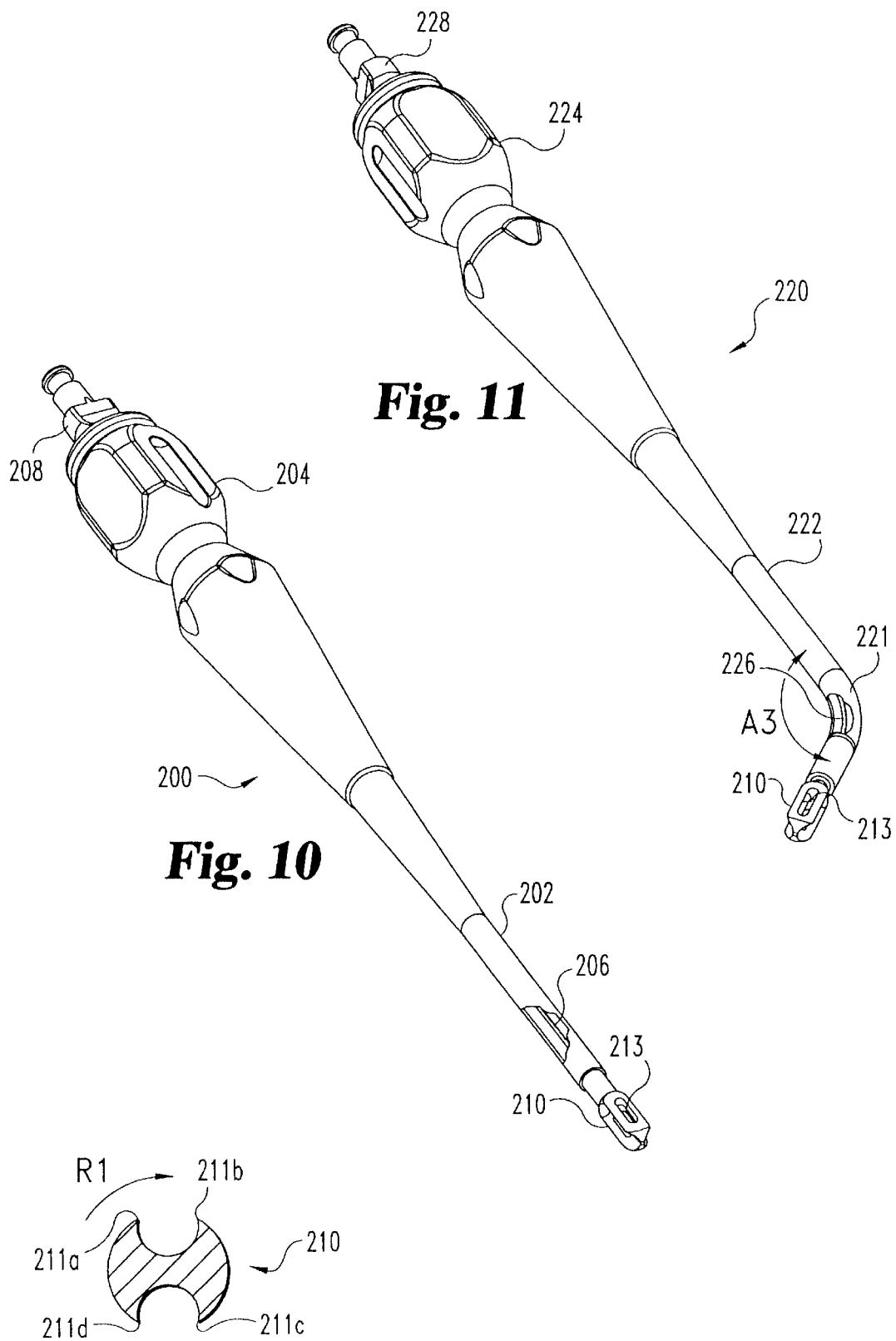

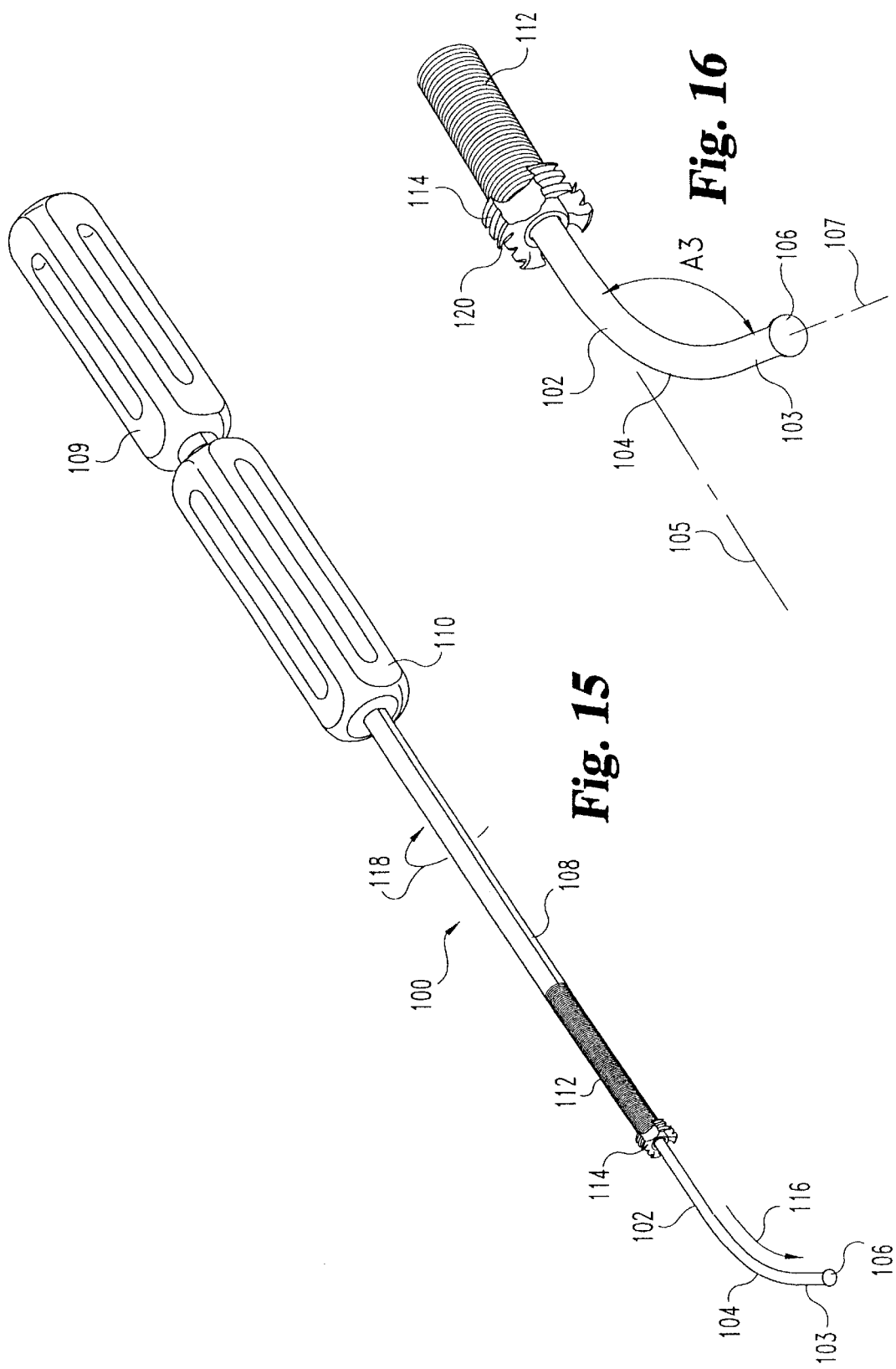

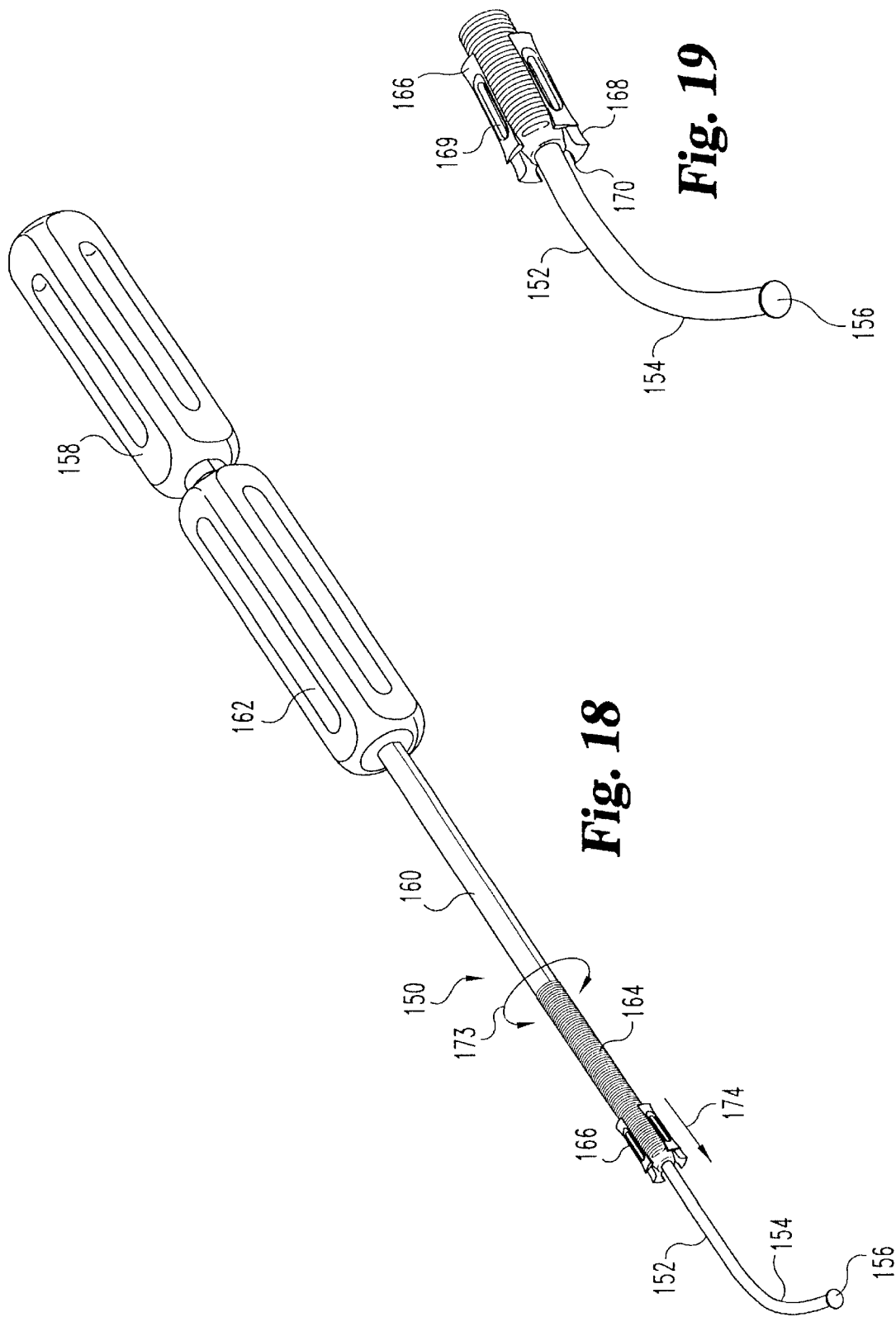

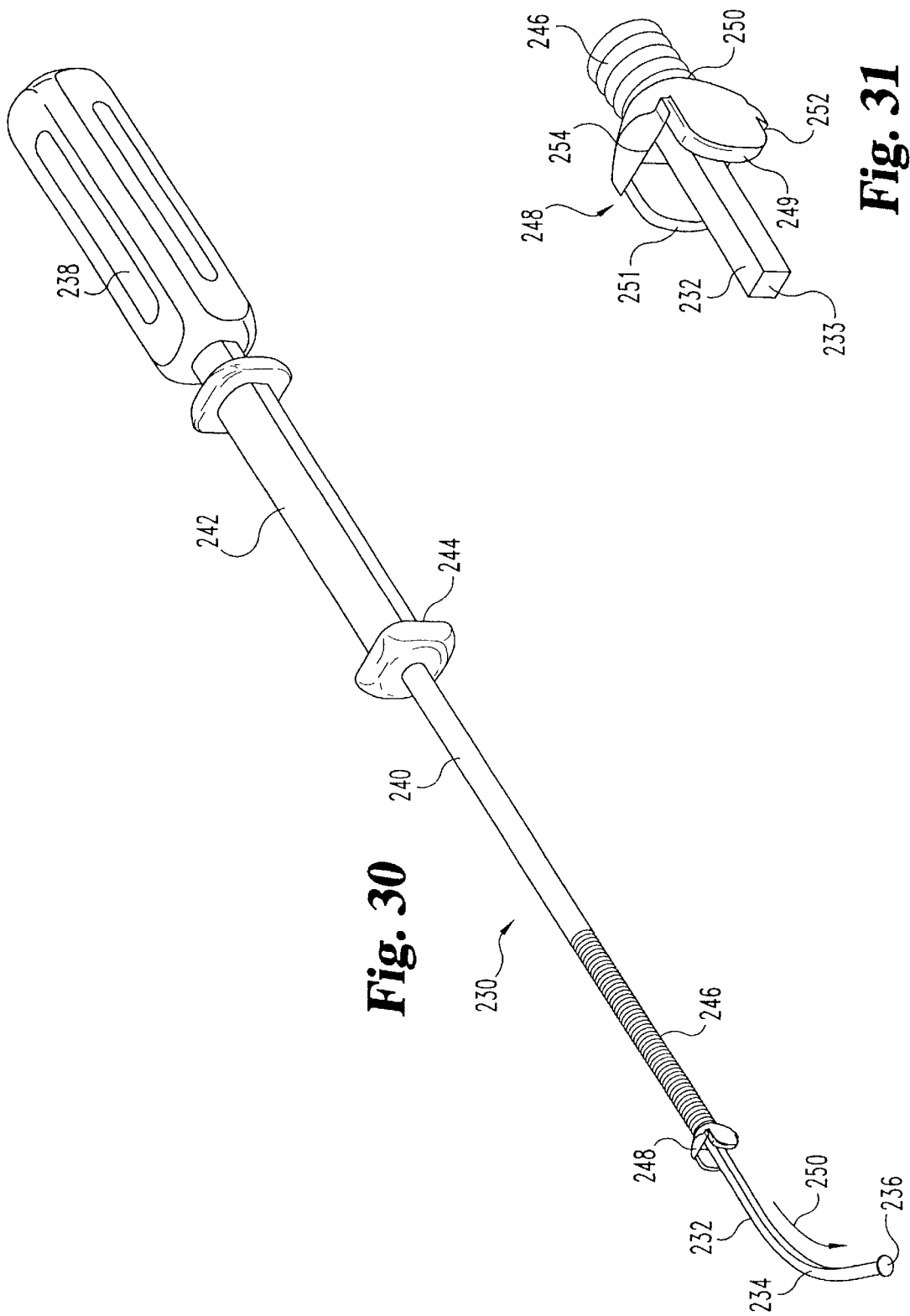

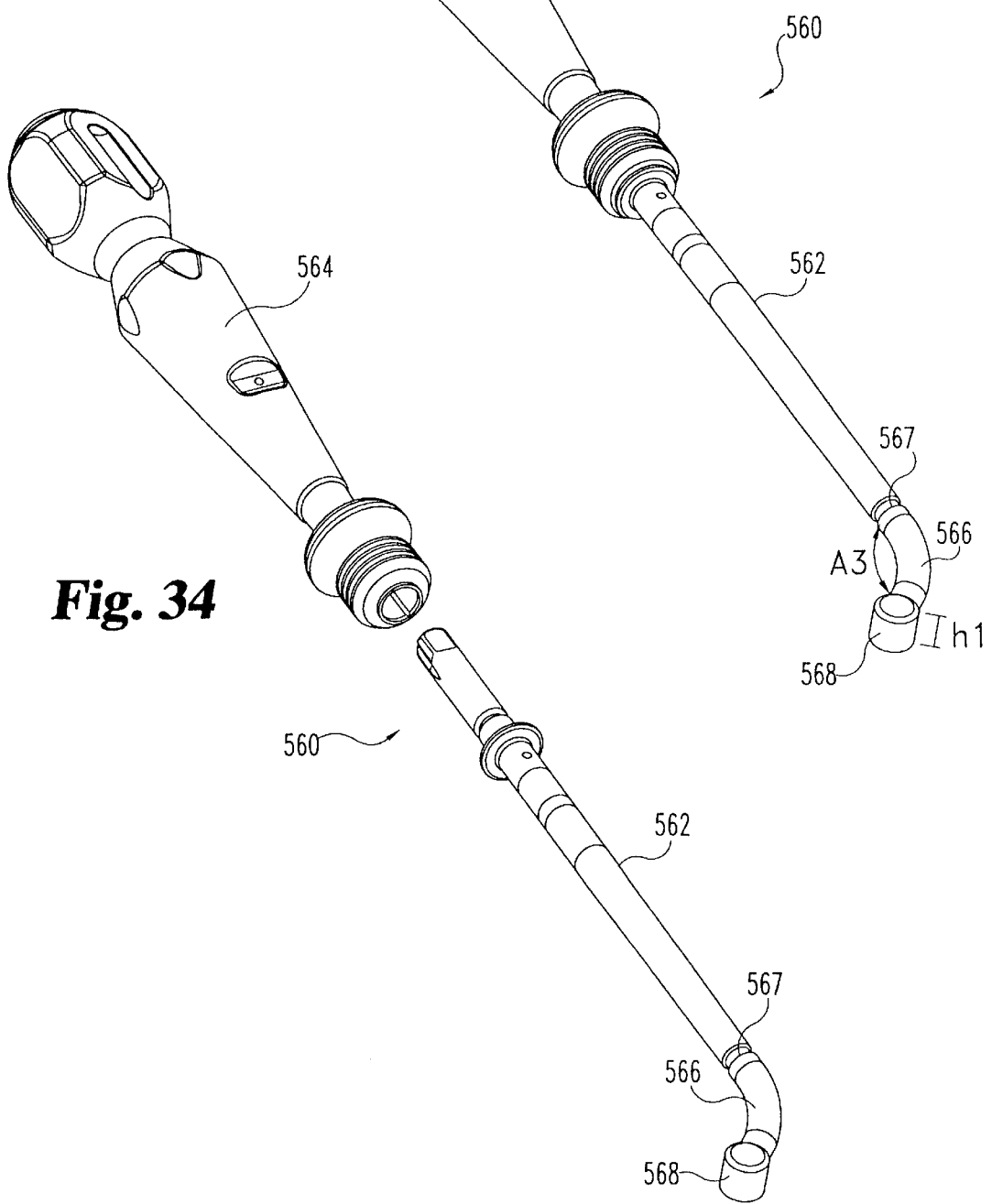

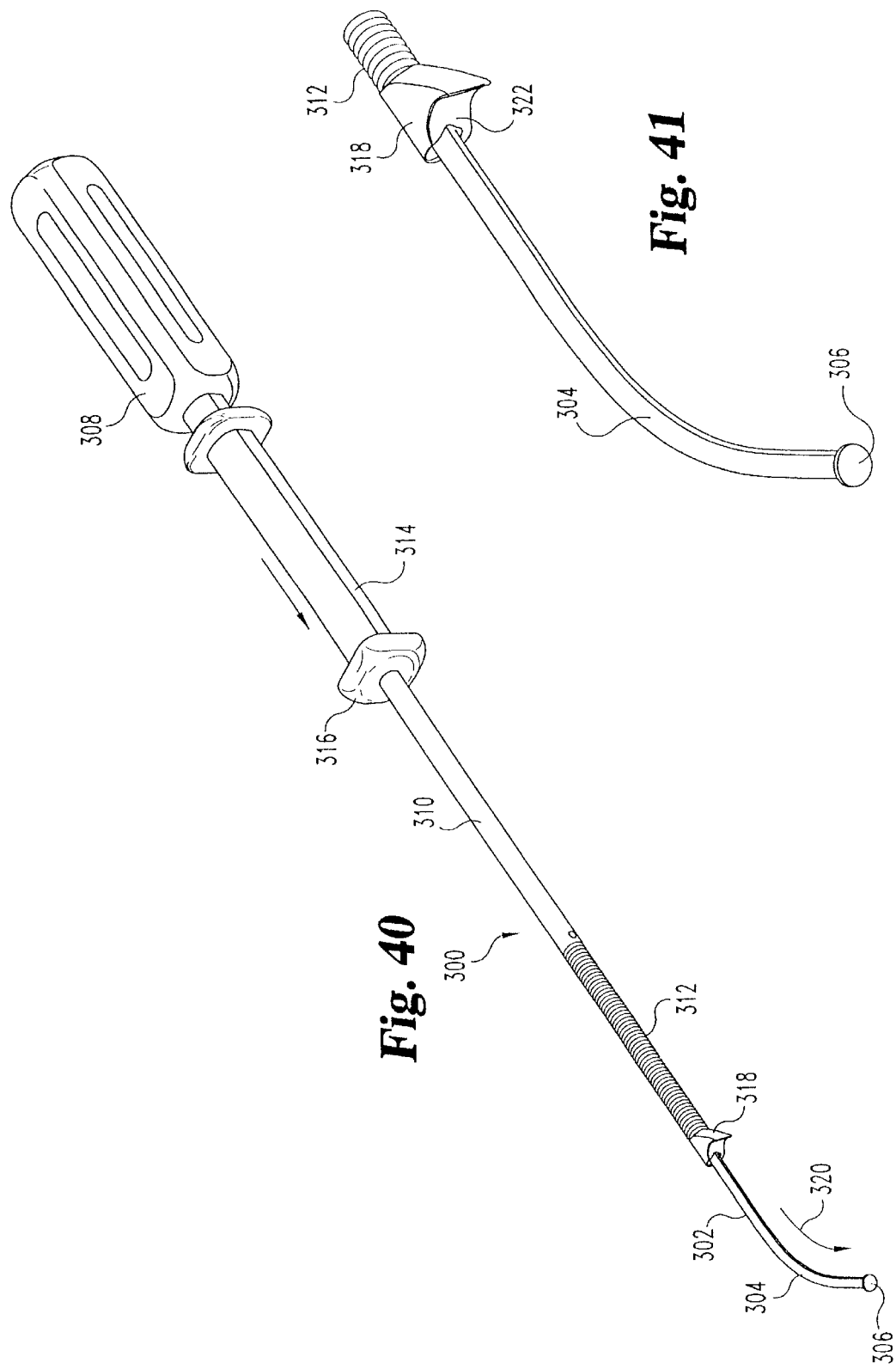

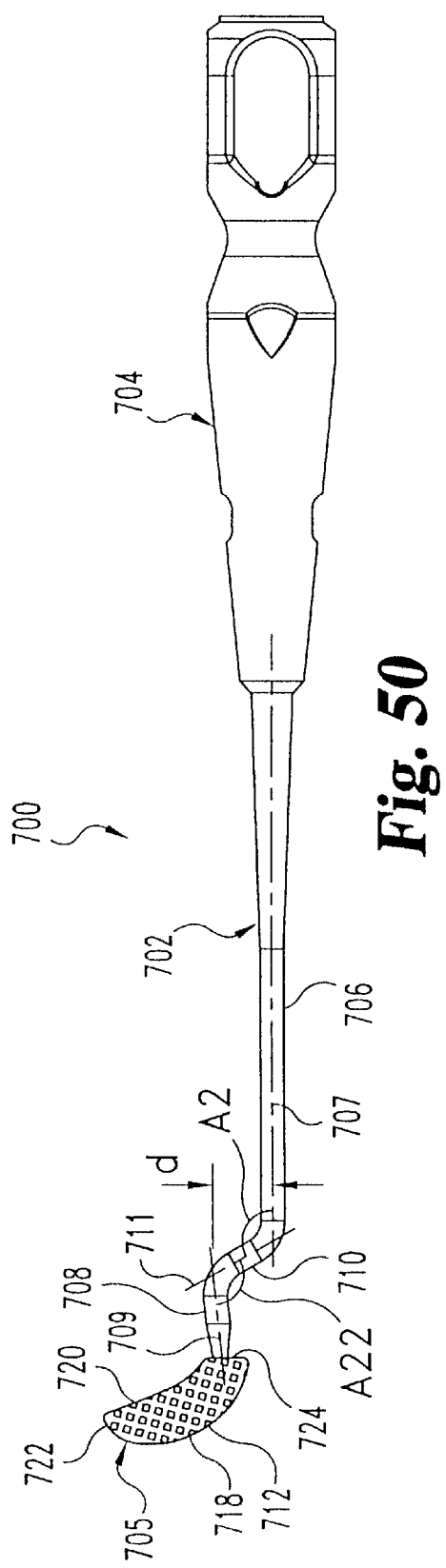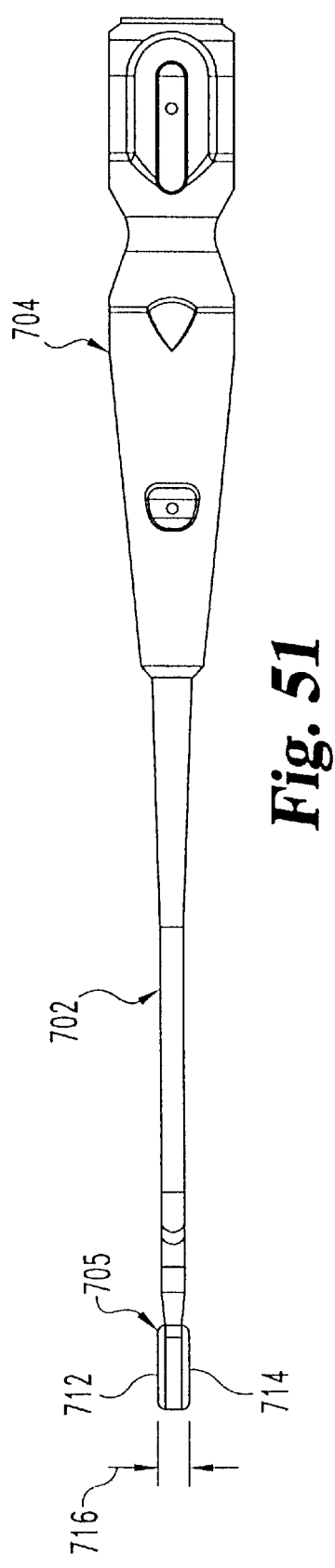
Fig. 50
Fig. 51

DEVICES AND TECHNIQUES FOR A POSTERIOR LATERAL DISC SPACE APPROACH

CROSS-REFERENCE TO RELATED APPLICATIONS

The present application is a continuation-in-part of pending U.S. patent application Ser. No. 09/694,521, filed on Oct. 23, 2000, which claims the benefit of the filing date of Provisional Application No. 60/160,667, filed Oct. 21, 1999.

BACKGROUND OF THE INVENTION

The present invention relates to techniques for use in interbody fusion procedures, instruments for performing such procedures, and implants insertable in the spinal disc space. More specifically, but not exclusively, the present invention relates to implants, methods and instruments for use in a posterior lateral approach to the disc space, such as a transforaminal approach.

Normally intervertebral discs, which are located between endplates of adjacent vertebrae, stabilize the spine and distribute forces between the vertebrae and cushion vertebral bodies. The spinal discs may be displaced or damaged due to trauma, disease or aging. A herniated or ruptured annulus fibrosis may result in nerve damage, pain, numbness, muscle weakness, and even paralysis. Furthermore, as a result of the normal aging processes, discs dehydrate and harden, thereby reducing the disc space height and producing instability of the spine and decreased mobility. Most typically surgical correction of a collapsed disc space includes a discectomy (surgical removal of a portion or the entire intervertebral disc). The discectomy is often followed by restoration of normal disc space height and bony fusion of the adjacent vertebrae to maintain the disc space height.

Access to a damaged disc space may be accomplished from several approaches to the spine. One approach is to gain access to the anterior portion of the spine through a patient's abdomen. However, extensive vessel retraction is often required and many vertebral levels are not readily accessible from this approach. A posterior approach may also be utilized. However, this typically requires that both sides of the disc space on either side of the spinal cord be surgically exposed. This may require a substantial incision or multiple access locations, as well as extensive retraction of the spinal cord. To alleviate problems associated with both anterior and posterior approaches to the spine, a posterior lateral approach, such as a transforaminal approach, to the disc space may be utilized. While it is desirable to place one or more implants in the disc space so that the load of the spinal column is evenly distributed, accurate placement of implants in the disc space from a single posterior lateral approach has heretofore been extremely difficult. Thus, this approach to the spine is seldom used in practice.

Therefore, there remains a need for improved instruments, implants and techniques for use in a posterior lateral approach to the disc space that allows unilateral disc space preparation and implant insertion to provide bilateral stability to the subject disc space.

SUMMARY OF THE INVENTION

The present invention provides implants, instruments and methods particularly adapted for unilateral disc space preparation and implant insertion from a posterior lateral approach to the disc space, such as is provided with a transforaminal approach.

In one aspect a lamina spreader is provided. The lamina spreader has arms pivotally connected with one another. The arms each include a lamina engaging portion at the distal end of the arm. In a preferred form, the arms are hinged so that the proximal ends of the arms can be rotated out of the operative field while the spreader is engaged to the lamina.

In another aspect, a disc space spreader is provided. The spreader has a pair of branches pivotally connected to one another. The branches have a spreading portion attached to the distal end of each arm. Each arm includes a lateral offset extending between the spreading portion and the articulating arm. A spreading mechanism is provided to assist in separating the spreading portions. In a further form, a pusher is provided to assist the surgeon in inserting the spreading portions into the disc space.

In further aspect of the invention, rotatable distractors are provided with distractor heads configured for insertion into the disc space via a unilateral approach. A lever arm can be secured to the distractor shaft to assist in rotation of the distractor.

In still a further aspect of the invention, cutting tools for unilateral disc space preparation are provided. Cutting instruments according to the present invention preferably have a longitudinal shaft with a cutting blade disposed at the distal end of the shaft. The cutting instruments include straight and curved reamers, cutting blades that are movable along or around a guide shaft, pull scrapers and push scrapers, straight chisels, and curved chisels movable along a guide shaft.

In yet another aspect, the present invention provides improved devices for implant insertion. An implant template is provided for the surgeon to determine the required implant size. Implant insertion devices according to the present invention comprise a shaft having a longitudinal axis and an implant connector at the distal end of the shaft. The shafts can be straight, curved, or flexible. In one form, the distal end of the shaft includes a bend for implant insertion to the distal portion of the disc space. In another form, the inserter shaft has a lateral offset. According to a further aspect of the invention, a pusher is provided and useable with the inserter to facilitate implant placement in the disc space.

In still a further aspect, the present invention provides methods for disc space preparation and implant insertion from a unilateral transforaminal approach to the spine. The method contemplates accessing the disc space and providing a posterior lateral opening into the disc space. The lamina can be spread to facilitate access. The disc space is then distracted with disc space spreaders. Cutting instruments are inserted through the opening to remove disc material and bony material from the endplates to prepared the disc space for implant insertion. The implant is then inserted through the opening and into the distal portion of the disc space. In one form, the unilateral approach utilizes at least two bilaterally positioned implants, with one of the implants in the distal portion of the disc space. In a second form, a single implant laterally spanning the disc space is positioned through the opening.

Further aspects, forms, embodiments, objects, features, benefits, aspects and advantages of the present invention shall become apparent from the detailed drawings and descriptions provided herein.

BRIEF DESCRIPTION OF THE DRAWINGS

FIG. 1 is a perspective view of a lamina spreader according to the present invention.

FIG. 2 is a perspective view of the lamina spreader of FIG. 1 with the handle portions rotated to a folded position.

FIG. 4 is a perspective view of a disc space spreader according to the present invention.

FIGS. 5(a) and 5(b) are perspective views of the disc space spreader of FIG. 4 with a lever arm and a perspective view of the lever arm, respectively.

FIG. 10 is a perspective view of a straight reamer according to the present invention having the outer shaft partially cut-away to show the inner shaft.

FIG. 11 is a perspective view of a curved reamer according to the present invention having the outer shaft partially cut-away to show the inner shaft.

FIG. 12 is an end view of the reamer cutting head used with the reamers of FIGS. 10 and 11.

FIG. 15 is a perspective view of a guided rotary cutter according to the present invention.

FIG. 16 is an enlarged view of the distal end portion of the cutter of FIG. 15.

FIG. 18 is a perspective view of a guided rotary cutting tool according to the present invention.

FIG. 19 is an enlarged perspective view of the distal end portion of the cutting tool of FIG. 18.

FIG. 30 is a perspective view of an alternate embodiment guided chisel according to the present invention.

FIG. 31 is an enlarged perspective view of the chisel head and shaft with the chisel head in the position of FIG. 30.

FIG. 33 is a perspective view an implant sizing guide according to one aspect of the present invention.

FIG. 34 is the implant sizing guide of FIG. 33 with the handle detached.

FIG. 40 is a perspective view of an alternate embodiment guided implant inserter according to the present invention.

FIG. 41 is an enlarged perspective view of the distal portion of the implant inserter of FIG. 40.

FIG. 50 is a plan view of an intradiscal rasp according to another aspect of the present invention.

FIG. 51 is a side elevational view of the intradiscal rasp of FIG. 50.

DETAILED DESCRIPTION OF THE PREFERRED EMBODIMENTS

Figure 3:
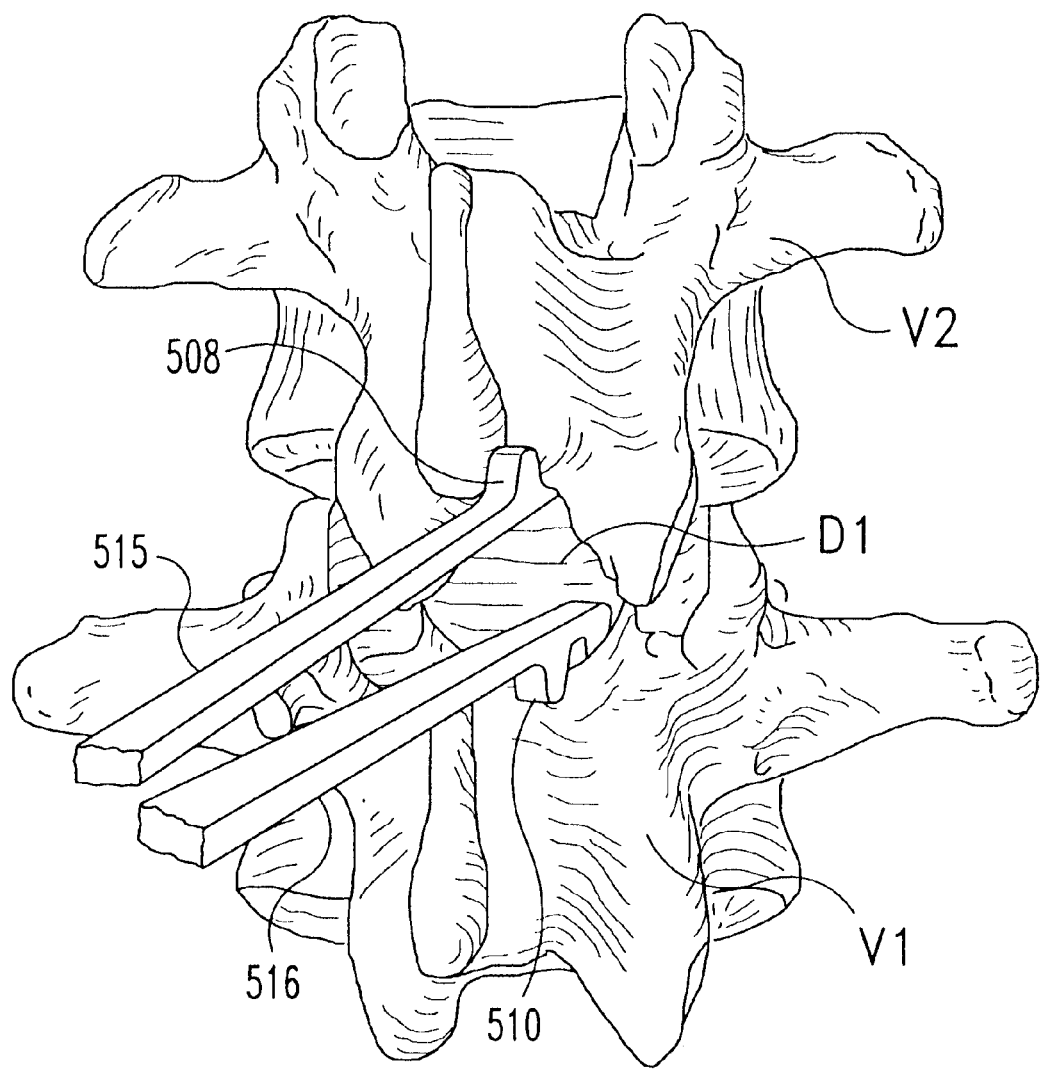
FIG. 3 is an elevational view of a spinal column segment showing the distal portion of the lamina spreader of FIG. 1 engaged to the lamina on either side of a disc space.

For the purposes of promoting an understanding of the principles of the present invention, reference will now be made to the embodiments illustrated in the drawings, and specific language will be used to describe the same. It will nevertheless be understood that no limitation of the scope of the invention is intended thereby. Any alterations and further modification in the described processes, systems, or devices, and any further applications of the principles of the invention as described herein are contemplated as would normally occur to one skilled in the art to which the invention relates.

In a posterior lateral approach to the disc space, such as is provided with a transforaminal approach, it is often difficult to prepare the proper locations in the disc space to receive an implant. The instruments and techniques of the present invention provide for improved unilateral disc space preparation in both the distal and proximal portions of the disc space through a single opening. Another difficulty in posterior lateral approaches to the disc space is related to the proper positioning of the implant in the portion of the disc space most distal from the posterior lateral opening. While it is desirable that the implant be positioned in the distal portion of the disc space, it is often too difficult to move the implant across the disc space to the distal portion. Thus, the present invention further provides implant inserters, implant templates, implant insertion guides, and implants that facilitate implant positioning in the distal and proximal portions of the disc from a posterior lateral approach.

Referring now to FIG. 1, there is provided a lamina spreader 500 according to one aspect of the present invention. Lamina spreader 500 includes a first arm 502 pivotally joined to a second arm 504 by pin 506. Arms 502, 504 extend generally along a central axis 501 when in a first spreading position. Extending distally from pin 506 are distal portions 515 and 516 of arms 502 and 504, respectively. Distal portions 515 and 516 include lamina engaging portions 508 and 510, respectively. Lamina engaging portions 508 and 510 are generally U-shaped and configured to engage the lamina of an upper vertebra V2 and the lamina of a lower vertebra V1, respectively, on either side of the subject disc space, as shown in FIG. 3. Spreading portion 508 includes an outer portion 508a configured to reside on the outer side of the lamina connected to an inner portion 508b configured to reside on the inner side of the lamina. Spreading portion 510 similarly includes an outer portion 510a configured to reside on the outer side of the lamina connected to an inner portion 510b configured to reside on the inner side of the lamina.

The lamina can be spread by the surgeon grasping handle 502a of arm 502 and handle 504a of arm 504, and forcing arms 502, 504 towards one another in the direction towards axis 501. There is also provided a mechanism to force and/or maintain spreading portions 508 and 510 apart. The spreading mechanism includes an externally threaded rod 512 threadingly engaged to branch 502 and a hand nut 514 received on rod 512. Arms 502 and 504 may be forced together by action of threading nut 514 to force rod 512 into threaded opening 503 in arm 502, thereby forcing spreading portions 508 and 510 apart and separating the lamina to open access to the disc space. Nut 514 can also be used to thread rod 512 into opening 503 after manually spreading the lamina via handles 502a, 504a, until nut 514 contacts arm 504 to maintain the engaging portions 508, 510 in a spread condition.

In a preferred form, arm 502 has handle portion 502a that is hinged to rotate with respect to a non-rotating portion 502b about a pin 516, and arm 504 has handle portion 504a hinged to rotate with respect to a non-rotating portion 504b about a pin 518. A first spring loaded locking mechanism 520 resides in cut-out 524 formed in handle portion 502a, and a second spring loaded locking mechanism 522 resides in a similar cut-out (not shown) formed in handle portion 504a. Locking mechanism 520 includes a finger 528 spring-biased into notch 530 formed in non-rotating portion 502b. The surgeon or attendant can release handle portion 502a by pulling proximally on grasping portion 532 to pull finger 528 out of notch 530, and then rotate handle portion 502a transversely to axis 501 about pin 516 to a position oriented about 90 degrees with respect to non-rotating portion 502b. Similarly, locking mechanism 522 includes a finger spring-biased into a notch formed in non-rotating portion 504b. The surgeon or attendant can release handle portion 504a by pulling proximally on grasping portion 534 to pull the finger out of the notch, and then rotate handle portion 504a transversely to axis 501 about pin 518 to a position oriented about 90 degrees with respect to non-rotating portion 504b. Rotating handle portions 502a, 504a moves this portion of lamina spreader out of the way of the surgeon and avoids interference with other instruments to be inserted in the disc space.

It is contemplated that spreader 500 can be used to assist the surgeon in gaining access to the disc space. The rotating handles allow lamina spreader 500 to remain in place during subsequent procedures. It is further contemplated that the surgeon may not desire to use lamina spreader 500, and therefore proceed with disc space distraction after gaining access to the disc space.

Figure 4A:
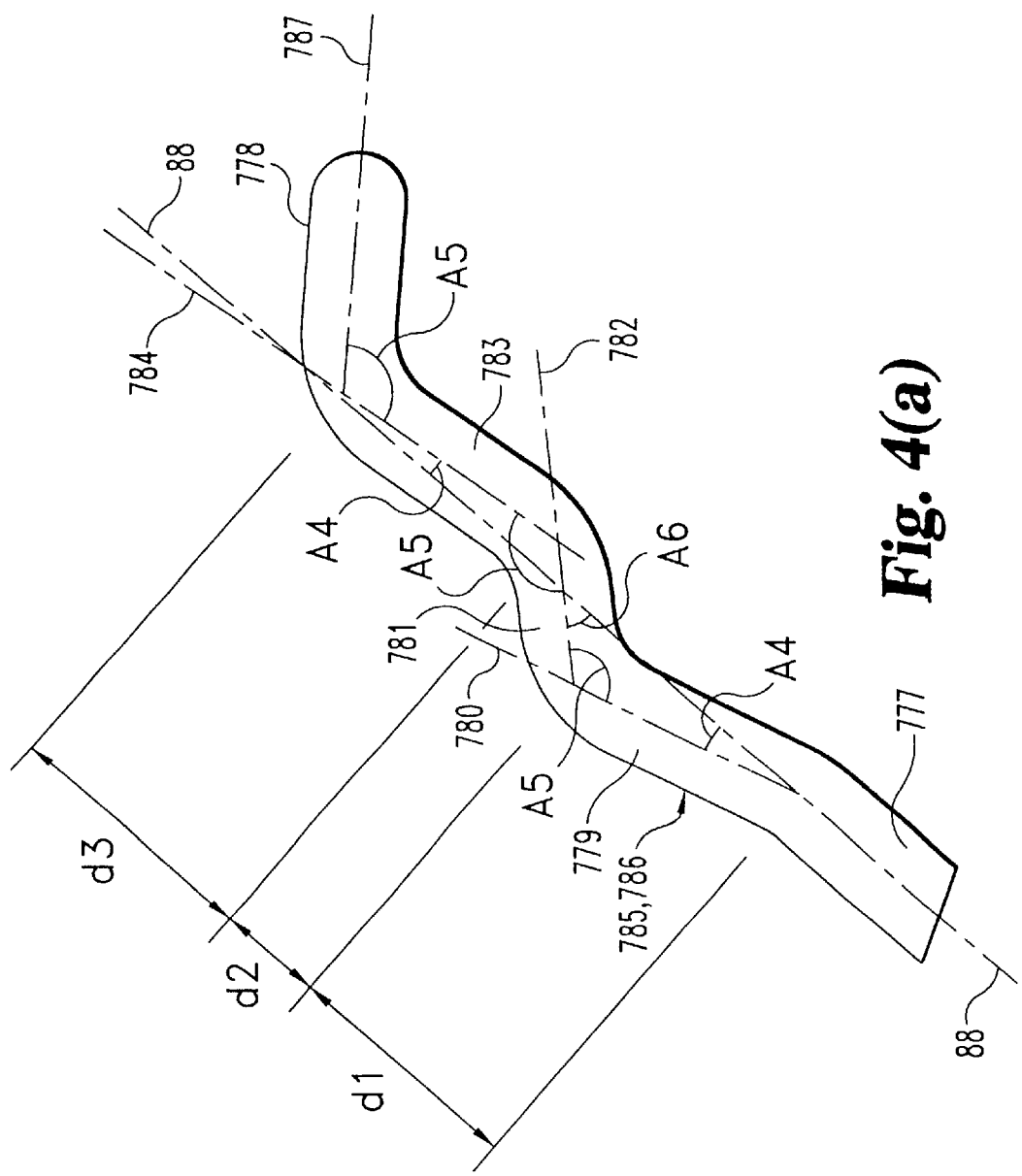
FIG. 4(a) is a plan view of the distal end of an alternate embodiment disc space spreader.

Referring to FIGS. 4 and FIGS. 5(a) and 5(b), a disc space spreader according to the present invention is shown. Disc space spreader 70 has a proximal portion that includes a first branch 72 pivotally joined to a second branch 74 by pin 76. Extending distally from pin 76 are distal portions 85 and 86 of branches 72 and 74, respectively. Distal portions 85 and 86 have a distal working end that includes spreading portions 80 and 78 that contact the endplates of the adjacent vertebrae to apply a distraction force thereto. Distal portions 85 and 86 further include lateral offset portions 81 and 79, respectively, that laterally offset the branches 72, 74 from the spreading portions 80, 78. Offset portions 79 and 81 have a straight portion extending generally parallel to central axis 88 extending between branches 72, 74 and a bend forming a first offset angle A2 with axis 88. Spreading portions 78 and 80 form a second overall offset angle A21 with axis 88. In a preferred embodiment, offset angle A2 is about 120 degrees, but it is contemplated that offset angle A2 can range from 90 degrees to 160 degrees. Offset angle A21 is about 110 degrees. The offset portions 79, 81 laterally offset branches 72, 74 from spreading portions 78, 80, allowing branches 72, 74 to be further pivoted across the spinous process S, as shown by disc space spreader 70 in FIG. 6, than would be possible without offset portions 79, 81. In one form, the lateral offset distance d between axis 88 and the center of the straight portion is between 10 to 20 millimeters. This allows the distal tip of spreader 70 to be properly oriented into posterior lateral opening 35 formed in disc space D1.

To separate spreading portions 78, 80 a force can be applied to the proximal ends of branches 72, 74. In a preferred embodiment, disc space spreader 70 includes a mechanism to force and/or maintain the separation of spreading portions 78 and 80. The spreading mechanism includes an externally threaded rod 82 pivotally joined to branch 72 and positionable in notch 83 formed in the proximal end of branch 74. The spreading mechanism has an internally threaded hand nut 84 threadedly received on rod 82. Branches 72 and 74 may be forced together by action of internally threaded nut 84 on branch 74 forcing it towards branch 72, thereby forcing spreading portions 78 and 80 apart. A spring blade 89 attached to branches 72, 74 biases branches 72, 74 apart.

Figure 6:
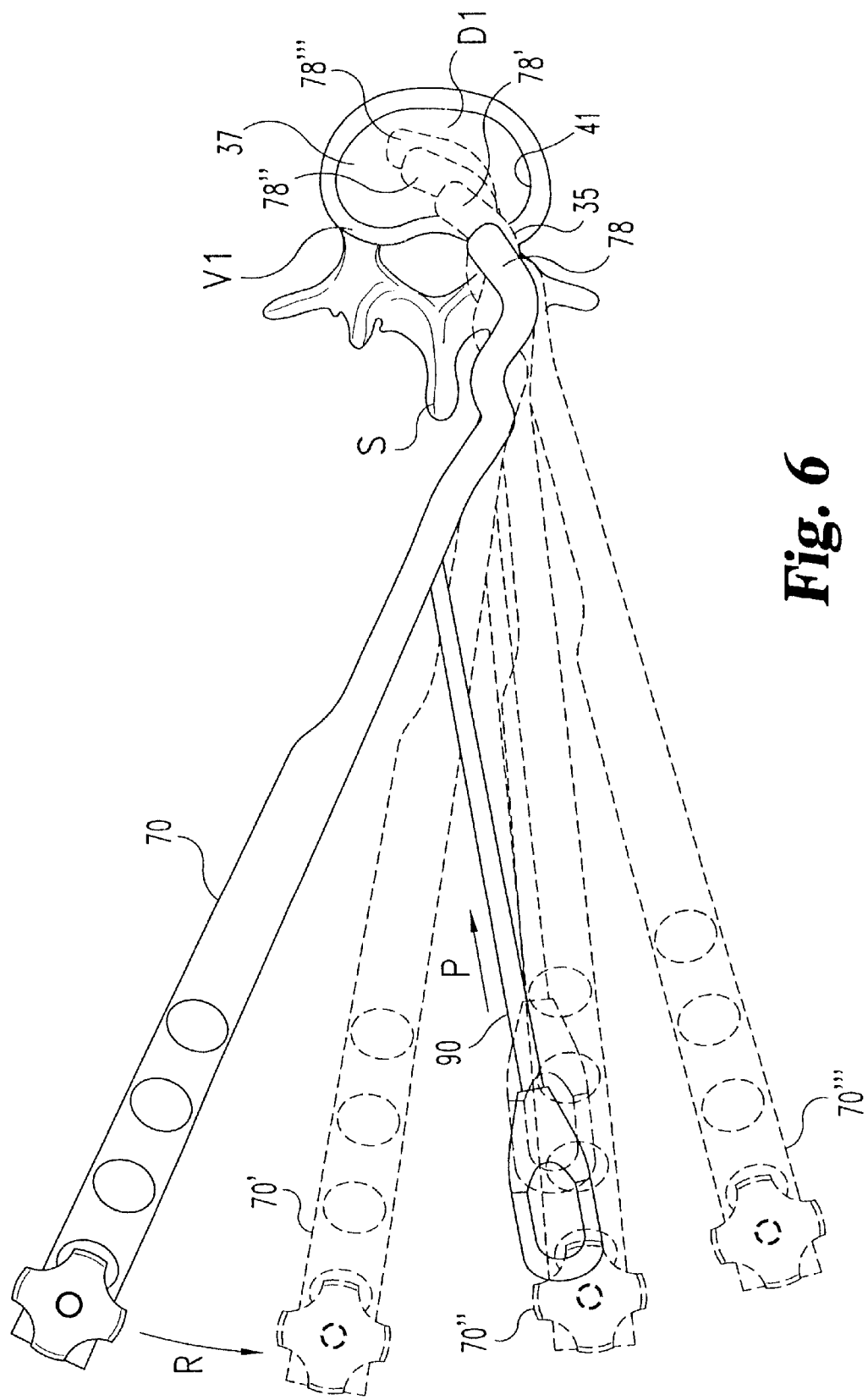
FIG. 6 shows the sequence of the insertion of the disc space spreader of FIG. 4 into a disc space.

Branches 72 and 74 also define opposing grooves 92 and 94 adjacent pin 76. A lever arm or pusher 90 may be provided having an elongated shaft 96 with a handle 98 on one end and an opposing spreader engaging portion 99. Engaging portion 99 is configured for removable engagement with opposing grooves 92 and 94 formed in branches 72 and 74, respectively. In se, removal of bony structures to gain access to the disc space and resection of disc material may be conducted by known methods. As shown in FIG. 6, the distal end of spreader 70 is positioned at opening 35, and pusher 90 can be used to provide a pushing force in the direction of arrow P into the disc space during the steps of inserting the spreading portions 78 and 80 into opening 35. Disc space spreader 70 is pivoted sequentially in the direction of arrow R about spinous process S via the proximal end of branches 72, 74. This pivotal and distal movement from proximal portion 41 to distal portion 37 of disc space D1 is indicated by the relative sequential positions of spreader 70, 70', 70", and 70''' and spreader portions 78, 78', 78", and 78'''. Thus, branches 72, 74 and pusher 90 enable the surgeon to have simultaneous two-handed control of spreader 70, with one hand controlling insertion movement with pusher 90 and the other hand controlling pivotal movement with branches 72, 74. This positions spreading portions 78, 80 across the disc space, and provides uniform disc space distraction so that the vertebral endplates will be parallel when distracted. The location of spreading portions 78, 80 in the disc space may be checked by any known visualization techniques before proceeding to tissue removal.

It should be understood that pusher 90 is engaged to disc space spreader 70 during the steps indicated by spreaders 70', 70" and 70''', but is not shown for purposes of clarity. The S-shaped connecting portions 79, 81 provide a lateral offset to branches 72, 74 to laterally offset branches 72, 74 from spreader portions 78, 80. This allows branches 72, 74 of disc space spreader 70 to avoid interference with the spinous process S when inserting the distal portions spreader portions 78, 80 through opening 35 into disc space D1. Enlarged stops (not shown) can be formed on distal portions 85 and 86 in order to engage the adjacent vertebra during insertion and limit advancement of spreaders 78 and 80 into disc space D1. After the spreader is inserted into the disc space, lever arm 90 may be removed.

Disc space spreader 70 is manipulated as described above to spread or distract disc space D1 to the desired height. In one procedure, it is contemplated that lamina spreader 500 is first used to spread the lamina. Since this tends to tilt the disc space and make the vertebral endplates non-parallel, spreader 70 can then be used to distract the distal portion of the disc space to provided parallel endplates. Disc space spreader 70 can remain in the disc space during subsequent procedures. It is further contemplated that lamina spreader 500, pedicle screw fixation with rods or plates on the other side of spinous process S may be used to maintain the distracted disc space height so that disc space spreader 70 can be removed. Distraction shims may also be used to maintain disc space distraction, such as disclosed in co-pending application entitled METHODS AND INSTRUMENTATION FOR DISTRACTION OF A DISC SPACE, filed Oct. 20, 1999, U.S. patent application Ser. No. 09/421, 709, which application is incorporated herein by reference in it entirety. In another form, lamina spreader 500 is not used by the surgeon, and the surgeon only uses disc space spreader 70 to restore the normal disc space height.

In FIG. 4(*a*) there is shown an alternate form for the distal portions of disc space spreader 70 which facilitates spreader insertion through opening 35. The proximal portion of the spreading instrument is similar to spreader 70 discussed above and will not be repeated here. Further, specific references are made to one alternate distal portion in this description, it being understood that the second distal portion is identical thereto. In addition, a spreader utilizing these alternate distal portions can be used in the same manner as discussed above with respect to disc space spreader 70. Central axis 88 between branches 72, 74 is provided in FIG. 4(*a*) to orient distal portions 785, 786 with respect thereto. Distal portions 785, 786 each have a distal working end that includes spreading portion 778 that contacts the endplate of the adjacent vertebrae to apply a distraction force thereto. Distal portions 785, 786 further include branch extension 777 extending from a respective one of the branches 72, 74 along axis 88.

A first lateral inset 779 extends from proximal portion 777 and has a central axis 780 forming an angle A4 with respect to axis 88 such that first lateral inset 779 extends in a first direction away from axis 88. A lateral offset 781 extends from first lateral inset 779 and has a central axis 781 forming an angle A6 with central axis 88 and an angle A5 with central axis 780 such that lateral offset 781 extends in a second direction with respect to axis 88 opposite the first direction, positioning the distal end of lateral offset 781 on the side of axis 88 opposite first lateral inset 779. A second lateral inset 783 extends from lateral offset 781 and has a central axis 784 forming an angle A5 with central axis 782 and an angle A4 with central axis 88 such that second lateral inset 783 extends in the first direction towards axis 88. Thus, first lateral insert 779 and second lateral inset 783 are parallel to one another. Spreading portion 778 extends from second lateral inset 783 in the second direction away from axis 88 and has a central axis 787 forming an angle A5 with central axis 88. Central axis 787 is not parallel to central axis 782 of lateral offset 781.

In one specific embodiment, it is contemplated that angle A4 is about 10 degrees, angle A5 is about 125 degrees and angle A6 is about 45 degrees. In this specific embodiment, the length d1 along central axis 88 of first lateral inset 779 is about 21 millimeters, the length d2 of lateral offset 781 along axis 88 is about 11 millimeters, and the length d3 of second lateral inset 783 along axis 88 is about 15 millimeters.

Figure 7:
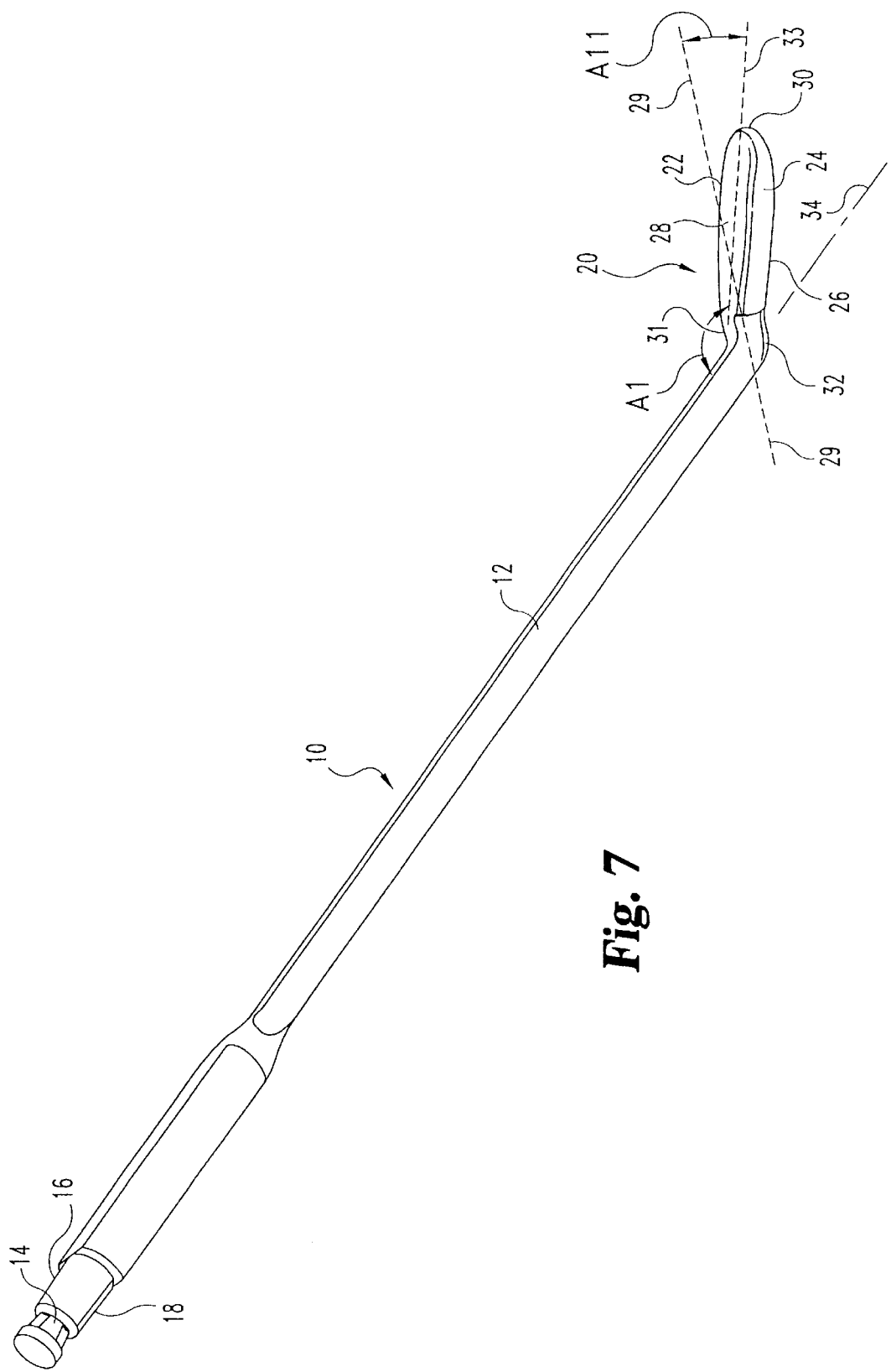
FIG. 7 is a perspective view of a distractor according to the present invention.

Referring now to FIG. 7, another alternate embodiment disc space spreader/distracting mechanism is shown. Distractor 10 includes an elongated shaft 12 having a longitudinal axis 34. On the proximal end, distractor 10 includes a tool coupling 14 having a pair of opposed driving surfaces 16 and 18. On the opposite distal end, distractor 10 includes a distraction head 20 with a straight section 31 joined to shaft 12 by bend 32. Straight section 31 has a longitudinal axis 29 disposed at an angle A1 with respect to longitudinal axis 34. In a preferred embodiment angle A1 is between 120 and 160 degrees. Distraction head 20 is joined to straight section 31 and has a longitudinal axis 33 at an angle A11 with respect to axis 29. In one embodiment, angle A11 is between 20 and 60 degrees. Distraction head 20 includes a pair of opposed distraction flats 26 and 28 separated by a first height. A second pair of opposed flats 22 and 24 is separated by a second height, the second height being greater than the first height.

Figure 8:
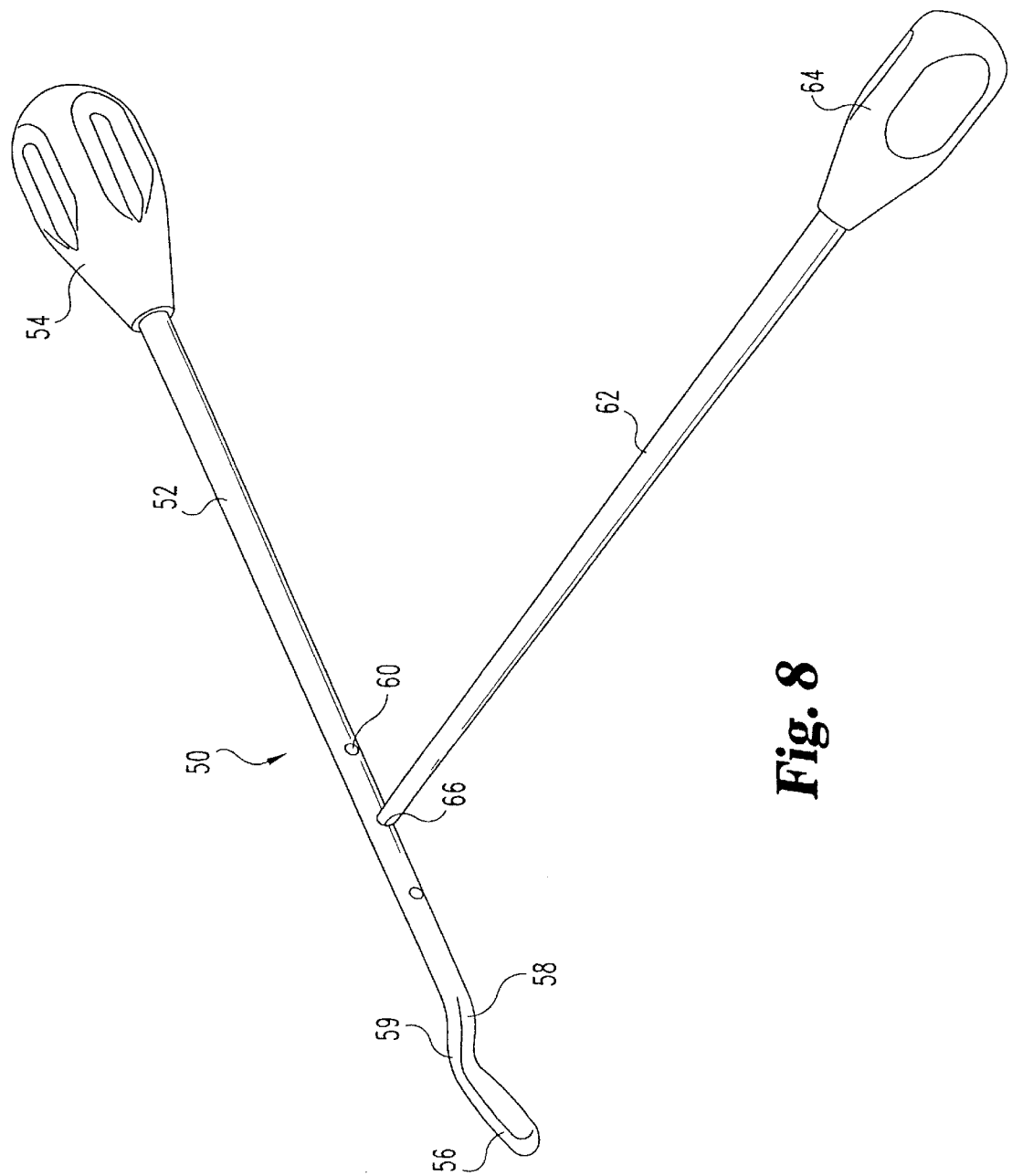
FIG. 8 is a perspective view of an alternative distractor having application in the present invention.

In an alternative embodiment to distractor 10 shown in FIG. 8, distractor 50 may include a lever arm 62 to assist in rotation of the distractor head after insertion into the disc space. Distractor 50 includes a shaft 52 having a handle 54 opposite distractor head 56. As with the previous embodiment, distractor head 56 is joined to shaft 50 a lateral offset that includes a bend 58 and a straight section 59. Additionally, shaft 53 includes multiple holes 60, which preferably include an internal thread. Lever arm 62 has a connection end 66 adapted to be removably received in a selected one of the holes 60. Handle 64 tends to allow the surgeon to generate a substantial torque on head 56 to rotate head 56 in the disc space.

Figure 9:
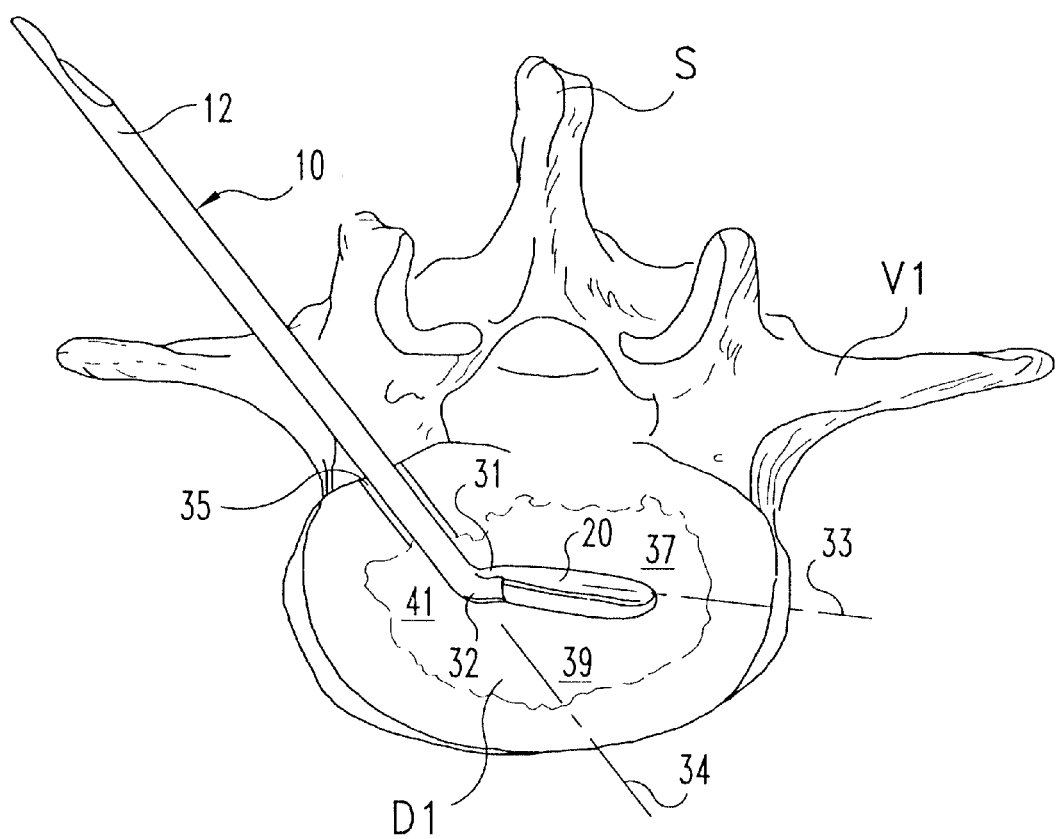
FIG. 9 is a top plan view of a vertebra with the distractor of FIG. 7 inserted in the disc space.

Referring to FIG. 9, distractor 10 may be utilized to distract adjacent vertebrae. Distractor head 20 may be inserted into disc space D1 through opening 35. Distractor head 20 may be inserted into the disc space D1 until the distal tip is positioned adjacent the distal portion 37 and straight section 31 is disposed in disc space D1 adjacent proximal portion 41. Distractor 10 is oriented during insertion in a reduced height configuration such that surface 26 of head 20 engages the endplate of vertebra V1. In a similar manner, surface 28 engages upper adjacent vertebra V2. Thus, distractor head 20 creates a distraction height approximating the distance between surfaces 26 and 28. Distractor shaft 12 is then moved to cause rotation about axis 33 of the distraction head 20 bringing surfaces 22 and 24 into contact with the opposing endplate surfaces, thereby distracting the disc space to the second, greater height between surfaces 22, 24. Lamina spreader 500, pedicle screw fixation with rods or plates may be used to maintain disc space height. Distraction shims may also be used to maintain disc space distraction.

Figure 13:
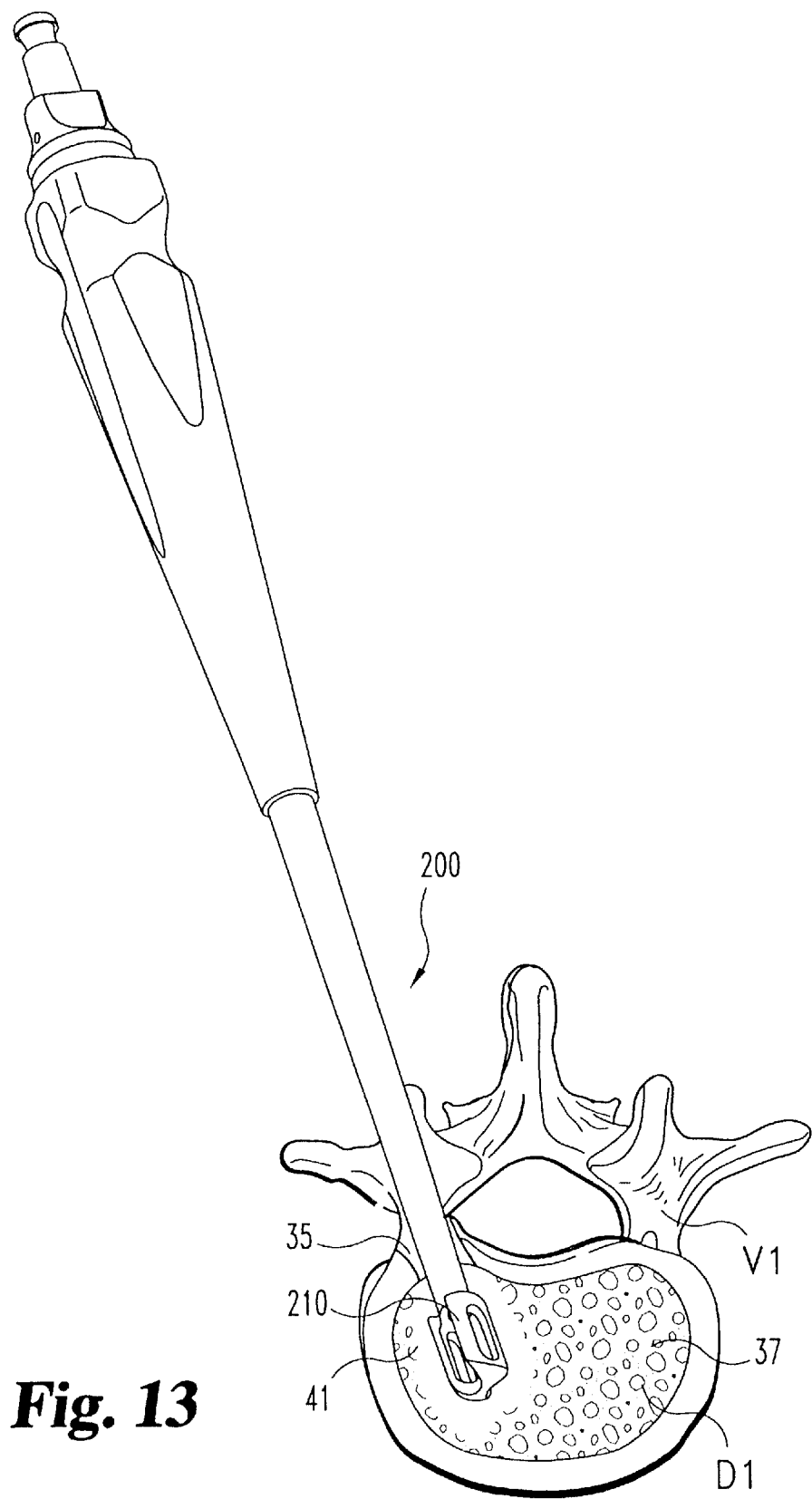
FIG. 13 is a top plan view of a vertebra with the straight reamer of FIG. 10 inserted in the disc space.

According to a further aspect of the invention, various reamers are provided with the present invention to remove soft tissues from the disc space and the cartilage layer from the adjacent vertebral endplates. A straight reamer is illustrated in FIG. 10 and a curved reamer is illustrated in FIG. 11. Straight reamer 200 includes a hollow outer shaft 202 with a handle 204 attached to the proximal portion thereof. A rotatable inner shaft 206 is disposed within outer shaft 202. Rotary cutting head 210 having a cavity 213 is coupled to inner shaft 206. A Hudson type tool coupler 208 is provided at the proximal portion of inner shaft 206. It will be understood that a manual handle, such as a T-handle, may be attached to tool coupler 208. Application of rotation force on the inner shaft turns cutting head 210. Straight reamer 200 is inserted through opening 35 to remove material from proximal portion 41 of disc space D1, as shown in FIG. 13. Cutting head 210 of curved reamer 200 may be moved to various locations in the proximal portion 41 of disc space D1 and the cutting head reinserted to widen or alter a previously formed channel. A powered rotary driver may also be coupled to tool coupler 208 to mechanically drive inner shaft 206 and rotate cutting head 210.

Figure 14:
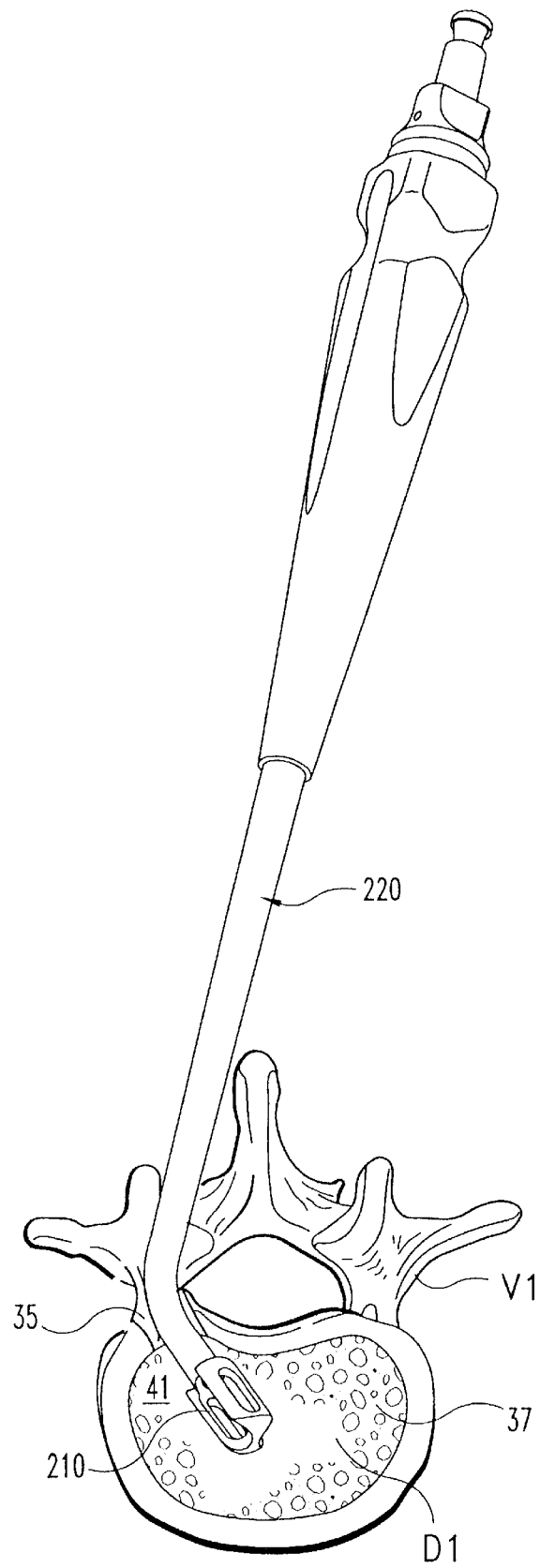
FIG. 14 is a top plan view of a vertebra with the curved reamer of FIG. 11 inserted in the disc space.

Referring now to FIG. 11, curved reamer 220 includes a hollow outer shaft 222 with a handle 224 attached to the proximal portion thereof. A rotatable inner shaft 226 is disposed within outer shaft 222. Rotary cutting head 210 (identical to the head provided on reamer 200) having a cavity 213 is coupled to inner shaft 206. Outer shaft 222 includes a bend 221 angled at offset angle A3, permitting insertion of cutting head 210 through opening 35 and into distal portion 37 of disc space D1, as shown in FIG. 14. It is contemplated that A3 may range from 100 to 150 degrees. In one specific embodiment, angle A3 is about 125 degrees. Further, while a fixed bend is shown for the purpose of illustration in FIG. 11, it is contemplated that outer shaft 222 may include a flexible portion or mechanical coupling permitting a plurality of angles for bend 221. Inner shaft 226 is preferably flexible at least through bend 221 so that rotary torque can be transmitted through bend 221. The flexible inner shafts used with the instruments of the present invention can be made from, for example, stainless steel coiled wire or nitinol.

A Hudson type tool coupler 228 is provided at the proximal portion of inner shaft 226. It will be understood that a manual handle, such as a T-handle, may be attached to tool coupler 228 to permit application of rotation force on the inner shaft and turn cutting head 210. Alternatively, a powered rotary driver may be coupled to tool coupler 228 to mechanically drive inner shaft 226 and rotate cutting head 210. As shown in FIG. 14, cutting head 210 of curved reamer 220 may be moved to various locations in the distal portion 37 of disc space D1 and the cutting head reinserted to widen or alter a previously formed channel. Thus, straight reamer 200 and curved reamer 220 allow the surgeon to remove disc material, cartilage and other tissue in both proximal portion 41 and distal portion 37 of disc space D1 through opening 35.

As shown in FIG. 12, cutting head 210 includes cutting edges 211a, 211b, 211c, and 211d. Cutting head 210 has a smooth, non-cutting profile between edges 211a, 211d and between edges 211b, 211c. It is contemplated that head 210 is inserted with the non-cutting profiles oriented towards the vertebral endplates to provide smooth insertion and positioning of cutting head 210 in the disc space. The location of cutting head 210 in the disc space may be checked by any known visualization techniques before proceeding to tissue removal. When cutting head 210 is rotated in direction R1, edges 211a and 211c cut tissue and cartilage, while edges 211b and 211d pass over the tissue without cutting. The cut material is deposited in cavity 213, where it may then be extracted from the disc space. Cutting head 210 provides a safe and efficient discectomy tool that preserves the bony endplate surface and quickly collects the soft tissue.

Other embodiments of cutting instruments are provided that include a guide member for controlled cutting within the proximal and distal portions of the disc space. Referring to FIGS. 15 and 16, a guided rotary cutter is disclosed. Cutter 100 includes a guiding shaft 102 having an interconnected handle 109 disposed on the proximal end and a stop 106 disposed on the opposing distal end. Stop 106 may be substantially radiopaque to provide an indication of inner shaft location on x-ray images. Distal portion 103 is joined to shaft 102 by bend 104. Bend 104 is preferably a substantially uniform curve creating angle A3 between axis 105 of shaft 102 and axis 107 of distal portion 103.

Disposed on guide shaft 102 between handle 109 and stop 106 is an outer shaft 108. Outer shaft 108 includes a handle 110 on a proximal end and a flexible drive 112 on the opposing distal end. A cutting head 114 is interconnected with flexible drive 112. As shown more clearly in FIG. 16, cutting head includes a number of cutting blades configured for rotary cutting. Flexible drive 112 is designed to transmit both longitudinal force to advance cutting head along guiding shaft 102 in the direction arrow 116 and also transmit rotation force in the direction of arrow 118 to move cutting head 114 in a circular manner about shaft 102, thereby engaging cutting blades 120 with adjacent tissues. While other flexible drives, such as, for example but without limitation, cables and mechanical couplings may be utilized, in a preferred embodiment flexible drive 112 is a helically wound cable.

Figure 17:
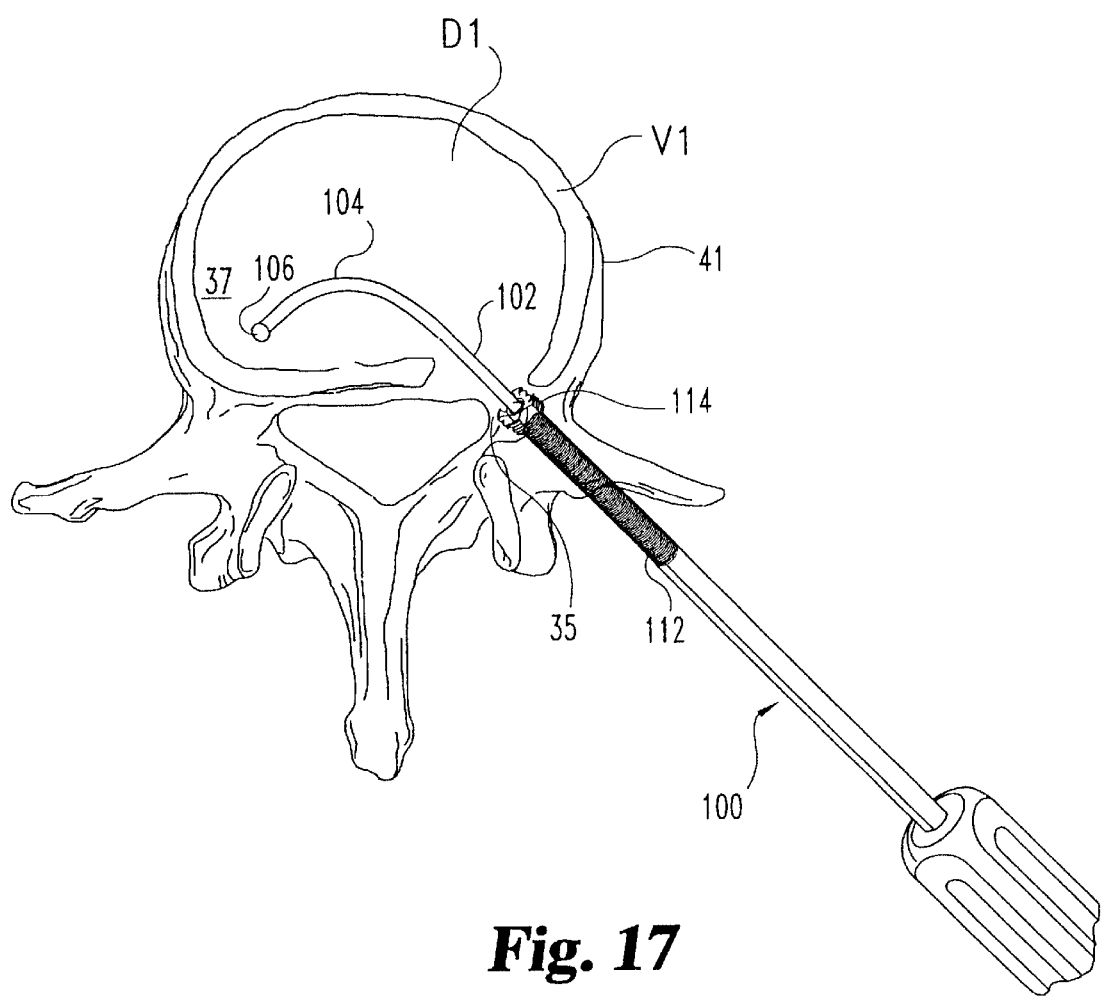
FIG. 17 is a top plan view of a vertebra with the cutter of FIG. 15 inserted in the disc space.

Referring to FIG. 17, cutter 100 may be inserted into disc space D1 through opening 35. Preferably, stop 106 is positioned adjacent distal disc space portion 37 and bend 104 may be positioned centrally in the disc space. The location of guide shaft 102 in the disc space may be checked by any known visualization techniques before proceeding to tissue removal. Once the proper positioning of the guide shaft 102 has been established, force is applied to handle 110 to advance cutting head 114 into contact with structures adjacent the disc space. Forward pressure in the direction of arrow 116 may be maintained as rotational force in the direction of arrow 118 is transmitted to cutting head 114. As tissue is removed cutting head 114 may cuttingly advance along guide shaft 102 until it reaches stop 106. Cutting head 114 has an internal channel (not shown) sized to receive shaft 102 but limited in size and shape such that the cutting head may not extend beyond stop 106. As will be understood by the illustrations, cutting tool 100 forms an arcuate channel through the disc space by following guiding shaft 102. Guide shaft 102 may be moved to one or more new locations in the disc space and the cutting head reinserted to widen or alter a previously formed channel in disc space D1.

Figure 20:
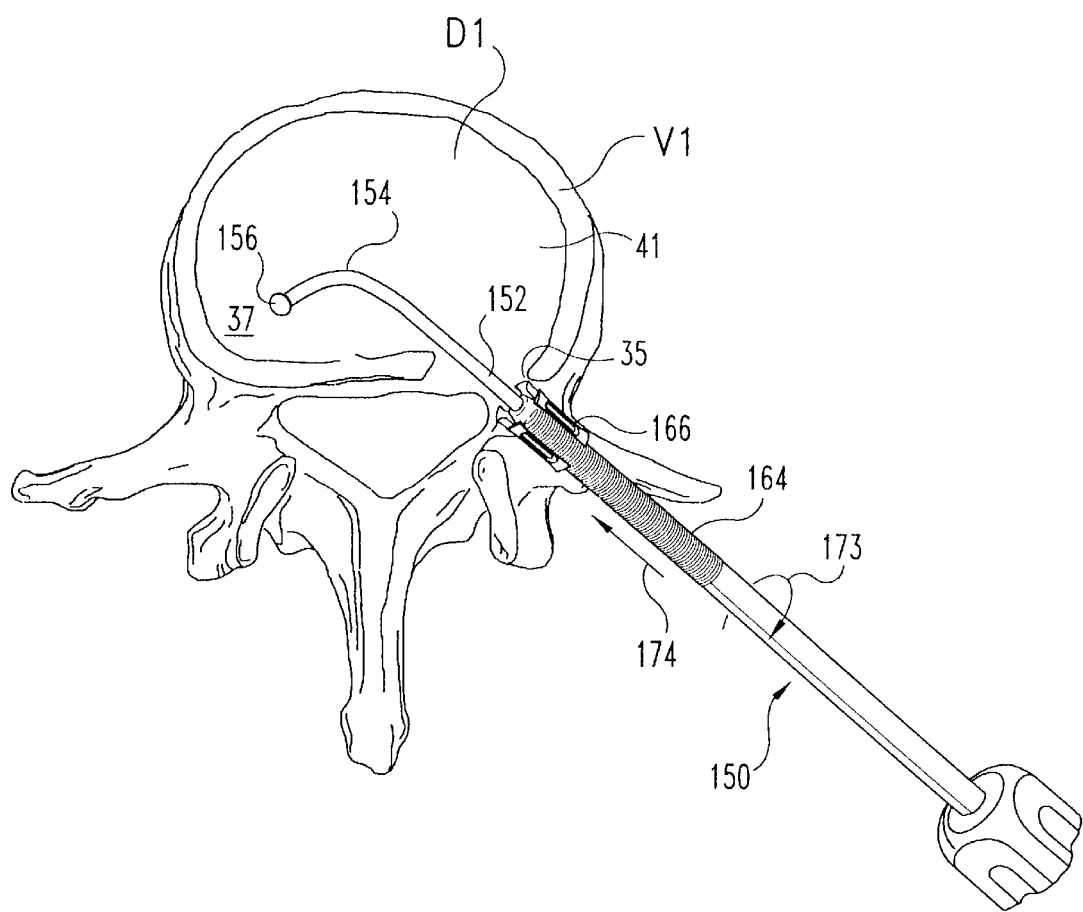
FIG. 20 is a top plan view of a vertebra with the cutting tool of FIG. 18 in the disc space.

A further embodiment of a rotary cutting device is disclosed in FIGS. 18 through 20. Shaver 150 includes a guide rod 152 with a handle 158 disposed at the proximal end and a stop 156 disposed on the distal end. Guide rod 152 includes bend 154 adjacent the distal end. Outer shaft 160 is slidably mounted on guide rod 152. Outer shaft 160 includes a handle 162 on its proximal end and is coupled to flexible drive 164 on its distal end. A shaving head 166 is mounted on flexible drive 164. Preferably, shaving head 166 has a plurality of cutting blades adapted to shave tissue as the head is rotated. In one aspect, individual blades of head 166 are elongated and include a forward cutting blade 168 and backward cutting blade 170 and a cavity 169 for deposit of material. Still more preferably, shaving head 166 has sufficiently flexibility to allow it to conform at least partially to bend 154 as it is advanced along guide rod 152 towards stop 156.

In use, shaver 150 may be positioned in disc space D1 with stop 156 disposed adjacent distal disc space portion 37 as shown in FIG. 20. Preferably, shaver 150 will follow use of cutter 100 to further define and expand the arcuate channel defined in the disc space. As shaver head 166 is advanced in the direction of arrow 174, handle 162 may be rotated thereby rotating head 166 in the direction of arrow 173 to cut tissue, and cut tissue can be accumulated between the blades and in cavities 169 for removal from disc space D1. Shaver head 166 preferably cuts in both directions, however it is also contemplated that the shaver may be unidirectional.

Figure 21:
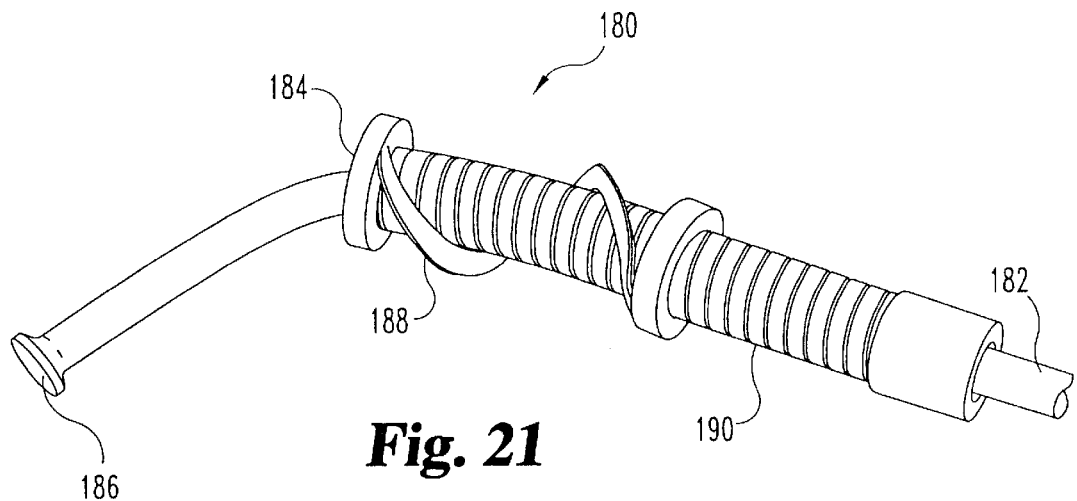
FIG. 21 is a perspective view of an alternative cutting tool head.
Figure 22:
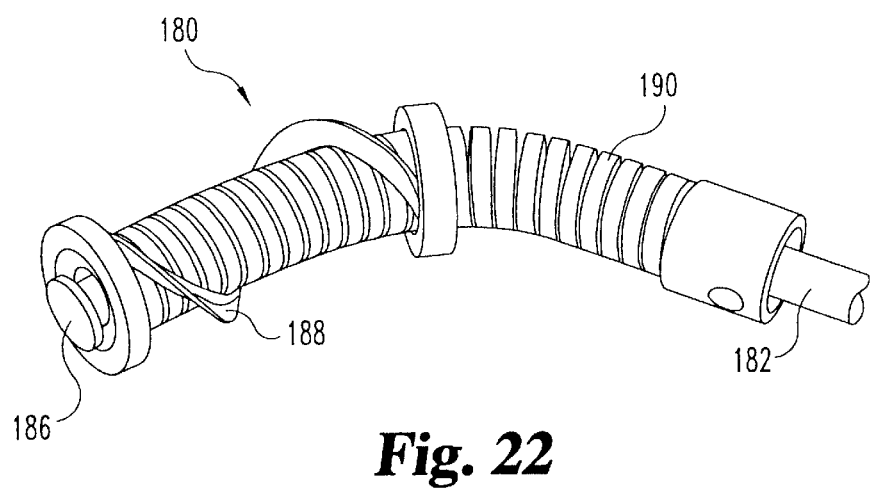
FIG. 22 is a further perspective view of the cutting tool head of FIG. 21.

Referring now to FIGS. 21 and 22, an alternative shaver head 180 is illustrated. Shaver head 180 is slidably disposed on inner shaft 182 and may be advanced along the shaft until it reaches stop 186. Shaver head 180 includes a flexible drive portion 190 and a helical cutting blade 188 disposed on the distal portion of the flexible drive. Thus, as flexible drive 190 rotates, helical blade 188 cuts the tissue and accumulates tissue between the blades for removal from the disc space.

Figure 23A:
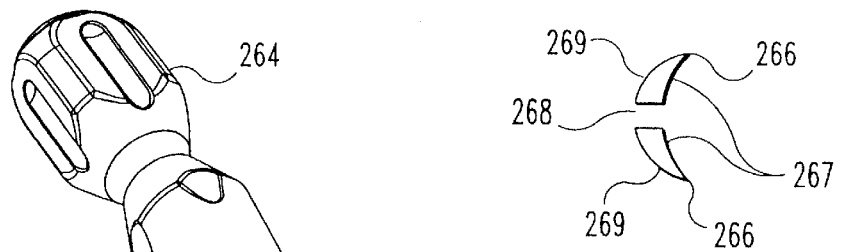
FIG. 23(a) is section view taken through line 23(a)—23(a) of FIG. 23.
Figure 23:
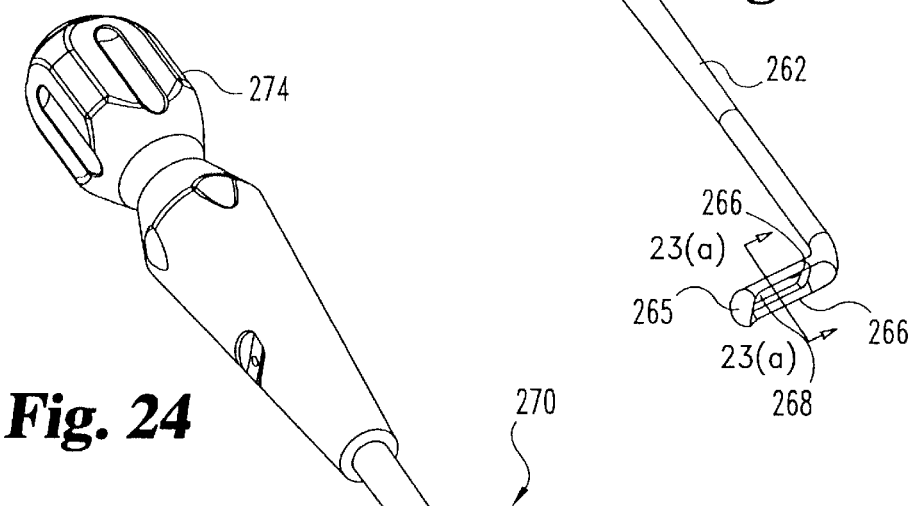
FIG. 23 is a perspective view of a push scraper according to the present invention.
Figure 24A:
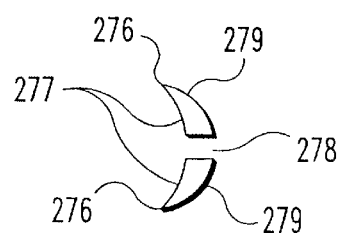
FIG. 24(a) is section view taken through line 24(a)—24(a) of FIG. 24.
Figure 24:
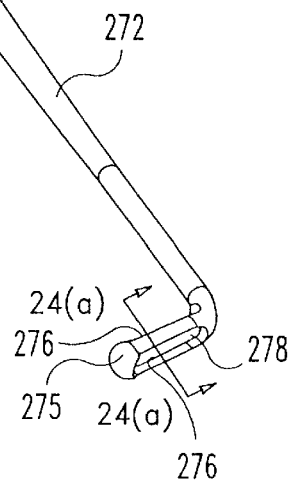
FIG. 24 is a perspective view of a pull scraper according to the present invention.
Figure 25:
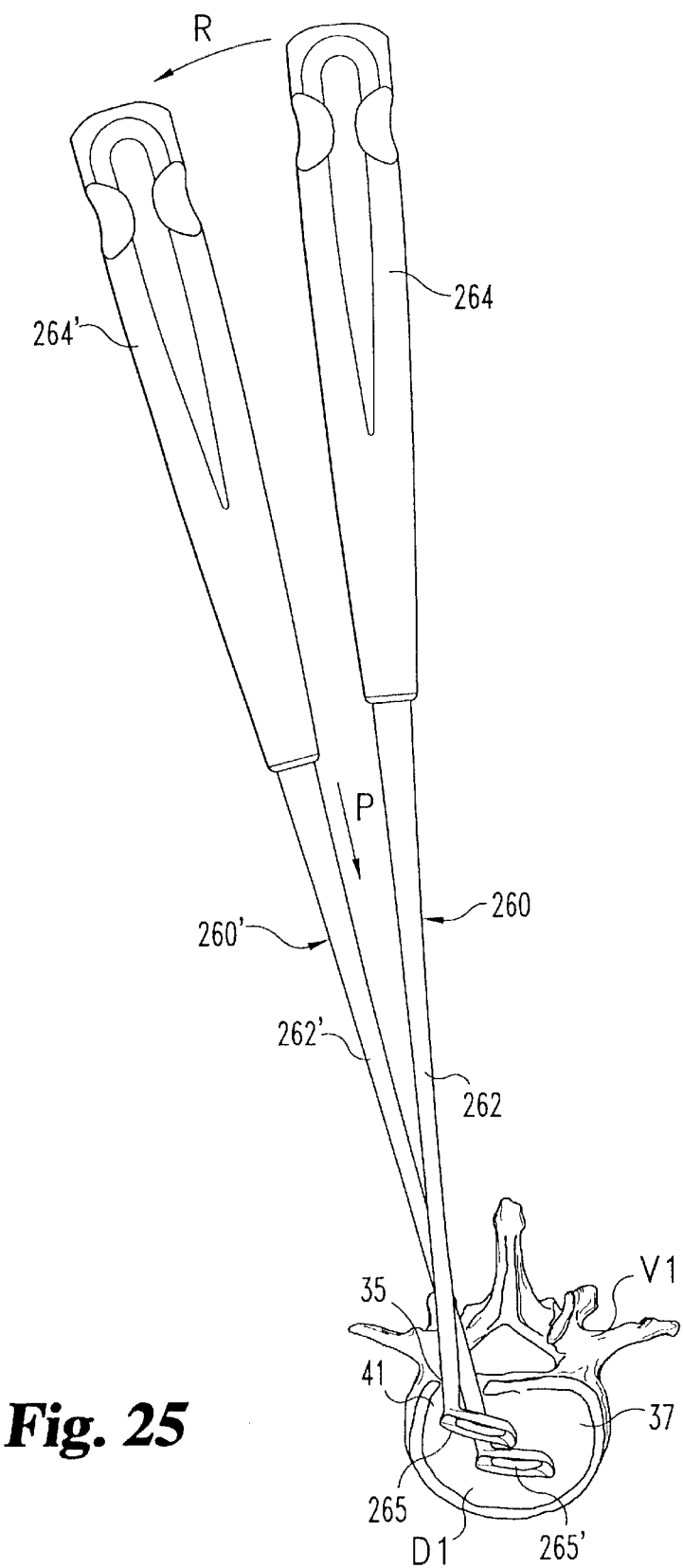
FIG. 25 is a top plan view of a vertebra with the push scraper of FIG. 23.

Referring to FIGS. 23–26, further cutting instruments according to the present invention are shown. In FIG. 23 there is illustrated a push scraper 260. Push scraper 260 includes an elongated shaft 262 with a handle 264 on the proximal end and a push scraper head 265 on the distal end. Scraper head 265 is joined to and is substantially perpendicular to shaft 262. As shown in FIG. 23(a), scraper head 265 includes distally facing upper and lower cutting blades 266 having a distal concave face 267 with a hole 268 formed therein. Concave face 267 forms a trough around hole 268. The proximal face 269 of scraper head 265 has a smooth, convex non-cutting profile to facilitate proximal movement of scraper head 265 through the disc space. As shown in FIG. 25, push scraper 260 is inserted through opening 35 with scraper head 265 initially positioned towards proximal portion 41 of disc space D1. Push scraper 260 is then pivoted and pushed distally through disc space D1, as indicated by push scraper 260', to position scraper head 265' towards distal portion 37 of disc space D1. Distally facing blades 266 remove disc material and can deposit at least some of the material in the trough between blades 266 during this distal pivotal movement for subsequent removal. A pusher as described herein can be used to facilitate this distal pivotal movement.

Figure 26:
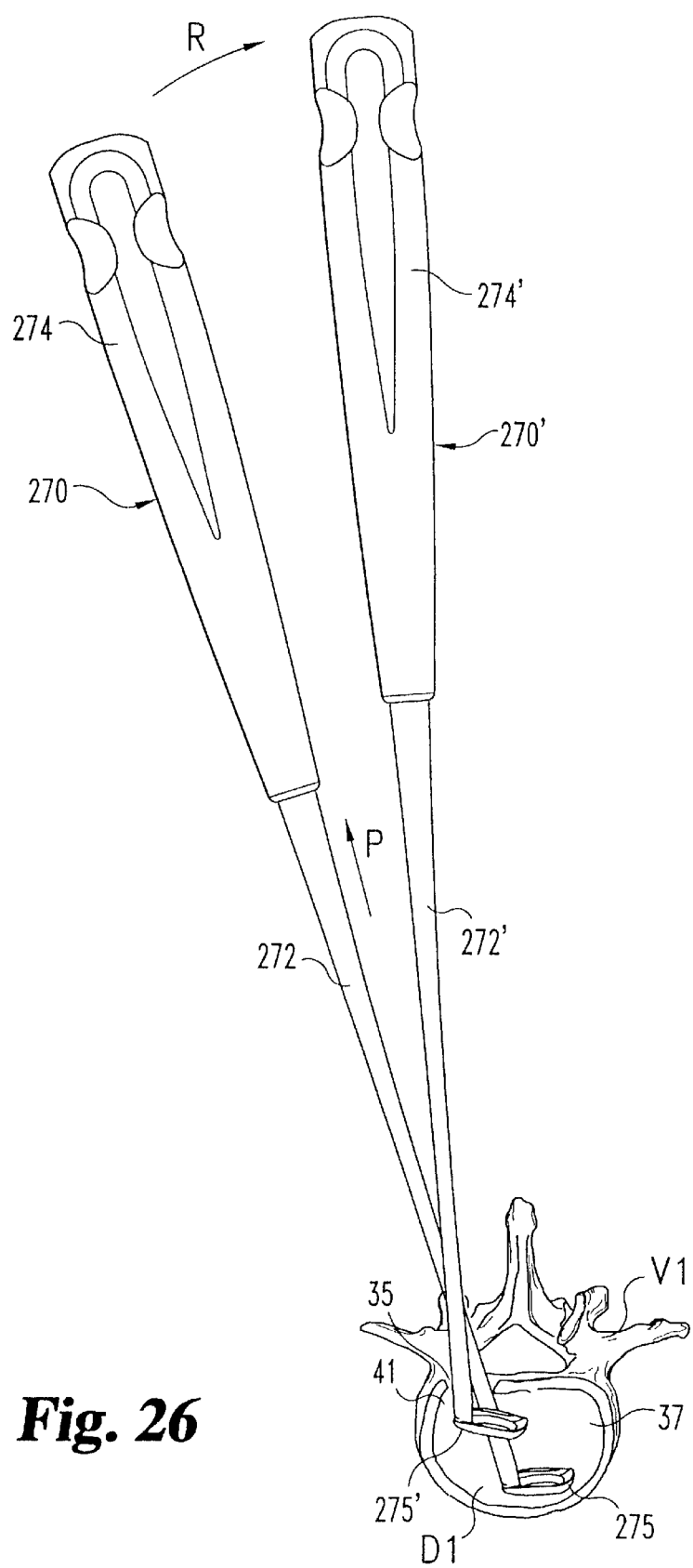
FIG. 26 is a top plan view of a vertebra with the pull scraper of FIG. 24.

In FIG. 24 there is illustrated a pull scraper 270 includes an elongated shaft 272 with a handle 274 on the proximal end and a pull scraper head 275 on the distal end. Scraper head 275 is joined to and extends substantially perpendicular to shaft 272. Scraper head 275 includes proximally facing cutting blades 276 and a concave proximal face 277 with a hole 278 formed therein. Concave face 277 forms a trough around hole 278. The distal face 279 of scraper head 275 has a smooth, convex non-cutting profile to facilitate distal movement of scraper head 275 through the disc space. As shown in FIG. 26, pull scraper 270 is inserted through opening 35 and scraper head 275 is pushed through disc space D1 to initially position scraper head 275 towards distal portion 37 of disc space D1. Pull scraper 270 is then pivoted and pulled proximally through disc space D1, as indicated by pull scraper 270', to position scraper head 275' towards proximal portion 41 of disc space D1. Proximally facing blades 276 remove any remaining disc material and can deposit at least some of the material in the trough between blades 276 during this proximal pivotal movement for subsequent extraction.

Figure 27:
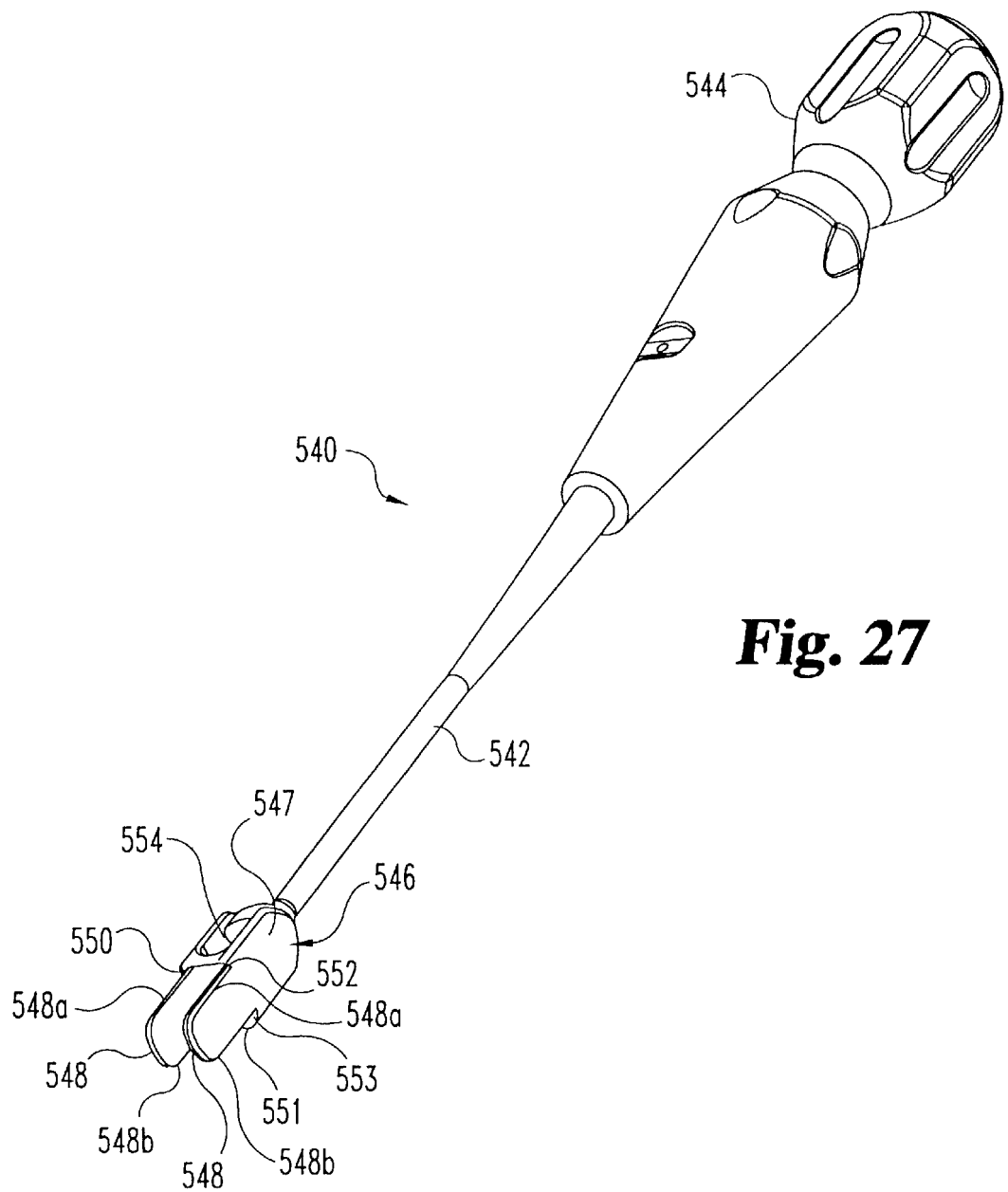
FIG. 27 is a perspective view of a straight chisel according to the present invention.

When the desired amount material has been removed from disc space D1 using the instruments described above, a straight chisel 540 as shown in FIG. 27 is provided for preparing a square entrance port into disc space D1 for implant insertion. Chisel 540 includes shaft 542 having a handle 544 coupled to the proximal end of shaft 542. A chisel head 546 is provided at the distal end of shaft 542. Chisel head 546 includes a body portion 547 having a pair of non-cutting extensions 548 extending distally therefrom. Extensions 548 have an upper surface 548a for contacting vertebra V2 and a lower surface 548b for contacting lower vertebra V1. Extensions 548 guide chisel head 546 into the disc space, ensuring equal amounts of material are removed from the endplates of the upper and lower vertebrae by upper cutting edge 550 and lower cutting edge 551. V-shaped portions 552, 553 distally offset edges 550, 551, respectively, with respect to body portion 547. A chamber 554 is formed in body portion 547, and body portion 547 has upper and lower openings positioned proximally of the upper and lower cutting edges 550, 551. Cut material can be deposited through these upper and lower openings and into chamber 554.

Figure 28:
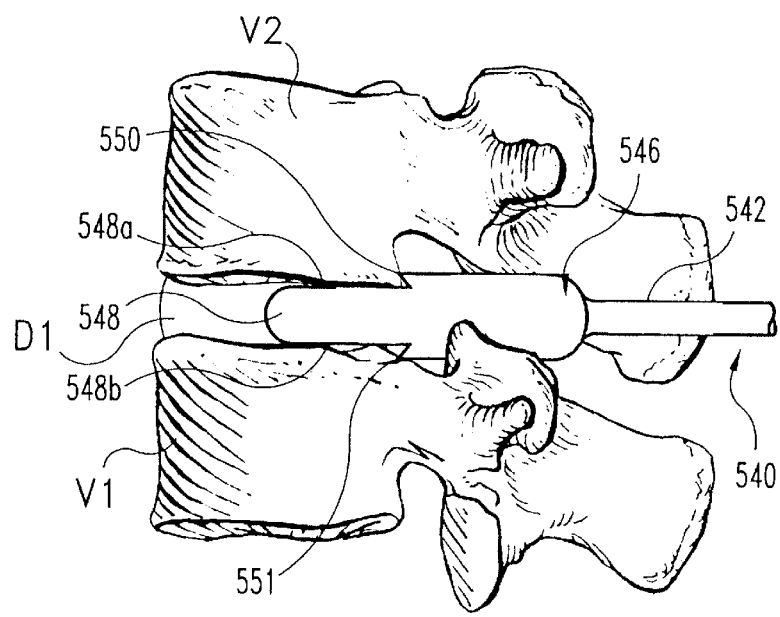
FIG. 28 is a lateral elevational view of a spinal column segment with the chisel of FIG. 27 inserted in the disc space.
Figure 29:
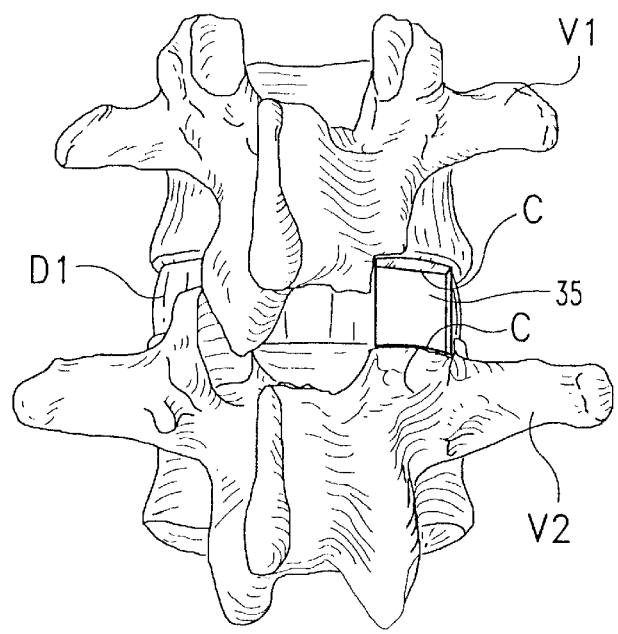
FIG. 29 is a posterior elevational view of a spinal column segment showing the disc space entrance created by the chisel of FIG. 27.

Referring now to FIG. 28, chisel 540 is shown with extensions 548 in disc space D1. Chisel head 546 is impacted into the disc space, with cutting edges 550, 551 removing bone material and osteophytes from the vertebral endplates. This provides, as shown in FIG. 29, an enlarged squared entrance to disc space D1 is formed at the proximal portion of the disc space that is larger than the opening created by spreading the lamina and distracting disc space D1. This enlarged entrance facilitates implant insertion into the disc space. The material removed to form the enlarged entrance is indicated by cut-away portions C in vertebra V1 and V2.

Figure 32:
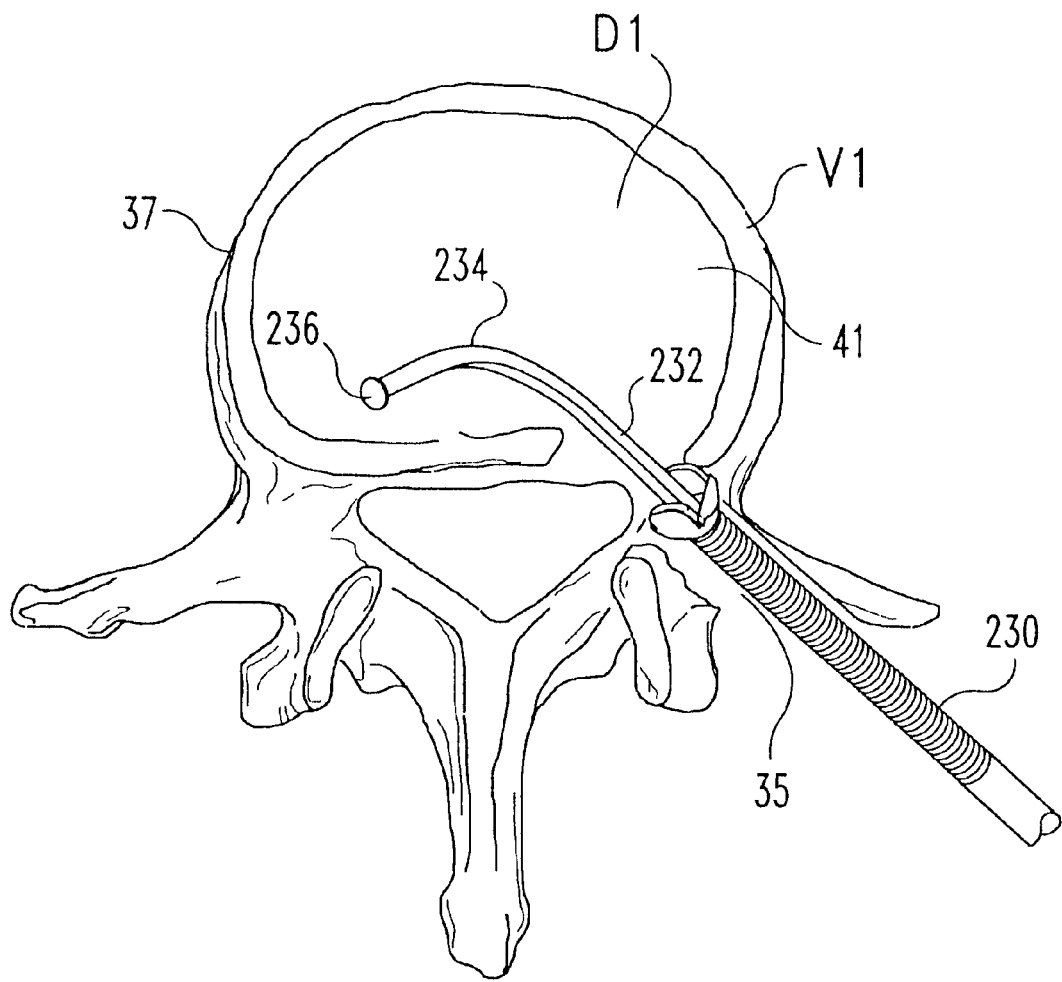
FIG. 32 is a top plan view of a vertebra with the chisel of FIG. 30.

Referring now to FIGS. 30 through 32, there is shown a guided chisel which can be used, if desired, to remove material from distal portion 37 of disc space D1. Chisel 230 includes an inner shaft 232 with a handle 238 connected to the proximal end and a stop 236 formed on the distal end. As shown in FIG. 31, inner shaft 232 preferably has a non-circular cross section 233 adjacent the distal portion. The non-circular cross section, preferably square, inhibits rotation of the chisel cutting head as it is impacted along inner shaft 232. Outer shaft 240 is slidably disposed about inner shaft 232. Outer shaft 240 includes a drive region 242 with an impact shoulder 244. Outer shaft 232 is coupled to chisel head 248 by flexible drive 246. Chisel head 248 includes an upper cutting edge 254 and a lower cutting edge 252. The cutting blades are spaced by extensions 249 and 251 that control and limit the depth of penetration of the cutting edged into the endplates.

As shown in FIG. 32, inner shaft 234 is positioned in disc space D1 through opening 35. Stop 236 is position adjacent the distal portion 37 of disc space D1. Visualization of the placement of inner shaft 234 may be made to confirm proper positioning. Once the position in confirmed, chisel head 248 is advanced along inner shaft 232 in the direction of arrow 250. If necessary, a forked slap hammer or pusher may be positioned with the forks extending on either side of drive region 242. The slap hammer may then be forcibly urged against impact shoulder 244 to drive chisel head 248 into the disc space. The chisel head is advanced until it engages stop 236. This action forms a substantially square or rectangular arcuate channel extending into each of the adjacent vertebral endplates.

Referring now to FIGS. 33 through 34 there is provided an implant template inserter 560 according to another aspect of the present invention. Template inserter 560 includes a shaft 562 having a handle 564 detachably secured to the proximal end of shaft 562. A bend 566 is secured to the distal end of shaft 562 and forms offset angle A3. A template 568 is secured at the distal end of bend 566. A notch 567 is provided in shaft 562 that is engageable by a pusher, such as pusher 670 described below, to facilitate placement of template 568 into disc space D1. Template 568 is positionable through opening 35 into the distal portion of disc space D1 to determine if enough material has been removed from the disc space to accommodate the implant to be inserted therein, or to determine the size of implant required. Handle 564 is removable for fluoroscopic or radiographic imaging of template 568 in disc space D1, allowing the surgeon to confirm the fit and positioning of template 568 in disc space D1. Templates 568 of various heights h1 having various sized bends 566 can be provided so the surgeon can perform multiple trials to obtain information as to the proper implant size.

Figures 35, 35A:
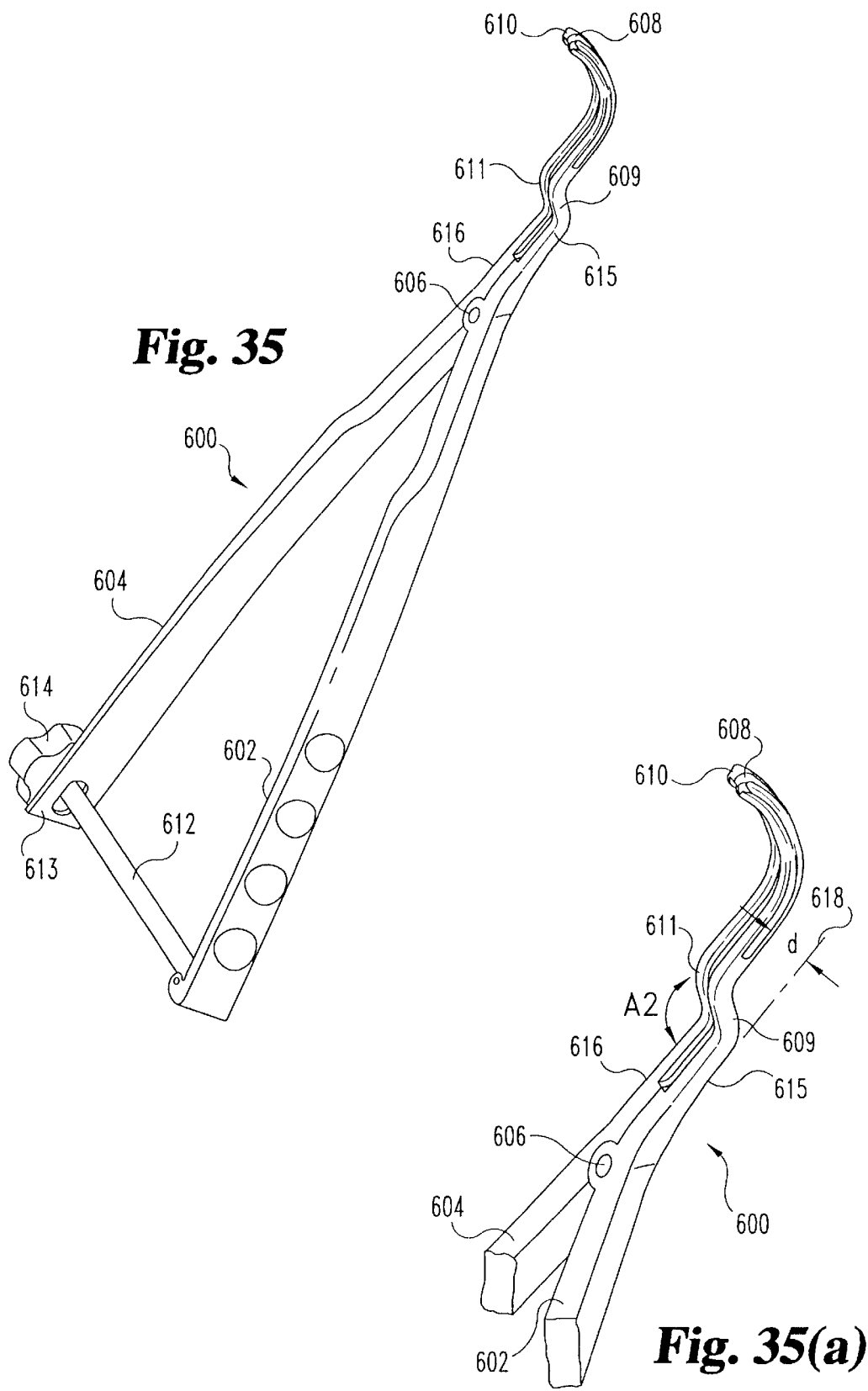
FIG. 35 shows a perspective view of an implant insertion guide according to the present invention.
FIG. 35(a) is an enlarged view of the distal end portion of the implant insertion guide of FIG. 35.

Referring now to FIGS. 35 and 35(a), there is shown an implant insertion guide 600 according to another aspect of the present invention. Insertion guide 600 has a proximal portion that includes a first branch 602 pivotally joined to a second branch 604 by pin 606. Extending distally from pin 606 are distal portions 615 and 616 of branches 602 and 604, respectively. Distal portions 615 and 616 have a distal working end that includes guide members 608 and 610 extending from lateral offsets 609 and 611, respectively. Offset portions 609 and 611 have a straight portion extending generally parallel to and offset by distance d from axis 618, and a bend forming a first offset angle A2 with axis 618. Guide members 608 and 610 have an arcuate form extending from offset portions 609, 611 to the distal tip insertion guide 600. This shape generally corresponds to the shape of the implant insertion path P, as discussed below. Guide members 608, 610 preferably have a length and shape such that the distal tip of inserter guide 600 is positionable in the desired location in distal portion 37 of disc space D1. These offset portions 609, 611 laterally offset branches 602, 604 from guide members 608, 610. This provides room for placement of an implant insertion instrument, such as those described below, or the implant template inserter 560 described above, alongside branches 602, 604. The implant can be slid along guide members 608, 610 and into the disc space, and guide members 608, 610 provide a barrier that protects the anterior portion of the disc space during implant insertion.

In a preferred embodiment branches 602 and 604 of inserter guide 600 can be manipulated to separate guide portions 608, 610 and place guide portions 608, 610 in contact with the vertebral endplates. This contact allows the desired position of guide members 608, 610 to be maintained during implant insertion. Further, such separation capabilities might be required in order to further distract disc space D1 to facilitate implant insertion or removal. Inserter guide 600 includes a mechanism to force and/or maintain the separation of guide members 608 and 610. The spreading mechanism includes an externally threaded rod 612 joined to branch 602 and extending through hole 613 formed in the proximal end of branch 604. The spreading mechanism has an internally threaded hand nut 614 threadedly received on rod 612. Branches 602 and 604 may be forced together by action of internally threaded nut 614 on branch 604 forcing it towards branch 602, thereby forcing guide members 608 and 610 apart and into contact with the vertebral endplates.

Figure 36:
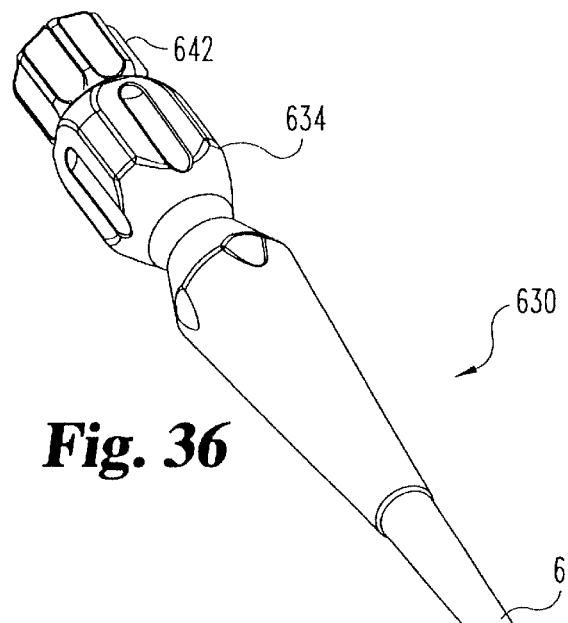
FIG. 36 is a perspective view of a straight implant inserter according to the present invention having the outer shaft partially cut-away to show the inner shaft.

Referring now to FIG. 36, there is shown a straight implant inserter 630. Inserter 630 includes a rigid hollow outer shaft 632 secured to a handle 634 at the proximal end of shaft 632. An inner shaft 636, either rigid or flexible, extends through outer shaft 632 and includes an implant connector 638 at its distal end extending distally from the distal end of outer shaft 632. Implant connector 638 is preferably threaded, but can include other attachment means for engaging the implant. Inner shaft hand nut 642 is coupled to inner shaft 636, and can be rotated to in turn rotate connector 638 to secure or release the implant thereto as desired. A bearing member 640 is secured to outer shaft 636, and contacts the wall of implant to direct an insertion force to the implant.

Figure 37:
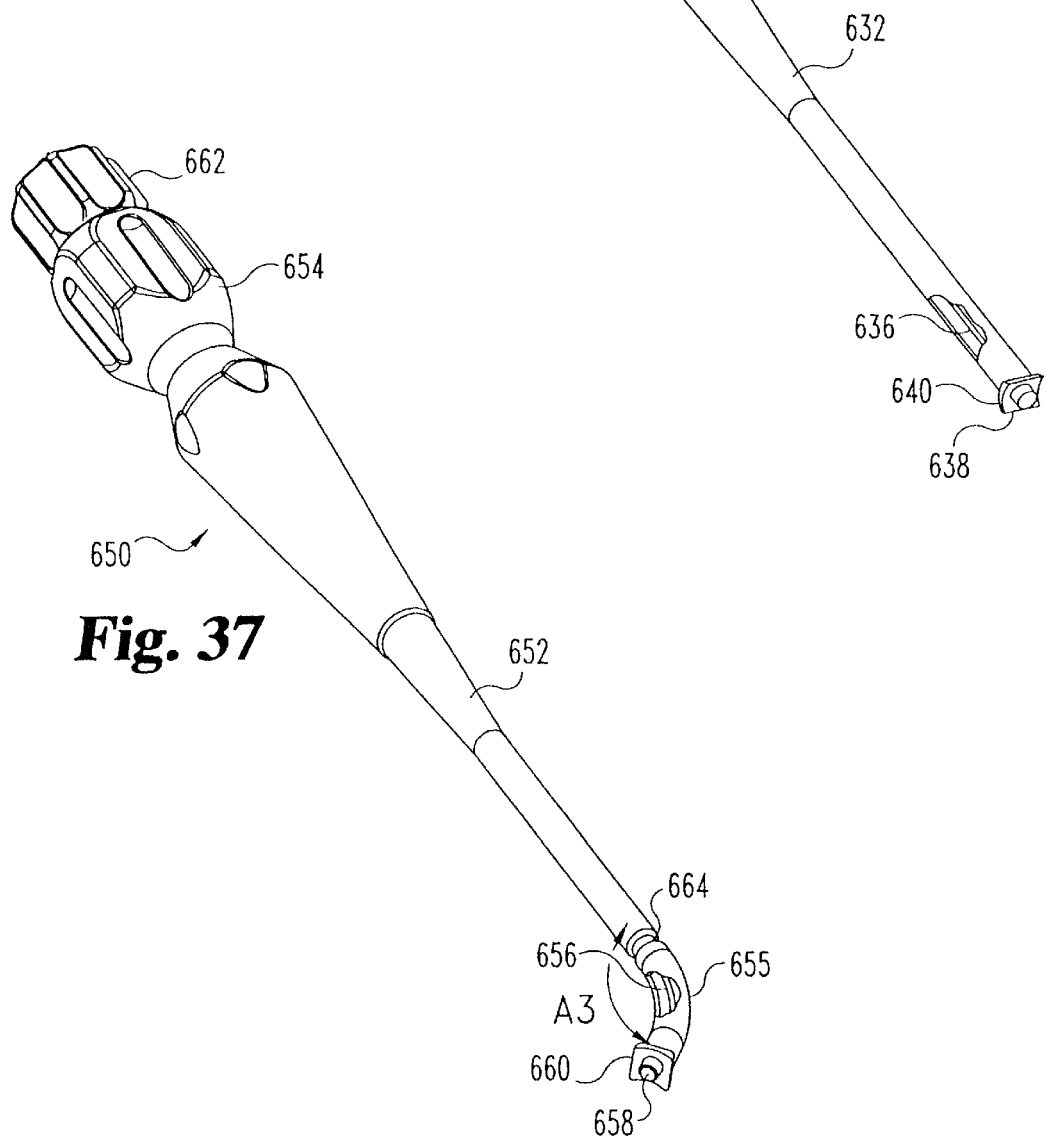
FIG. 37 is a perspective view of a curved implant inserter according to the present invention having the outer shaft partially cut-away to show the inner shaft.
Figure 38:
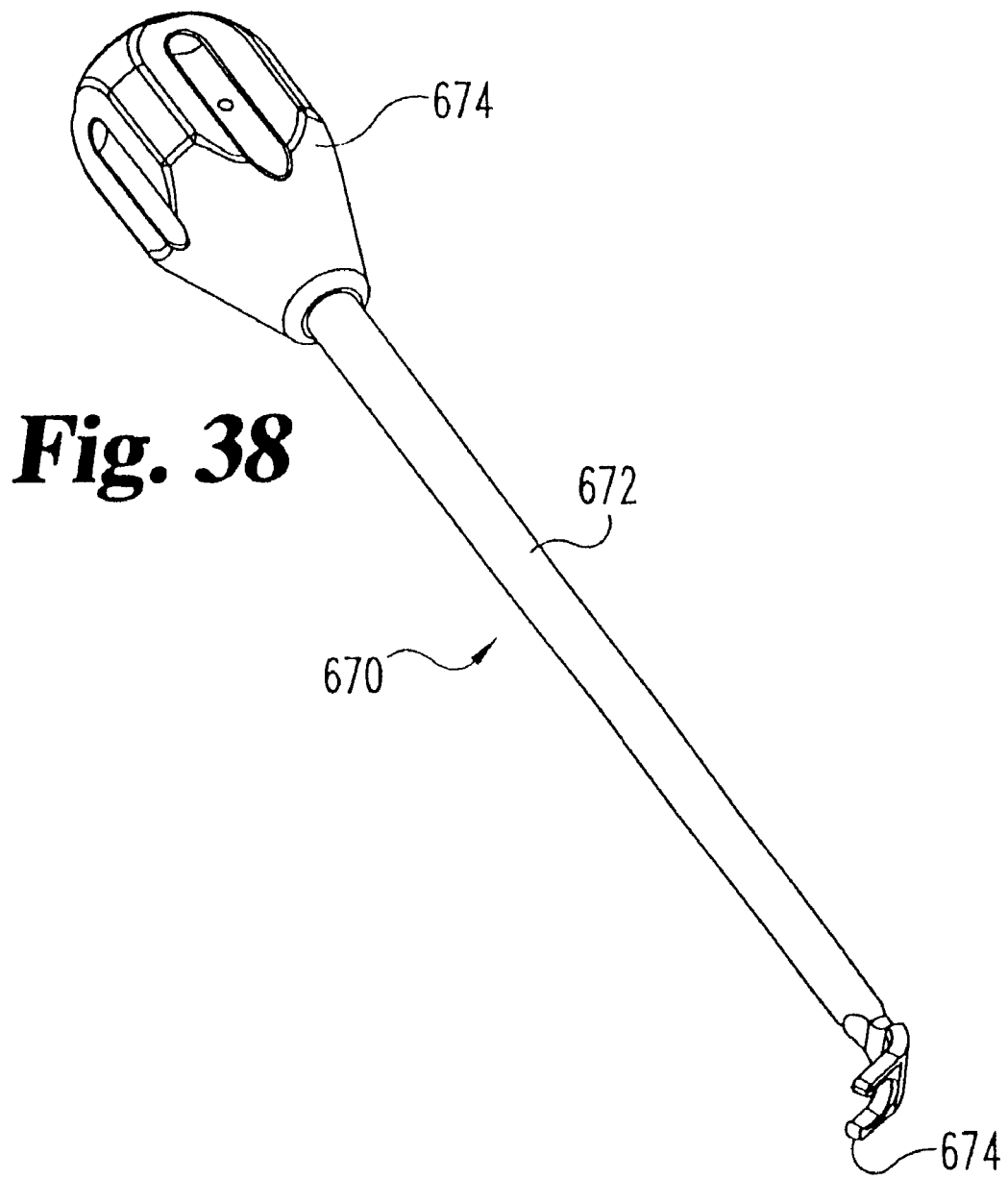
FIG. 38 is a perspective view of an impaction tool according to the present invention.

Referring now to FIGS. 37–38, there is shown a curved inserter 650 and a pusher 670 adapted for use with the curved inserter 650 and other instruments of the present invention. Inserter 650 includes a rigid hollow outer shaft 652 secured to a handle 654 at the proximal end of shaft 652. Outer shaft 652 includes a bend 655 adjacent its distal end forming offset angle A3. A flexible inner shaft 656 extends through outer shaft 652 and bend 655. Inner shaft 656 includes an implant connector 658 at its distal end extending distally from the distal end of outer shaft 652. Implant connector 658 includes threads or other attachment means for engaging an implant. Inner shaft hand nut 662 is coupled to inner shaft 656, and can be rotated to in turn rotate connector 658 to secure or release the implant thereto as desired. A bearing member 660 is secured to outer shaft 656, and contacts the wall of the implant to direct the insertion force thereto. An impaction tool engaging portion 664 in the form of a notch formed around outer shaft 664 is provided in outer shaft 652.

An impaction tool or pusher 670 includes a shaft 672 having a bulb handle 674 secured to the proximal end of shaft 672. A shaft engaging portion 674 is secured to and extends from the distal end of shaft 672. In the illustrated embodiment, shaft engaging portion 674 is a U-shaped prong, and is positionable in notch 664 to apply a pushing force to curved inserter 650 to facilitate placement the implant secured to inserter 650 into distal portion 37 of disc space D1.

Figure 39:
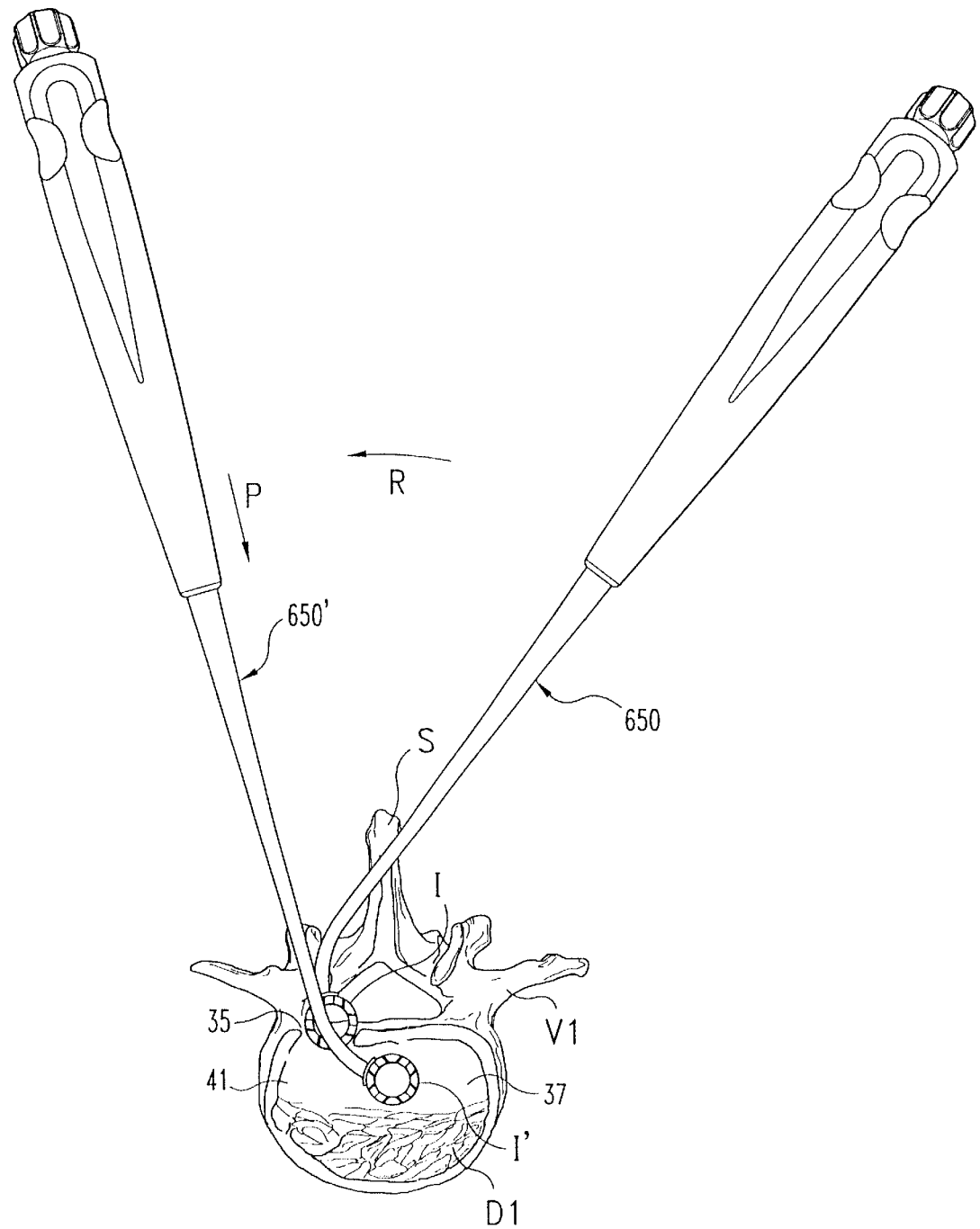
FIG. 39 is a top plan view of the disc space showing the sequence of the curved inserter of FIG. 37 inserting an implant into the disc space.

Insertion of implant I with curved inserter 650 is shown in FIG. 39. Implant I is attached to inserter 650, and implant I is then positioned in opening 35 with inserter 650 oriented such that it extends across spinous process S. As implant I is advanced from proximal portion 41 to distal portion 37 of disc space D1, inserter 650 is pivoted around spinous process S to the position indicated by inserter 650'. Pusher 670 can be used to facilitate insertion by allowing the surgeon to use pusher 670 to apply the insertion force with one hand while the other hand is used to pivot inserter 650.

An alternate embodiment implant insertion device is shown in FIGS. 40 through 44. The implant inserter 300 includes an inner guiding shaft 302 having a handle 308 attached to one end and a stop 306 disposed on the opposite end. Guiding shaft 302 includes a bend 304 adjacent the distal portion. Insertion sleeve 310 is slidably disposed about inner shaft 302. As previously described with respect to chisel 230, insertion sleeve 310 includes a drive portion 314 and impact shoulder 316 for use with a slap hammer, if necessary. Insertion sleeve 310 is connected at its distal end to an implant driver 318 by a flexible drive member 312. Implant driver 318 includes an arcuate cavity 322 having a substantially concave surface. The concave surface terminates adjacent the inner shaft 302.

Figure 42:
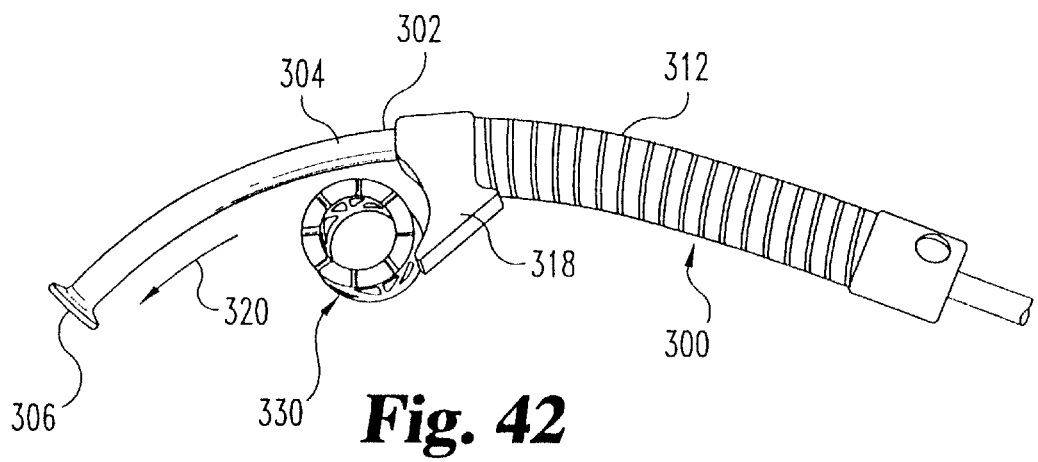
FIG. 42 is an enlarged plan view of the distal portion of the implant inserter of FIG. 40 and an implant.
Figure 43:
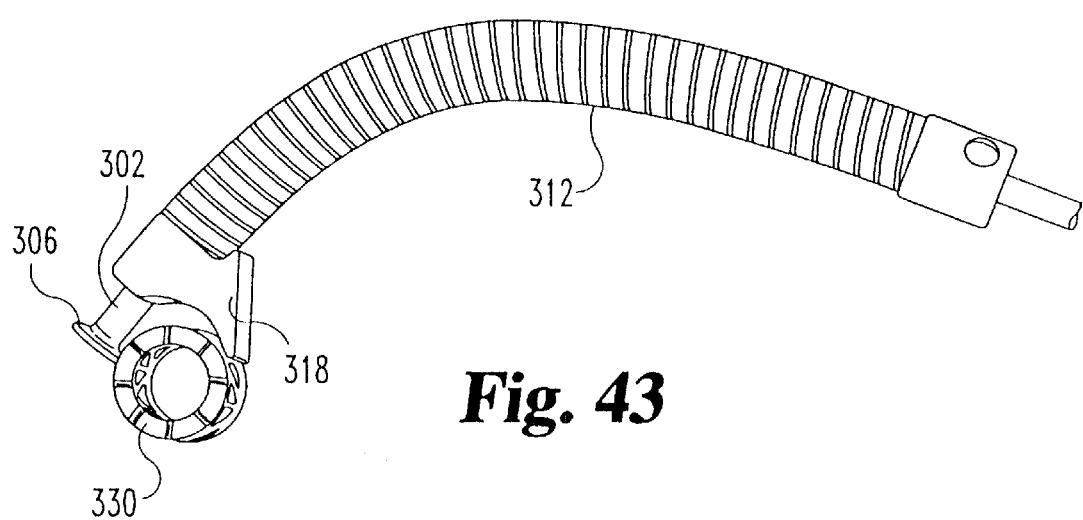
FIG. 43 is the view of FIG. 42 showing the implant and insertion tool moved distally along the guide shaft.

As shown in FIGS. 42 through 43, an implant 330 is engaged to implant driver 318 with a portion of the implant positioned in arcuate cavity 322. Driver 318 urges implant 330 in the direction of arrow 320. It will be understood that driver 318 and guide rod 302 cooperate to guide the implant along an arcuate path through the disc space formed by guide rod 302. Implant 300 is one example of an implant that may be inserted with instruments according to the present invention. Further suitable implants are disclosed in U.S. Pat. No. 5,897,556 and also in PCT International Application PCT/US00/41392 entitled IMPACTED ORTHOPEDIC BONE SUPPORT IMPLANT, each of which is incorporated herein by reference in its entirety. The implant inserted with the instruments and techniques of the present invention could also be a spacer, a disc prosthesis or disc nucleus prosthesis.

Figure 44:
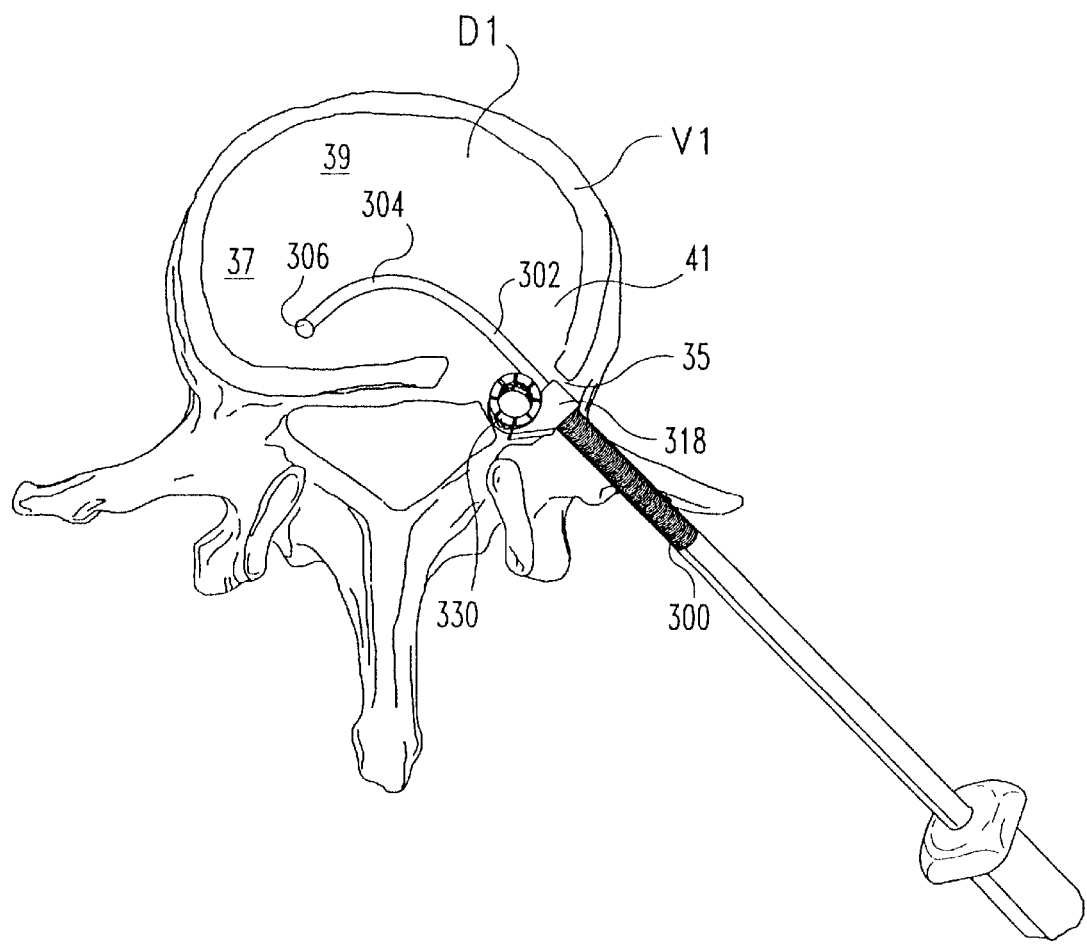
FIG. 44 is a top plan view of a vertebra with the implant inserter of FIG. 40 in the disc space.
Figure 45:
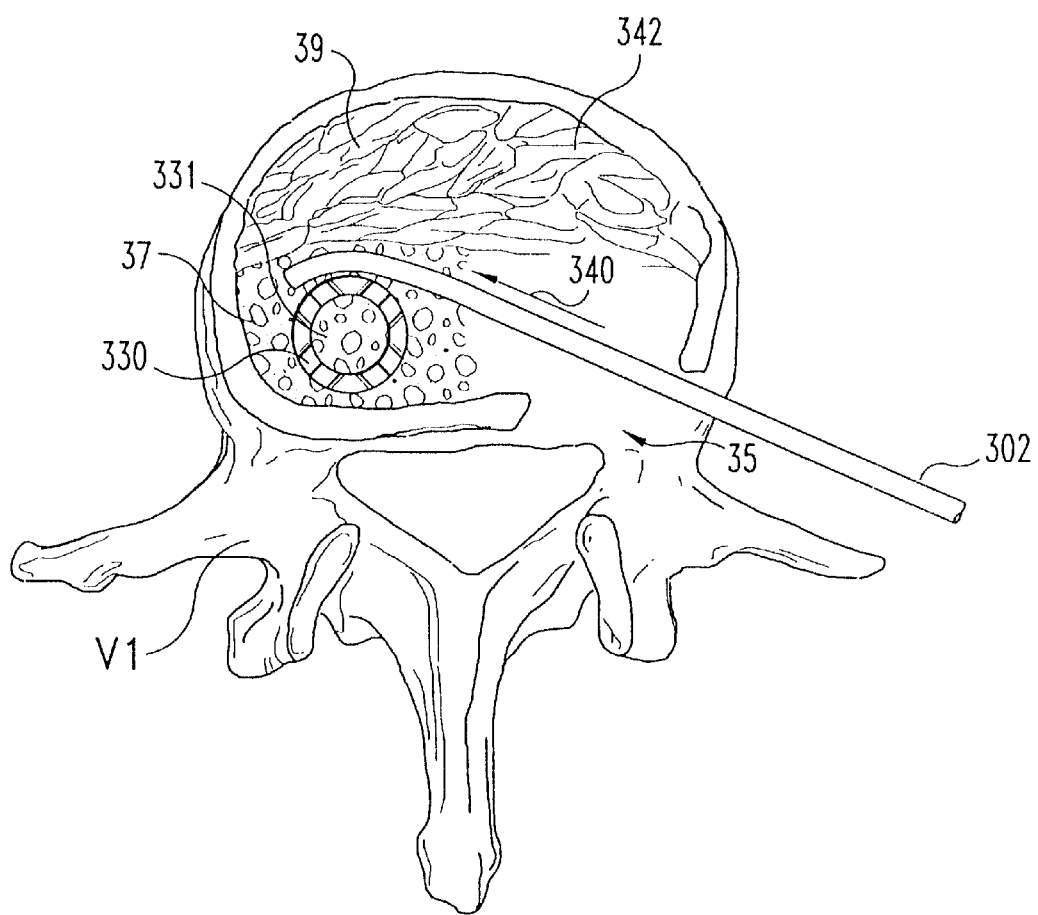
FIG. 45 is a top plan view of a vertebra with an implant inserted into the distal portion of the disc space.
Figure 46:
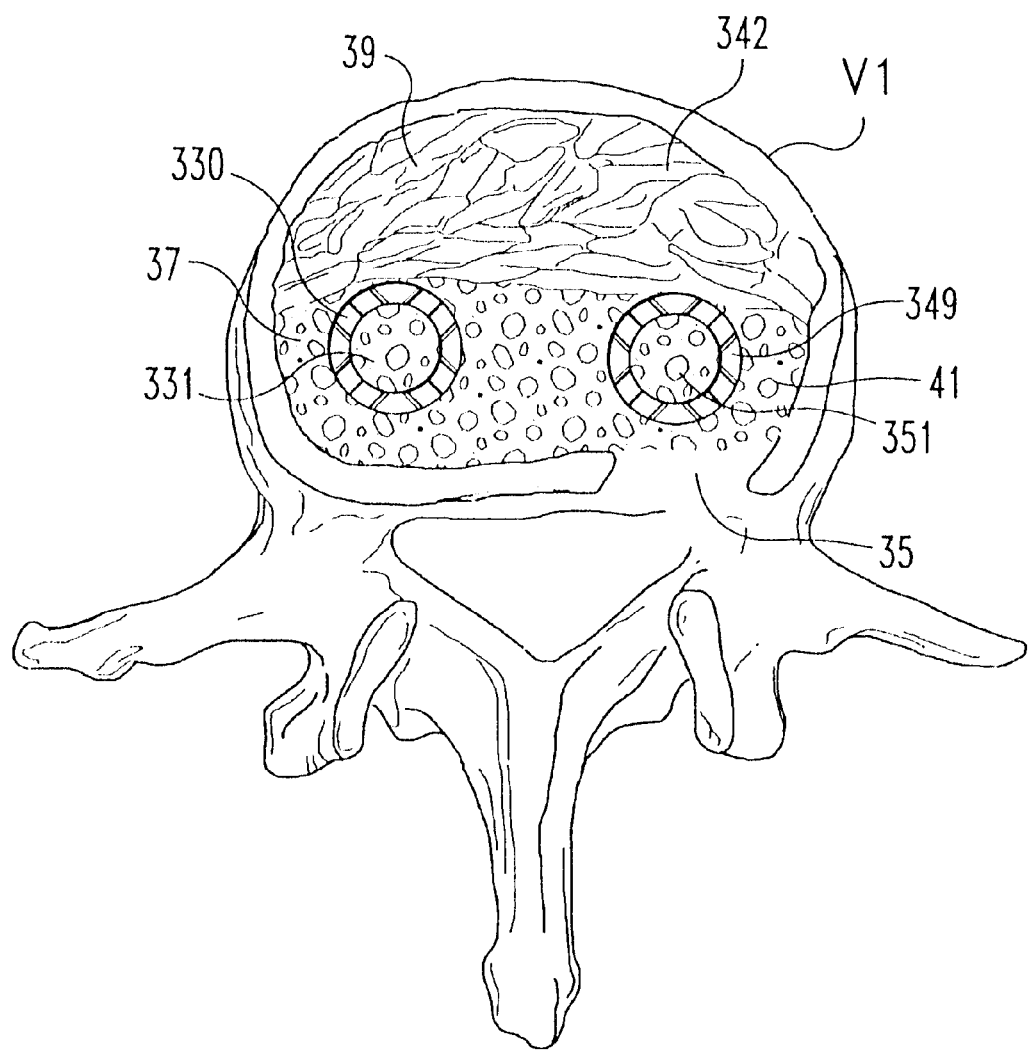
FIG. 46 is a top plan view of a vertebra with a pair of implants bi-laterally positioned in the disc space to provide bilateral support to the spinal column segment.

As shown in FIG. 44, inner shaft 302 of implant inserter is positioned in disc space D1 with stop 306 positioned adjacent distal portion 37. Implant 330 is positioned in opening 35 and implant driver 318 is urged forwardly along guide shaft 304 to drive the implant to distal portion 37 of disc space D1 as shown in FIG. 45. Once implant 330 is positioned in the desired location, bone ingrowth promoting material may be positioned around implant 330 using guide rod 302 as a guide for placement. Bone ingrowth promoting material 331 can also be placed in the interior portions of implant 330 prior to placement. Additionally, bone ingrowth promoting material 342 may be positioned in the anterior portion 39 of the disc space. As shown in FIG. 46, a second implant 349 may be placed in the proximal portion 41 of the disc space to complete a bilateral placement of implants to provide balanced structural support in disc space D1. Second implant 349 may also be filled with bone growth promoting material 351.

While some of the above-described instruments illustrate a separate guide rod for each instrument, it is contemplated that a single guide rod may be positioned in the disc space and multiple instruments advanced over the guide rod to complete disc space preparation and implant insertion. Further, the stop on the guide rod may include selectively engageable portions that may be engaged with the vertebral endplates to maintain the position of the guide rod in the disc space.

Figure 47:
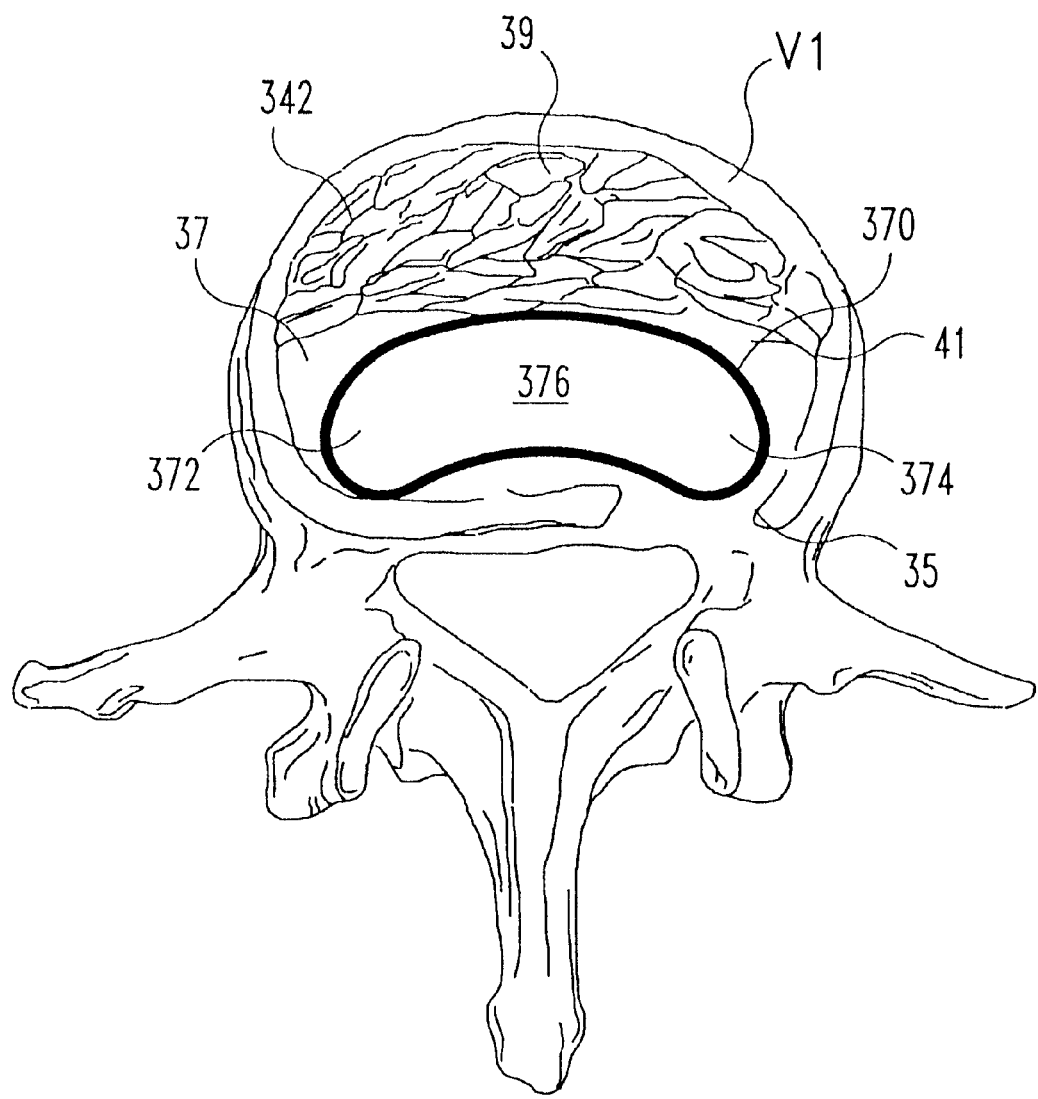
FIG. 47 is a top plan view of a vertebra with a single implant positioned in the disc space to provide bilateral support to the spinal column segment.

In a further alternative embodiment implant shown in FIG. 47, the disc space is prepared using the any combination of instruments described above. The anterior portion 39 of the disc space may be packed with bone ingrowth promoting material 342. A dual lobe implant 370, which can have features such as those described below with respect to implant 1000, is placed in the disc space D1 and has a length sufficient to span the disc space from the distal portion 37 to the proximal portion 41. Implant 370 includes a first distal lobe 372 and a second proximal lobe 374. A central opening 376 is provided that may be filled with bone ingrowth material. Implant 370 may be positioned by using any of the implant inserters described herein.

Figure 48:
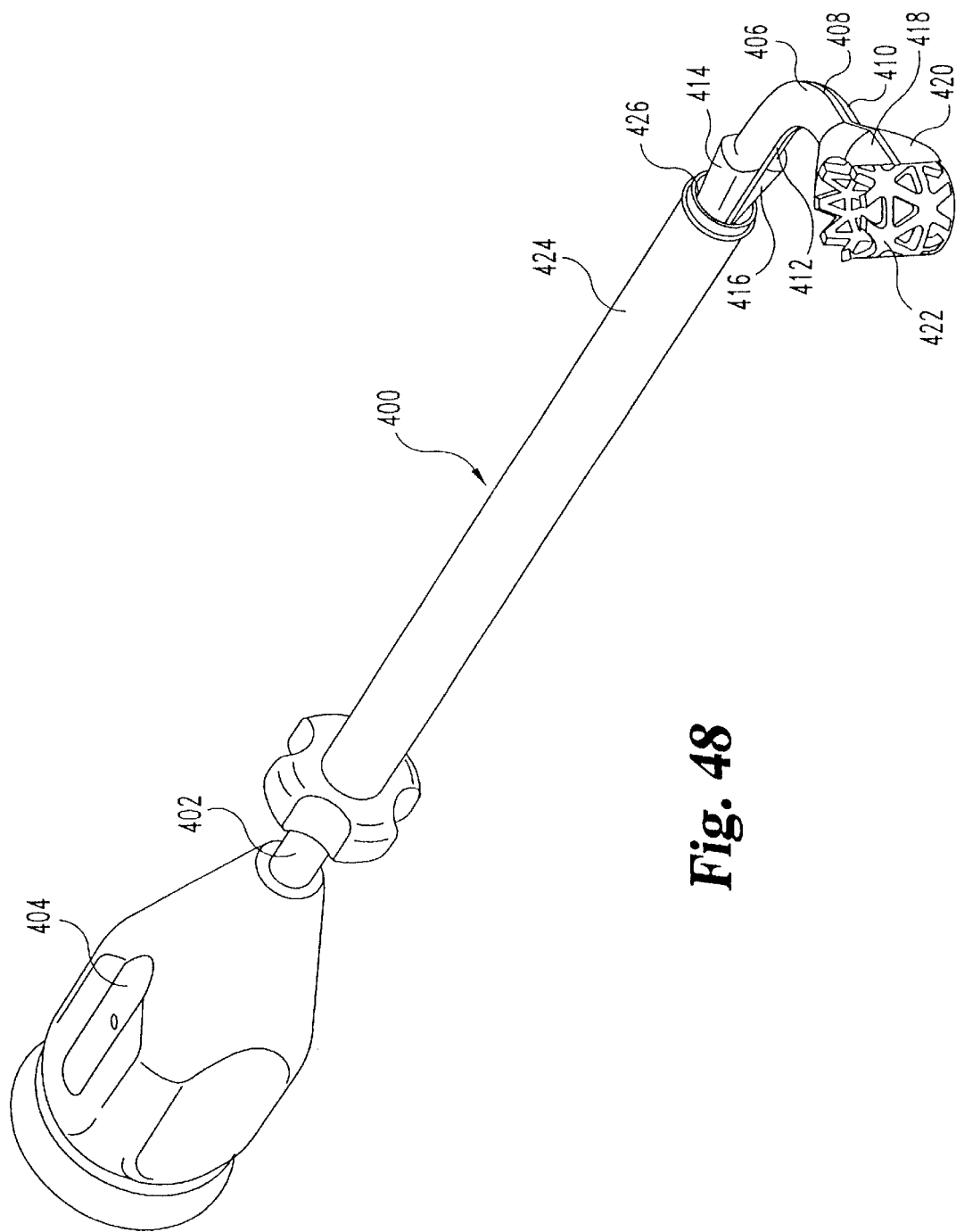
FIG. 48 is a perspective view of an alternate embodiment implant inserter.

FIG. 48 illustrates one example another embodiment implant inserter according to the present invention. Implant inserter 400 includes an elongated shaft 402 with a handle 404 at its proximal end and an implant-gripping end at the opposite end. The implant-gripping end includes bifurcated branches 408 and 410 separated by a space 412. The bifurcated branches each include a bend 406 to accommodate implant placement through opening 35 and into disc space D1. Branch 408 includes an inclined surface 414 and an implant engagement block 418. Similarly, branch 410 includes inclined surface 416 and an implant engagement block 420. Each engagement block includes at least one projection (not shown) for insertion into a wall opening of implant 422 having a bearing surface to engage implant 422. An outer sleeve 424 is slidably disposed on inner shaft 402 with an internal channel 426. It will be understood that as sleeve 424 is advanced toward implant 422, sleeve 424 will engage inclines 414 and 416 thereby urging branches 408 and 410 towards each other. The projections on engagement blocks 418 and 420 will then firmly engage implant 422.

Figure 49:
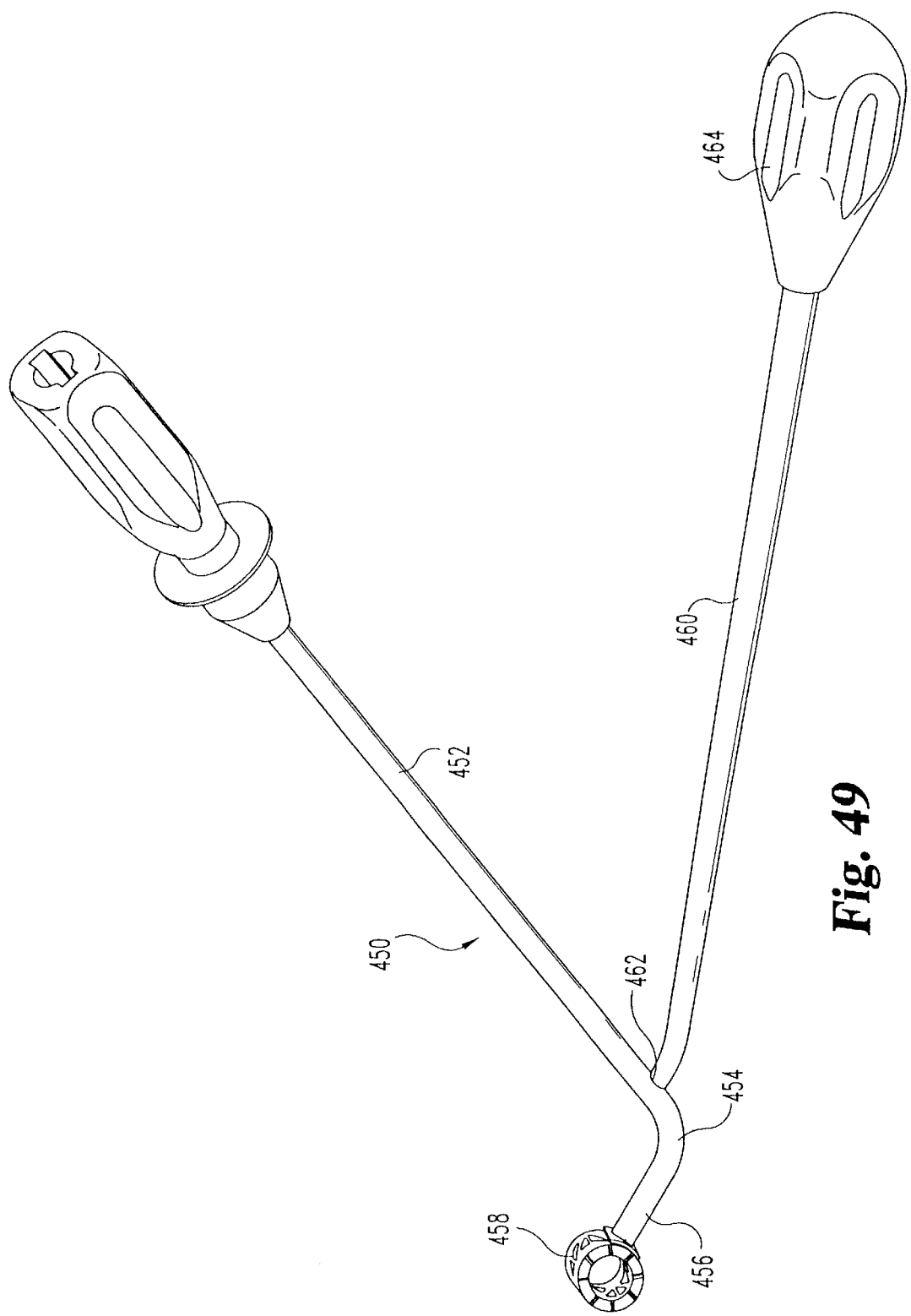
FIG. 49 is a perspective view of a still a further embodiment of an implant inserter.

In a further embodiment illustrated in FIG. 49, implant inserter 450 has an implant engagement end 456 offset from shaft 452 by a bend 454. A pusher 460 includes a handle 464 at one end and a projection (not shown) at the opposite end 462 for engagement with a corresponding opening (not shown) on shaft 452. Pusher 460 provides a mechanism for the surgeon to use one hand to urge implant 458 across disc space D1, while the other hand of the surgeon pivots implant 458 with inserter 450 as it is moved across disc space D1. The longitudinal axis of pusher 460 is in relatively substantial alignment with the longitudinal axis of implant engagement end 456. Thus, longitudinal force applied on pusher 460 may be directly transmitted as longitudinal force to advance implant 458 into the disc space.

Figure 50A:
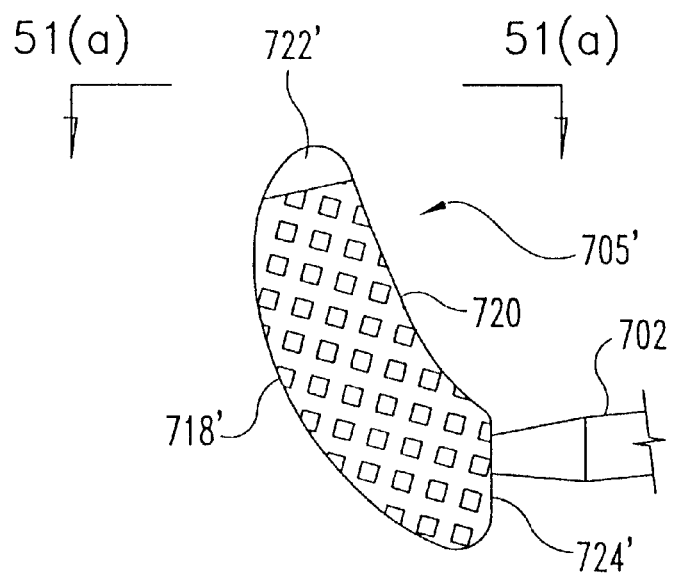
FIG. 50(a) is an enlarged view of an alternate embodiment head for the intradiscal rasp of FIG. 50.
Figure 51A:
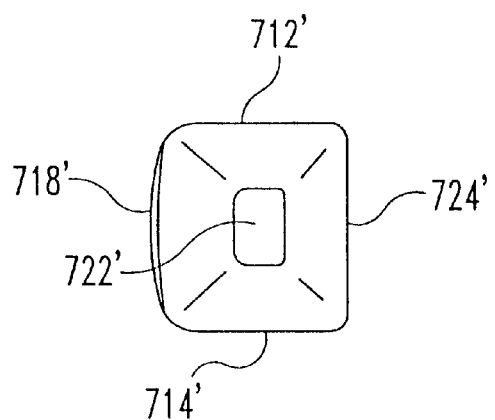
FIG. 51(a) is an elevational view of the head of FIG. 50(a) looking in the direction of arrows 51(a)—51(a).

Referring to FIGS. 50–51, an intradiscal rasp 700 according to the present invention is shown that is useful for disc space preparation with the approaches discussed herein. It is further contemplated that rasp 700 also has application with approaches and intradiscal procedures other than those discussed herein. Rasp 700 includes an elongated shaft 702 with a handle 704 on the proximal end of shaft 702 and a rasping head 705 on the distal end of shaft 702. Shaft 702 has a distal portion 708 laterally offset from a proximal portion 706 to facilitate insertion of rasping head 705 into the disc space. Rasping head 705 is joined to and extends laterally from distal portion 708 and has a leading end wall 722 that is laterally offset from proximal portion 708 in the same direction as but to a greater extent than distal portion 708. The configuration of shaft 702 also allows the surgeon to place rasping head 705 in contact with the vertebral endplates to prepare distal portion 37 of disc space D1 for implant insertion. Shaft 702 and rasping head 705 are configured in a manner that further allows preparation via a posterior lateral approach of at least a portion of the anterior third of the disc space for receipt of an implant. In order to match the endplate area prepared to the implant, rasping head 705 can have a size and shape, when viewed in the direction of the vertebral endplates, that generally corresponds to the size and shape of the implant to be inserted. In the illustrated embodiment, rasping head 705 has a generally banana or boomerang shape that generally corresponds to the shape of the vertebral endplate contacting surfaces of the implant 1000 discussed below. However, it should be understood that rasping head 705 can also be used for implants having other shapes, including circular, semi-circular, square, rectangular, or ovoid shapes, to name a few.

Further details regarding shaft 702 and rasping head 705 will now be discussed. Shaft 702 has proximal portion 706, distal portion 708, and an intermediate connecting portion 710 extending between and joining proximal portion 706 and distal portion 708. Proximal portion 706 extends along a central axis 707, distal portion 708 extends along a central axis 709, and connecting portion 710 extends along a central axis 711. Shaft 702 forms an angle A2 between central axis 707 and central axis 711, and an angle A22 between central axis 711 and central axis 709. Thus, connecting portion 710 laterally offsets distal portion 708 from proximal portion 706 a distance d. In one specific embodiment, this distance d is about 10 millimeters. Rasping head 705 extends from shaft 702 such that its leading end wall 722 is positioned even further laterally offset from proximal portion 706 than distal portion 708. This configuration allows shaft 702 to be initially positioned across spinous process S (such as shown with respect to inserter 1000 in FIG. 53) and then pivoted in the direction of arrow R away from spinous process S as rasping head 705 is inserted into disc space D1. Rasping head 705 can thus be used by the surgeon to create a rasped endplate portion on each vertebral endplate that generally corresponds to the implant insertion path.

As shown in FIG. 51, rasping head 705 includes a first rasping surface 712 and an opposite second rasping surface 714. Rasping head 705 further includes an anterior wall 718, a posterior wall 720, leading end wall 722 and a trailing end wall 724. Rasping head 705 is connected, mounted, integrally formed with, or otherwise attached to shaft 702 at trailing end wall 724. Each of these walls 718, 720, 722, and 724 has a smooth surface finish, and leading end wall 722 is rounded to provide a smooth transition between anterior wall 718 and posterior wall 720. Anterior wall 718 has a convex profile that, in addition to generally matching the shape of the anterior wall of implant 1000, also generally corresponds to the shape of the anterior inner annulus wall and can contact this annulus wall to limit insertion depth of rasping head 705. Posterior wall 720 has a slightly concave profile of less curvature than anterior wall 718, and posterior wall is shorter than anterior wall 718 between leading end 722 and trailing end 724. Posterior wall 724 generally corresponds to the shape of the posterior edge of the vertebral endplate.

In an alternate embodiment shown in FIGS. 50(*a*) and 51(*a*), rasp 700 has a rasping head 705' with a leading end wall 722' that is bulleted or tapered to facilitate entry of rasping head 705' into the disc space. This alternate embodiment further includes a rasping surface on the anterior wall 718' that can scrape material in the anterior portion of the disc space. First and second rasping surfaces 712', 714' can be used to rasp material from the vertebral endplates. In this embodiment, posterior wall 702', leading end wall 722' and trailing end wall 724' have a smooth surface finish.

Rasping surfaces of rasp 700 are provided with a surface configuration that allows that surgeon to scrape endplate material as the rasp is moved across the endplate. In one form, this rasping surfaces includes a plurality of pyramid-shaped teeth each having their upper most point positioned to contact the vertebral endplate. It is further contemplated that other rasping surfaces known to those skilled in the art could be provided, such as, for example, a plurality of frusto-conical projections, spikes, diamond-shaped projections, or wedge-shaped projections that each extend across the width of the rasping surface. Rasping surfaces 712, 714 can simultaneously contact the adjacent upper or lower vertebral endplates, or rasp 700 can be manipulated in the disc space to selectively contact one of the upper endplate or the lower endplate. In one specific embodiment, rasping head 705 has a height 716 between the outermost ends of the rasping surfaces 712, 714 of 8 millimeters. In another specific embodiment, height 716 is 6 millimeters. However, it should be understood that other heights are also contemplated so long as rasping head 705 can be positioned in the intradiscal space.

Figure 52:
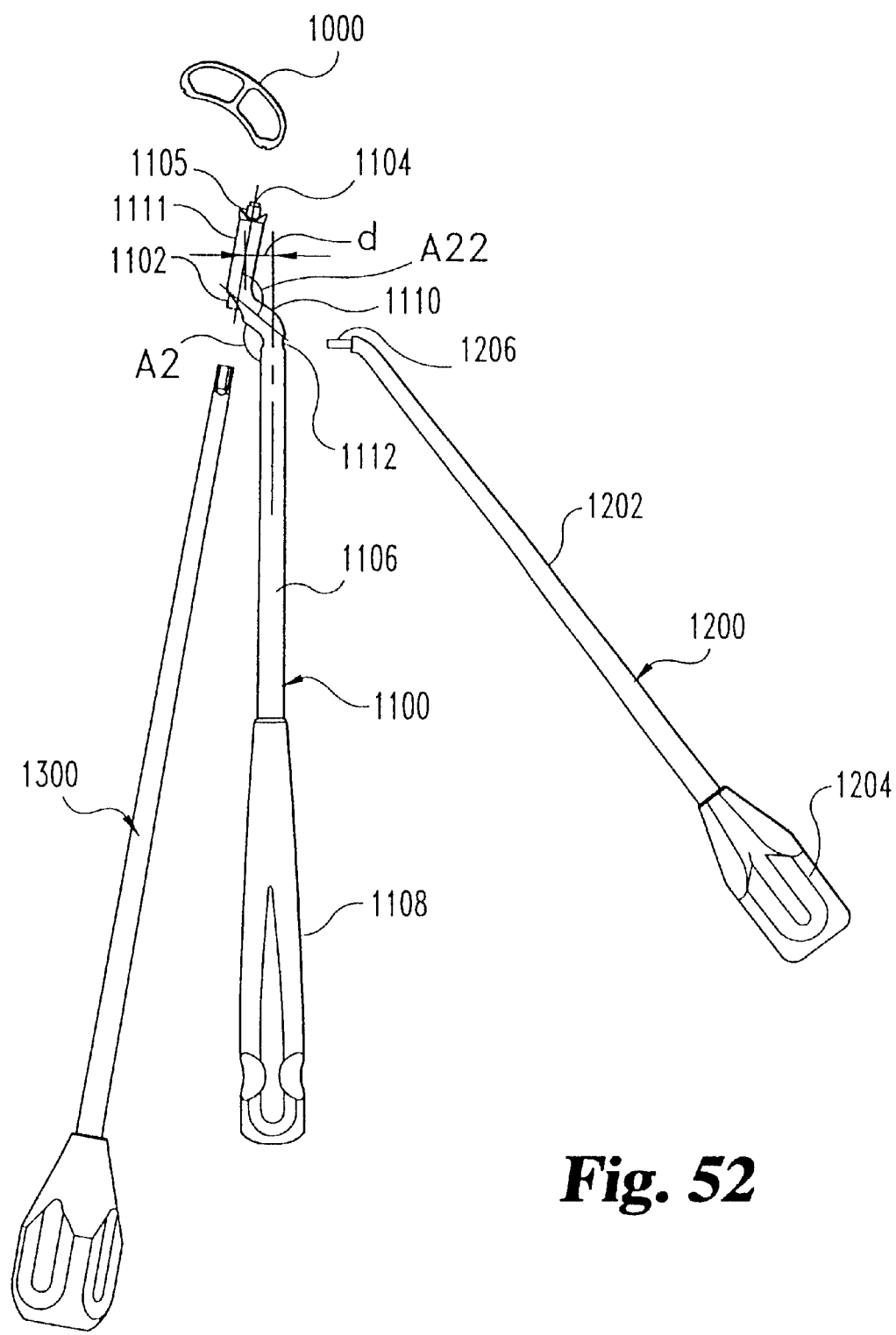
FIG. 52 is a top plan view of an implant and instrument set for inserting the implant into the disc space.
Figure 53:
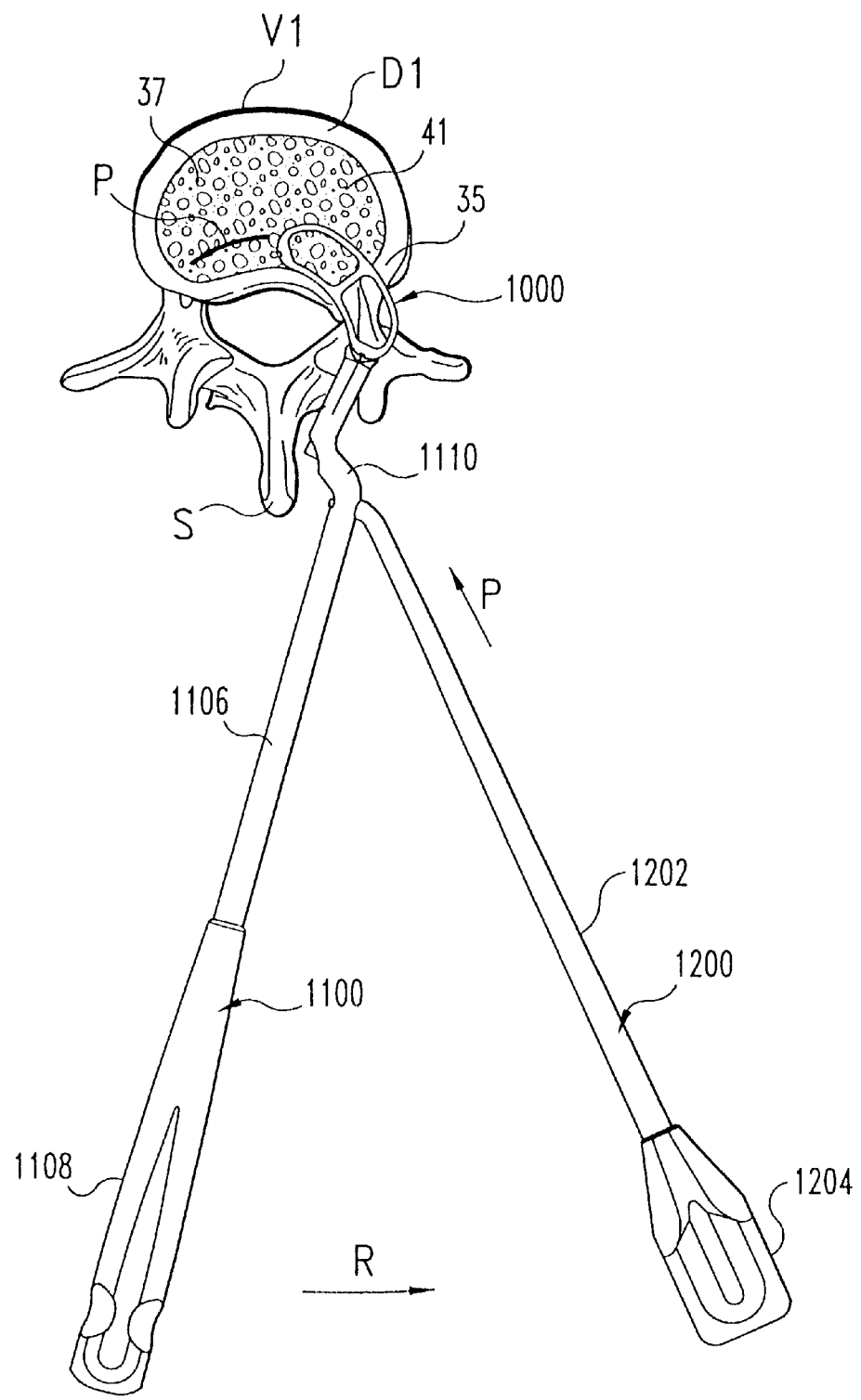
FIG. 53 is a top plan view of the implant and instrument set of FIG. 52 with the implant partially inserted in the disc space.

Referring now to FIGS. 52–53, another embodiment implant and instrument set for inserting the implant into disc space D1 through opening 35 are provided. The instrument set includes an implant insertion tool in the form of inserter 1100, an impaction tool in the form of pusher 1200, and driver 1300. Inserter 1100 has a proximal portion with a shaft 1106 and a handle 1108 secured to the proximal end of shaft 1106. Shaft 1106 includes has a distal working end having a rotatable connecting portion 1102 with a threaded distal end portion 1104 for engaging a threaded opening on implant 1000. A male protrusion member 1105 extends from end portion 1104, and is positionable in a slot formed in implant 1000 as described further below. Driver 1300 is engageable to the proximal end of connecting portion 1102 to thereby rotate connecting portion 1102 to threadingly engage implant 1000 to threaded end portion 1104 of inserter 1100. Shaft 1106 further includes a lateral offset 1110 having a bend forming angle A2 with shaft 1106 and an angle A22 with distal shaft portion 1111, and is configured similar to the shaft of rasp 700 discussed above. Distal portion 1111 is thus offset from the proximal portion of shaft 1106 by distance d. In one specific embodiment, this offset distance is about 10 millimeters. This allows shaft 1106 to be initially positioned across spinous process S, as shown in FIG. 53, and then pivoted in the direction of arrow R away from spinous process S as implant 1000 is positioned in disc space D1. Pusher 1200 has a shaft 1202 and handle 1204 at the proximal end of shaft 1202. Pusher 1200 further includes a reduced diameter distal end portion 1206 positionable in an impaction tool engaging portion in the form of bore 1112 formed in shaft 1106.

The surgeon can use pusher 1200 to apply a pushing force to implant 1000 in the direction of arrow P while inserter 1100 is pivoted in the direction of arrow R to pivot the leading end of implant 1000 towards distal portion 37 of disc space D1. It should be understood that inserter 1100 does not pivot with respect to implant 1000, but rather inserter 1100 follows the proximal end of implant 1000 as the distal end of implant 1000 is pivoted to move implant 1000 non-linearly into and across the disc space along insertion path P. The inserter 1100 and pusher 1200 provide the surgeon the ability to use two-handed control to insert implant 1000 into the disc space along non-linear path P since the surgeon controls inserter 1100 with one hand while the other hand provides a pushing or impaction force on implant 1000 with pusher 1200.

Referring now to FIGS. 54–58, various views of implant 1000 are shown and will now be described in further detail. Implant 1000 is an interbody fusion device or cage that can be packed with bone growth material or other known substance and inserted into disc space D1 to promote bony fusion between vertebrae V1 and V2. Furthermore, the structural features of implant 1000 can have application for a disc prosthesis or a disc nucleus prosthesis that is to be inserted into disc space D1 through opening 35. Implant 1000 has a boomerang or banana shape that is suited for insertion to provide bi-lateral support in disc space D1 through a unilateral approach, after the disc space D1 has been accessed and prepared using the above described instruments and techniques. It is also contemplated that disc space D1 can be accessed and prepared for implant insertion using any other known techniques and instruments and other approaches to the disc space, such as lateral, anterior or antero-lateral approaches, for inserting implant 1000. However, a particular problem exists providing bilateral support to the intradiscal space in instances where the disc space is accessed from a posterior lateral approach, such as a transforaminal approach, due to the difficulty in accessing and inserting the implant into distal portion 37 of disc space D1. Implant 1000 addresses this problem by providing a design that is suited for insertion into opening 35 and for subsequent pivotal movement and impaction movement through disc space D1 into distal portion 37.

Implant 1000 includes a concave posterior wall 1002 and an opposite convex anterior wall 1004. Implant 1000 further includes an arcuate leading end wall 1006 and an arcuate trailing end wall 1008. Each of the end walls 1006, 1008 extend between and connect posterior wall 1002 and anterior wall 1004, and provide a smooth transition therebetween to facilitate passage of implant 1000 through disc space D1. Implant 1000 further includes an upper bearing member 1010 and a lower bearing member 1012 extending between and connecting walls 1002, 1004, 1006 and 1008.

Figure 56:
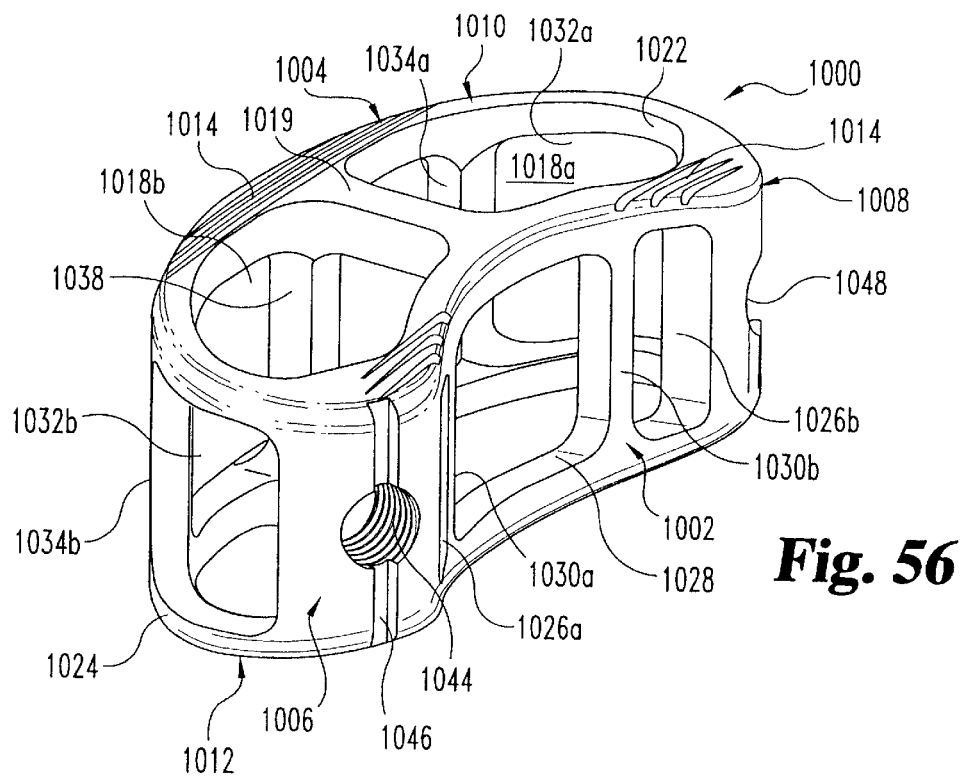
FIG. 56 is a perspective of the implant of FIG. 54 oriented towards the posterior face.
Figure 57:
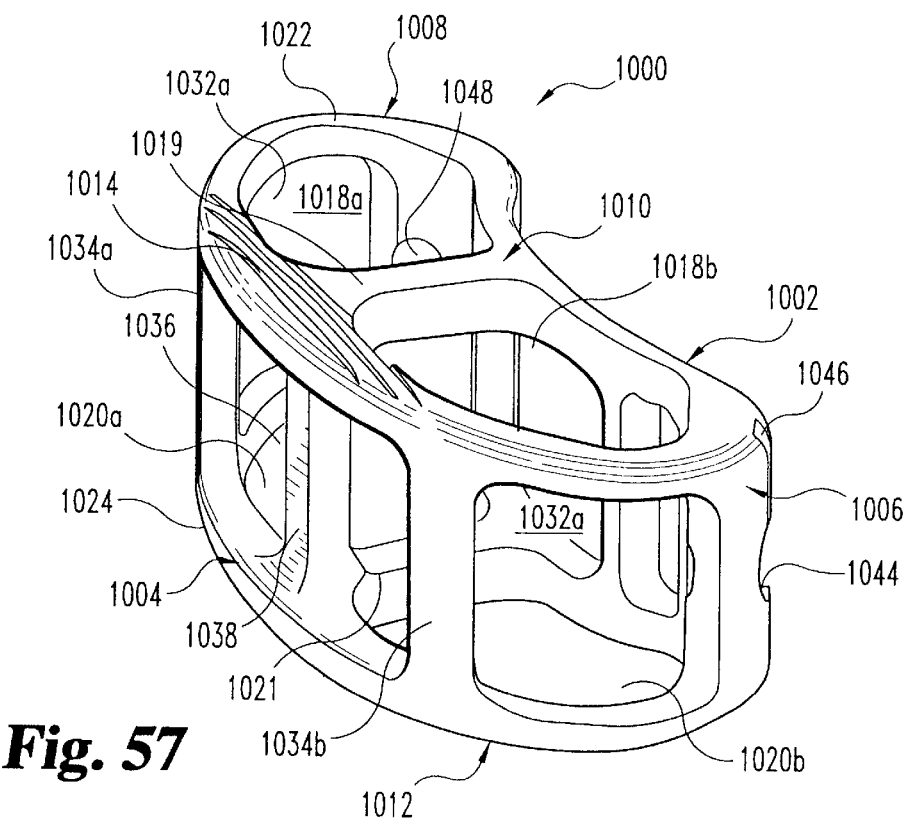
FIG. 57 is another perspective view of the implant of FIG. 54 oriented towards the anterior face.
Figure 58:
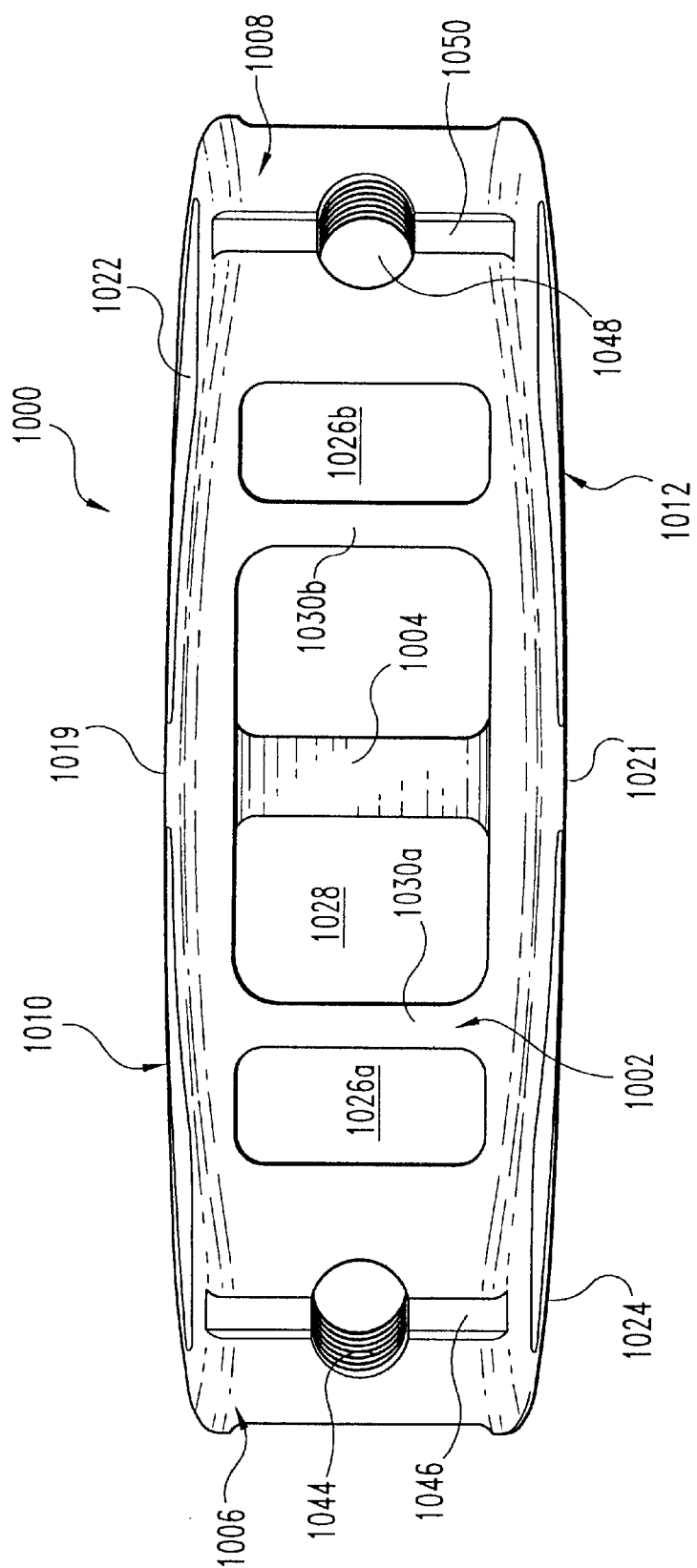
FIG. 58 is an elevational view of the implant of FIG. 54 looking towards the posterior face.

Implant 1000 has a height H1 at the medial portion of posterior wall 1002 and a second height H2 at the medial portion of anterior wall 1004. Upper bearing member 1010 and lower bearing member 1012 have a slight convexity between the anterior and posterior walls 1002, 1004 and height H2 is preferably greater then H1 in order to correspond to the anatomy of the vertebral endplates at the posterior portion of disc space D1. Leading end wall 1006 and trailing end wall 108 further have a height H3 that is less than H1 and H2, and upper bearing member 1010 and lower bearing member 1012 have a slight convexity between leading end 1006 and trailing end 1008 as best shown in FIG. 56. This double convexity preferably matches the double concavity of the adjacent vertebral endplate. Furthermore, the difference in heights between the upper and lower bearing members at the anterior and posterior walls can be provided so as to establish lordosis when implant 1000 is inserted in the disc space. Implant 1000 thus has application in restoring and maintaining spinal lordosis from a posterolateral approach.

Upper bearing member 1010 can further be provided with a number of grooves 1014 and lower bearing member 1012 can be provided with a number of grooves 1016. Grooves 1014 and 1016 can engage the vertebral endplates to resist posterior and anterior migration of implant 1000 in the disc space.

In order to promote fusion, the walls and bearing members of implant 1000 are provided with a number of openings. Upper bearing member 1010 includes upper openings 1018*a* and 1018*b* separated by an upper strut 1019. Lower bearing member 1012 includes lower openings 1020*a* and 1020*b* separated by a lower strut 1021. An upper bar 1022 forming the perimeter of upper bearing member 1010 has a boomerang shape, and surrounds upper openings 1018*a*, 1018*b* and is connected to strut 1019. Similarly, a lower bar 1024 forming the perimeter of lower bearing member 1012 has a boomerang shape, and surrounds lower openings 1020*a*, 1020*b* and is connected to strut 1021. Posterior wall 1002 includes a pair of posterior lateral openings 1026*a* and 1026*b* adjacent to the posterior side of leading end wall 1006 and trailing end wall 1008, respectively. Posterior vertical struts 1030*a* and 1030*b* extend between and are connected to upper bar 1022 and lower bar 1024 on the medial side of openings 1026*a* and 1026*b*, respectively. A posterior middle opening 1028 that is larger than posterior lateral openings 1026*a*, 1026*b* is defined between vertical struts 1030*a*, 1030*b*.

Figure 54:
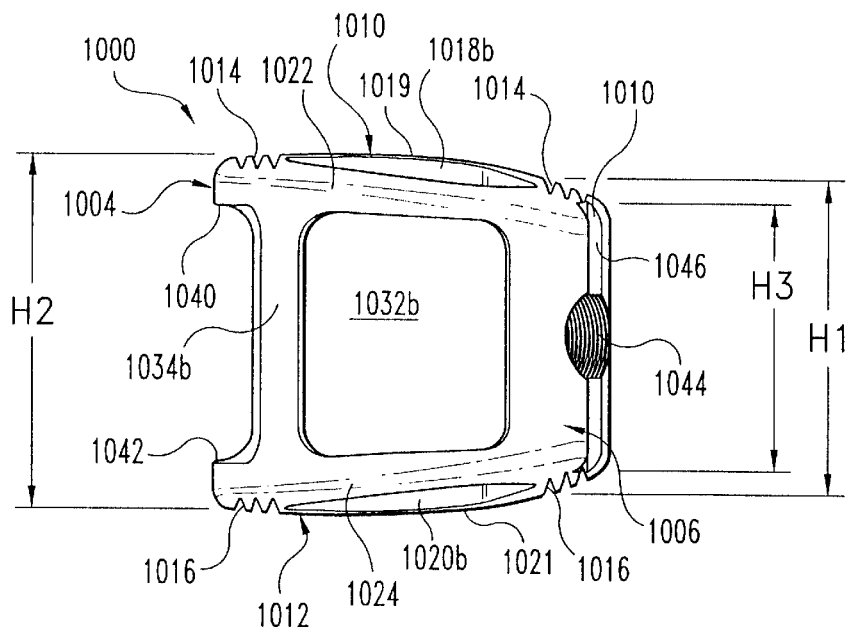
FIG. 54 is an end elevational view of an implant according to another aspect of the present invention.

Anterior wall 1004 includes a pair of anterior lateral openings 1032*b* and 1032*a* adjacent to the anterior side of leading end wall 1006 and trailing end wall 1008, respectively. Anterior vertical struts 1034*a* and 1034*b* extend between and are connected to upper bar 1022 and lower bar 1024 on the medial side of openings 1032*a* and 1032*b*, respectively. An anterior middle opening 1036 that is larger than anterior lateral openings 1032*a*, 1032*b* is defined between vertical struts 1034*a*, 1034*b*. An offset strut 1038 is provided at the middle of opening 1036, and extends between and is connected with upper bar 1022 and lower bar 1024. Since offset strut 1038 is offset toward posterior wall 1002, and offset strut 1038 is also connected with upper strut 1019 and lower strut 1021. As best shown in FIG. 54, offset strut 1038 and middle opening 1036 provide upper member 1010 with an upper cantilevered portion 1040 and lower member 1012 with a lower cantilevered portion 1042. The cantilevered portions 1040, 1042 facilitate x-ray assessment of fusion in the middle of disc space D1 since there is no structural member blocking an x-ray image taken from a lateral view.

Implant 1000 is also provided with an inserter engaging portion 1048 at trailing end 1008 and an identical inserter engaging portion 1044 at leading end 1006 so that implant 1000 is insertable into disc space D1 from a unilateral approach taken on either side of the spinous process. Inserter engaging portions 1044, 1048 are preferably internally threaded and engageable with a distal end of an implant inserter, such as threaded end portion 1104 of inserter 1100 described above. A slot 1046 extends upwardly and downwardly from inserter engaging portion 1044 to upper bearing member 1010 and lower bearing member 1012. A slot 1050 extends upwardly and downwardly from inserter engaging portion 1048 to upper bearing member 1010 and lower bearing member 1012. Slots 1046, 1050 receive male member 1105 of inserter 1100 to prevent rotation of implant 1000 with respect to inserter 1100 when implant 1000 is engaged thereto. The cooperation between slots 1046, 1050 and male member 1105 also properly orients inserter 1100 with respect to implant 1000 when implant 1000 is engaged thereto.

Figure 55:
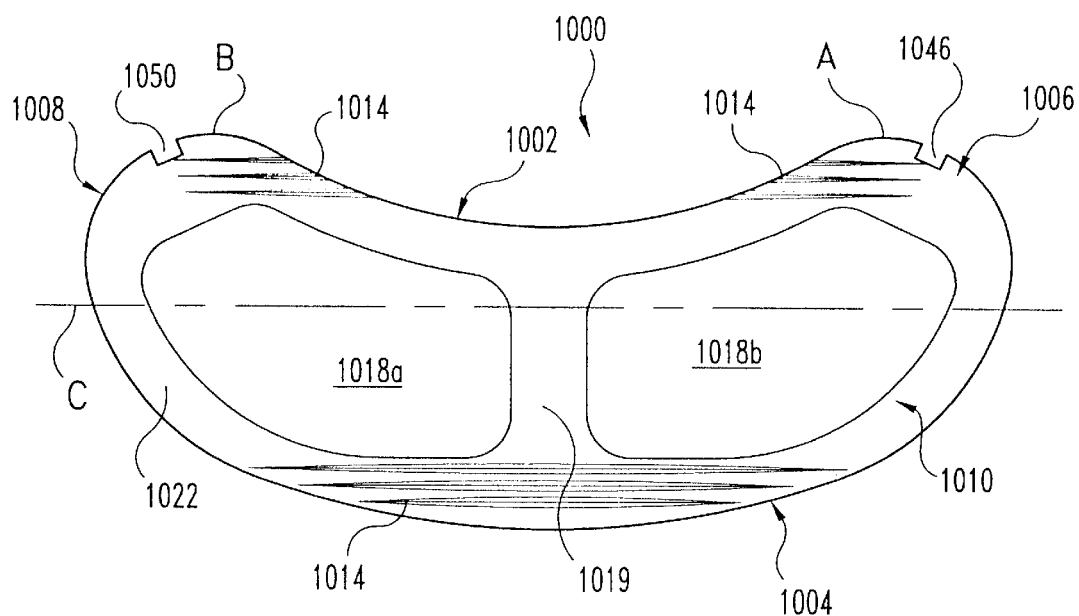
FIG. 55 is a top plan view of the implant of FIG. 54.

Referring now specifically to FIG. 55, implant 1000 has an axis C extending through its centroid. Axis C extends generally in the direction between the leading end and the trailing end of implant 1000, and is equal distance from the most posterior point A on leading end wall 1006 and the most posterior point B on trailing end wall 1008. Leading end wall 1006 is offset to the posterior side of axis C, and trailing end wall 1008 and engaging portions 1044, 1048 are also offset to the posterior side of axis C. The offset in the leading end and trailing ends of implant 1000 facilitates the controlled insertion of implant 1000 along curved insertion path P.

One method for inserting implant 1000 will now be described with reference to FIGS. 52 and 53. Driver 1300 is used to connect implant 1000 to connecting portion 1104 of inserter 1100. Distal end portion 1206 of pusher 1200 is positioned in bore 1112 in shaft 1106. The leading end 1106 of implant 1100 is placed at the opening 35. A manual or mechanical impaction force is applied to pusher 1200 to push implant 1000 a desired amount into proximal portion 41 of disc space D1. Inserter 1100 is pivoted in the direction of arrow R, thereby pivoting leading end 1106 in the disc in the posterior direction. Pusher 1200, pivoted along with inserter 1200, is then used to apply a further impaction force to push implant 1000 further into the disc space. However, due to the pivoting of inserter 1100 and pusher 1200, the direction of insertion is now oriented more towards distal portion 37 of disc space D1. This alternating pivotal and pushing movement of implant 1000 is continued until implant 1000 is placed in the proper position in disc space D1.

implant 1000 provides many further advantages. The shape and location of the bars, struts and walls positions the load bearing members at the strong bony surfaces of the vertebral endplates to provide maximum load support capacity and avoid implant subsidence into the vertebral endplates. The double convexity of the upper and lower bearing members in combination with the boomerang shape provides an intimate fit in the disc space and a profile that matches the concavity of the endplates, providing implant stability and promoting fusion. The openings and hollow interior maximize the volume available to receive bone growth material and also maximize the contact surface area between the bone growth material and the adjacent bony structure. Implant 1000 can be made from titanium, surgical grade stainless steel, or other bio-compatible material using fabricating techniques known in the art.

The above-described instruments and methods have been disclosed with reference to use in substantially open surgical procedures. However, it is contemplated that the implants, instruments and methods may be utilized through guide sleeves or tubes to provided greater protection to adjacent tissues, to reduce the size of access incisions, to provide direct visualization of the surgical site, and/or to provide greater control of the method. The implants, instruments and methods may further be used in combination with disc space preparation and implant insertion through microscopic or endoscopic instruments that provide direct visualization of the surgical site, such as disclosed in U.S. patent application Ser. No. 09/692,932 entitled METHODS AND INSTRUMENTS FOR ENDOSCOPIC INTERBODY SURGICAL TECHNIQUES, filed Oct. 20, 2000, which is incorporated herein by reference in its entirety.

The instruments and methods have been disclosed with reference to a particular application for disc space preparation and implant insertion from a transforaminal approach to the spine. However, there are aspects of the inventions described herein that may be utilized or modified for use for a variety of surgical applications including, but not limited to, spinal surgery from a unilateral posterior approach, a lateral approach, an oblique approach, and through laparoscopic or endoscopic instruments from any of a variety of angles or approaches to the spine.

While the invention has been illustrated and described in detail in the drawings and the foregoing description, the same is considered to be illustrative and not restrictive in character. It is understood that only the preferred embodiments have been shown and described and that all changes and modifications that come within the spirit of the invention are desired to be protected.

What is claimed is:

1. A surgical instrument for performing a surgical procedure in a spinal disc space, comprising:
    a shaft extending generally along a longitudinal axis, said shaft having a proximal portion along said longitudinal axis and a distal portion offset laterally in a first direction from said longitudinal axis; and
    a rasp head at a distal end of said shaft extending from said distal portion transversely to said longitudinal axis.

2. The instrument of claim 1, wherein said rasp head has a first rasping surface positionable against the endplate of an upper vertebral body and an opposite second rasping surface positionable against the endplate of a lower vertebral body.

3. The instrument of claim 1, wherein said shaft includes a connecting portion extending along a second axis, said second axis forming a first angle with said longitudinal axis, and said distal portion extending from said connecting portion to said distal end along a third axis, said third axis forming a second angle with said second axis.

4. The instrument of claim 3, wherein said first angle is different than said second angle.

5. The instrument of claim 3, wherein said longitudinal axis and said third axis intersect distally of said rasp head at an angle of about 5 degrees.

6. The instrument of claim 1, wherein said rasp head has an anterior wall, an opposite posterior wall, a trailing end wall extending between said anterior wall and said posterior wall, and a leading end wall extending between said anterior wall and said posterior wall opposite said trailing end wall.

7. The instrument of claim 6, wherein said leading end wall is tapered.

8. The instrument of claim 6, wherein said anterior wall, said posterior wall, said leading end wall and said trailing end wall are smooth.

9. The instrument of claim 6, wherein said anterior wall is convex and said posterior wall is concave.

10. The instrument of claim 9, wherein said anterior wall is longer than said posterior wall.

11. The instrument of claim 1, wherein said distal portion is laterally offset by a distance of 10 millimeters.

12. A surgical instrument for performing a surgical procedure in a spinal disc space, comprising:
    a shaft having a length extending substantially along a longitudinal axis, wherein said shaft includes a proximal portion extending along said longitudinal axis, a connecting portion extending from a distal end of said proximal portion along a second axis, said second axis forming a first angle with said longitudinal axis, and a distal portion extending distally from a distal end of said connecting portion along a third axis, said third axis forming a second angle with said second axis such that said distal portion is non-parallel to said proximal portion; and a rasp head extending from a distal end of said distal portion of said shaft.

13. The instrument of claim 12, wherein:

said distal portion of said shaft is offset laterally in a first direction from said proximal portion of said shaft; and said rasp head extends further laterally than said distal portion in said first direction.

14. The instrument of claim 13, wherein said distal portion is laterally offset by a distance of 10 millimeters.

15. The instrument of claim 12, wherein said shaft has a handle along said proximal portion.

16. The instrument of claim 12, wherein said shaft has a circular cross-section.

17. The instrument of claim 12, wherein said rasp head has a shape that generally corresponds to the shape of an implant to be inserted into the intradiscal space.

18. The instrument of claim 12, wherein said rasp head has a first rasping surface positionable against the endplate of an upper vertebral body and an opposite second rasping surface positionable against the endplate of a lower vertebral body.

19. The instrument of claim 12, wherein said first angle is different than said second angle.

20. The instrument of claim 12, wherein a distal extension of said longitudinal axis and a distal extension of said third axis intersect to form an angle of about 5 degrees.

21. The instrument of claim 12, wherein said rasp head has an anterior wall, an opposite posterior wall, a trailing end wall extending between said anterior wall and said posterior wall, and a leading end wall extending between said anterior wall and said posterior wall opposite said trailing end wall.

22. The instrument of claim 21, wherein said leading end wall is tapered.

23. The instrument of claim 21, wherein said anterior wall is convex and said posterior wall is concave.

24. The instrument of claim 23, wherein said anterior wall is longer than said posterior wall.

25. A surgical instrument for performing a surgical procedure in a spinal disc space, comprising:

a shaft having a length extending substantially along a longitudinal axis, wherein said shaft includes:
  a proximal portion extending along said longitudinal axis;
  a connecting portion extending from a distal end of said proximal portion along a second axis, said second axis forming a first angle with said longitudinal axis;
  a distal portion extending distally from a distal end of said connecting portion along a third axis, said third axis forming a second angle with said second axis, wherein a distal extension of said longitudinal axis and a distal extension of said third axis intersect at an angle of about 5 degrees; and
a rasp head extending from a distal end of said distal portion of said shaft.

26. A method of preparing a spinal disc space for insertion of an implant, comprising:

providing a posterior lateral opening into the disc space;
providing a rasp including a shaft extending generally along a longitudinal axis, said shaft having a proximal portion along said longitudinal axis and a distal portion offset laterally to a first side of said longitudinal axis, said rasp further including a rasp head extending from a distal end of said shaft towards said first side; and orienting said shaft so that the spinous process is positioned adjacent said proximal portion on said first side of said longitudinal axis.

27. The method of claim 26, further comprising:

positioning a leading end wall of said rasp head at the opening and the proximal portion of the shaft adjacent the spinous process; and applying a pivoting force to the rasp to move the leading end wall of the rasp towards a distal portion of the disc space and the proximal portion of the shaft away from the spinous process.

28. The method of claim 27, further comprising rasping the vertebral endplates.

29. The method of claim 28, wherein rasping the vertebral endplates includes rasping each endplate separately.

30. The method of claim 28, further comprising inserting an implant into the rasped disc space.

31. The method of claim 30, comprising:

securing a trailing end of the implant to an implant inserter;

positioning a leading end of the implant at the opening;
engaging a pusher to the implant inserter;

applying an impaction force to the implant with the pusher to push the implant through the opening and into the disc space; and applying a pivoting force to the implant with the implant inserter to move the leading end of the implant towards a distal portion of the disc space.

32. The method of claim 31, further comprising alternating between applying an impaction force and applying a pivoting force.

33. The method of claim 31, further comprising removing disc material from the disc space prior to positioning the leading end wall of the implant at the opening.

34. The method of claim 31, further comprising forming a square entrance port at the opening prior to positioning the leading end of the implant at the opening.

35. The method of claim 31, further comprising:

positioning the implant at a distal portion of the disc space; and inserting a second implant into the disc space through the opening after positioning the implant at the distal portion of the disc space.

36. A surgical instrument for performing a surgical procedure in a spinal disc space, comprising:

a shaft extending generally along a longitudinal axis, said shaft having a proximal portion along said longitudinal axis and a distal portion offset laterally in a first direction from said longitudinal axis; and a rasp head at a distal end of said shaft extending in said first direction laterally further from said longitudinal axis than said distal portion, wherein said rasp head has an anterior wall, an opposite posterior wall, a trailing end wall extending between said anterior wall and said posterior wall, and a leading end wall extending between said anterior wall and said posterior wall opposite said trailing end wall and said leading end wall is tapered.

37. The instrument of claim 36, wherein said rasp head has a first rasping surface positionable against the endplate of an upper vertebral body and an opposite second rasping surface positionable against the endplate of a lower vertebral body.

38. The instrument of claim 36, wherein said shaft includes a connecting portion extending along a second axis, said second axis forming a first angle with said longitudinal axis, and said distal portion extending from said connecting portion to said distal end along a third axis, said third axis forming a second angle with said second axis.

39. The instrument of claim 38, wherein said first angle is different that said second angle.

40. The instrument of claim 38, wherein said longitudinal axis and said third axis intersect distally of said rasp head at an angle of about 5 degrees.

41. The instrument of claim 36, wherein said anterior wall, said posterior wall, said leading end wall and said trailing end wall are smooth.

42. The instrument of claim 36, wherein said anterior wall is convex and said posterior wall is concave.

43. The instrument of claim 42, wherein said anterior wall is longer than said posterior wall.

44. The instrument of claim 36, wherein said distal portion is laterally offset by a distance of 10 millimeters.

45. A surgical instrument for performing a surgical procedure in a spinal disc space, comprising:

a shaft extending generally along a longitudinal axis, said shaft having a proximal portion along said longitudinal axis and a distal portion offset laterally in a first direction from said longitudinal axis; and a rasp head at a distal end of said shaft extending in said first direction laterally further from said longitudinal axis than said distal portion, wherein said rasp head has an anterior wall, an opposite posterior wall, a trailing end wall extending between said anterior wall and said posterior wall, and a leading end wall extending between said anterior wall and said posterior wall opposite said trailing end wall, wherein said anterior wall, said posterior wall, said leading end wall and said trailing end wall are smooth.

46. The instrument of claim 45, wherein said rasp head has a first rasping surface positionable against the endplate of an upper vertebral body and an opposite second rasping surface positionable against the endplate of a lower vertebral body.

47. The instrument of claim 45, wherein said shaft includes a connecting portion extending along a second axis, said second axis forming a first angle with said longitudinal axis, and said distal portion extending from said connecting portion to said distal end along a third axis, said third axis forming a second angle with said second axis.

48. The instrument of claim 45, wherein said first angle is different that said second angle.

49. The instrument of claim 45, wherein said longitudinal axis and said third axis intersect distally of said rasp head at an angle of about 5 degrees.

50. The instrument of claim 45, wherein said leading end wall is tapered.

51. The instrument of claim 45, wherein said anterior wall is convex and said posterior wall is concave.

52. The instrument of claim 51, wherein said anterior wall is longer than said posterior wall.

53. The instrument of claim 45, wherein said distal portion is laterally offset by a distance of 10 millimeters.

54. A surgical instrument for performing a surgical procedure in a spinal disc space, comprising:

a shaft extending generally along a longitudinal axis, said shaft having a proximal portion along said longitudinal axis and a distal portion offset laterally in a first direction from said longitudinal axis; and a rasp head at a distal end of said shaft extending in said first direction laterally further from said longitudinal axis than said distal portion, wherein in said rasp head has a convex anterior wall, an opposite concave posterior wall, a trailing end wall extending between said anterior wall and said posterior wall, and a leading end wall extending between said anterior wall and said posterior wall opposite said trailing end wall.

55. The instrument of claim 54, wherein said rasp head has a first rasping surface positionable against the endplate of an upper vertebral body and an opposite second rasping surface positionable against the endplate of a lower vertebral body.

56. The instrument of claim 54, wherein said shaft includes a connecting portion extending along a second axis, said second axis forming a first angle with said longitudinal axis, and said distal portion extending from said connecting portion to said distal end along a third axis, said third axis forming a second angle with said second axis.

57. The instrument of claim 56, wherein said first angle is different that said second angle.

58. The instrument of claim 56, wherein said longitudinal axis and said third axis intersect distally of said rasp head at an angle of about 5 degrees.

59. The instrument of claim 54, wherein said leading end wall is tapered.

60. The instrument of claim 54, wherein said anterior wall, said posterior wall, said leading end wall and said trailing end wall are smooth.

61. The instrument of claim 54, wherein said anterior wall is longer than said posterior wall.

62. The instrument of claim 54, wherein said distal portion is laterally offset by a distance of 10 millimeters.

* * * * *